(12) United States Patent
Han et al.

(10) Patent No.: US 11,246,341 B2
(45) Date of Patent: Feb. 15, 2022

(54) AEROSOL GENERATION METHOD AND APPARATUS

(71) Applicant: KT&G CORPORATION, Daejeon (KR)

(72) Inventors: Jung Ho Han, Daejeon (KR); Jang Uk Lee, Seoul (KR); Hun Il Lim, Seoul (KR); Jong Sub Lee, Gyeonggi-do (KR); Dae Nam Han, Daejeon (KR); Jin Young Yoon, Seoul (KR); Young Lea Kim, Seoul (KR); Ji Soo Jang, Seoul (KR); Wang Seop Lim, Gyeonggi-do (KR); Moon Bong Lee, Seoul (KR); Soung Ho Ju, Daejeon (KR); Du Jin Park, Seoul (KR); Seong Won Yoon, Gyeonggi-do (KR)

(73) Assignee: KT&G CORPORATION, Daejeon (KR)

( * ) Notice: Subject to any disclaimer, the term of this patent is extended or adjusted under 35 U.S.C. 154(b) by 0 days.

(21) Appl. No.: 16/944,495

(22) Filed: Jul. 31, 2020

(65) Prior Publication Data
US 2020/0359681 A1    Nov. 19, 2020

Related U.S. Application Data

(63) Continuation of application No. 16/469,643, filed as application No. PCT/KR2017/012486 on Nov. 6, 2017.

(30) Foreign Application Priority Data

Dec. 16, 2016  (KR) .......................... 10-2016-0172889
Apr. 11, 2017  (KR) .......................... 10-2017-0046938
(Continued)

(51) Int. Cl.
*A24F 40/20*    (2020.01)
*A24F 40/53*    (2020.01)
(Continued)

(52) U.S. Cl.
CPC ................ *A24F 40/20* (2020.01); *A24D 1/20* (2020.01); *A24F 40/40* (2020.01); *A24F 40/46* (2020.01);
(Continued)

(58) Field of Classification Search
None
See application file for complete search history.

(56) References Cited

U.S. PATENT DOCUMENTS 2,638,904 A    5/1953  Mitchell
4,637,407 A    1/1987  Bonanno et al.
(Continued)

FOREIGN PATENT DOCUMENTS

CA    2 973 143 A1     8/2016
CH      310239 A      12/1955
(Continued)

OTHER PUBLICATIONS

Certified Translation of Notice of Allowance issued in KR 10-2018-0010840 dated Dec. 18, 2019, 5 pages.
(Continued)

*Primary Examiner* — Michael J Felton
*Assistant Examiner* — Katherine A Will
(74) *Attorney, Agent, or Firm* — Sughrue Mion, PLLC

(57) ABSTRACT

Provided is an aerosol generating system including a holder configured to generate aerosol by heating a cigarette; and a cradle including an inner space into which the holder is inserted. The holder is configured to be tiltable with respect
(Continued)

the cradle. The holder is inserted into the inner space of the cradle and then tilted to generate the aerosol.

13 Claims, 60 Drawing Sheets

(30) Foreign Application Priority Data

| | | |
|---|---|---|
| Apr. 28, 2017 | (KR) | 10-2017-0055756 |
| Jun. 1, 2017 | (KR) | 10-2017-0068665 |
| Jun. 19, 2017 | (KR) | 10-2017-0077586 |
| Aug. 9, 2017 | (KR) | 10-2017-0100888 |
| Aug. 9, 2017 | (KR) | 10-2017-0101343 |
| Aug. 9, 2017 | (KR) | 10-2017-0101348 |
| Aug. 9, 2017 | (KR) | 10-2017-0101350 |
| Sep. 6, 2017 | (KR) | 10-2017-0113954 |
| Nov. 6, 2017 | (KR) | 10-2017-0146623 |

(51) Int. Cl.

| | |
|---|---|
| *A24F 40/46* | (2020.01) |
| *A24F 40/57* | (2020.01) |
| *A24D 1/20* | (2020.01) |
| *H05B 3/42* | (2006.01) |
| *A24F 40/40* | (2020.01) |

(52) U.S. Cl.
CPC .............. *A24F 40/53* (2020.01); *A24F 40/57* (2020.01); *H05B 3/42* (2013.01); *H05B 2203/021* (2013.01)

(56) References Cited

U.S. PATENT DOCUMENTS

| | | |
|---|---|---|
| 5,144,962 A | 9/1992 | Counts et al. |
| 5,240,012 A | 8/1993 | Ehrman et al. |
| 5,249,586 A | 10/1993 | Morgan et al. |
| 5,388,594 A | 2/1995 | Counts et al. |
| 5,465,738 A | 11/1995 | Rowland |
| 5,479,948 A | 1/1996 | Counts et al. |
| 5,591,368 A | 1/1997 | Fleischhauer et al. |
| 5,666,977 A | 9/1997 | Higgins et al. |
| 5,666,978 A * | 9/1997 | Counts .................. A24F 47/008 131/194 |
| 5,878,752 A | 3/1999 | Adams et al. |
| 6,053,176 A | 4/2000 | Adams et al. |
| 6,418,938 B1 | 7/2002 | Fleischhauer et al. |
| 6,532,965 B1 | 3/2003 | Abhulimen et al. |
| 6,615,840 B1 | 9/2003 | Fournier et al. |
| 6,810,883 B2 | 11/2004 | Felter et al. |
| 7,861,726 B1 | 1/2011 | Lukasavitz |
| 8,375,959 B2 | 2/2013 | Dittrich et al. |
| 8,419,085 B2 | 4/2013 | Kim et al. |
| 8,752,545 B2 | 6/2014 | Buchberger |
| 8,851,081 B2 | 10/2014 | Fernando et al. |
| 8,973,587 B2 | 3/2015 | Liu |
| 9,078,472 B2 | 7/2015 | Liu |
| 9,078,473 B2 | 7/2015 | Worm et al. |
| 9,271,528 B2 | 3/2016 | Liu |
| 9,320,299 B2 | 4/2016 | Hearn et al. |
| 9,423,152 B2 | 8/2016 | Ampolini et al. |
| 9,427,023 B2 | 8/2016 | Liu |
| 9,497,991 B2 | 11/2016 | Besso et al. |
| 9,499,332 B2 | 11/2016 | Fernando et al. |
| 9,516,899 B2 | 12/2016 | Plojoux et al. |
| 9,560,883 B2 | 2/2017 | Hawes |
| 9,603,388 B2 | 3/2017 | Fernando et al. |
| 9,655,383 B2 | 5/2017 | Holzherr et al. |
| 9,693,587 B2 | 7/2017 | Plojoux et al. |
| 9,723,871 B2 | 8/2017 | Xiang |
| 9,814,263 B2 | 11/2017 | Cochand et al. |
| 9,854,841 B2 | 1/2018 | Ampolini et al. |
| 9,854,845 B2 | 1/2018 | Plojoux et al. |
| 9,894,934 B2 | 2/2018 | Li et al. |
| 9,918,494 B2 | 3/2018 | Mironov et al. |
| 9,955,724 B2 | 5/2018 | Lord |
| 9,986,760 B2 | 6/2018 | Macko et al. |
| 9,999,247 B2 | 6/2018 | Ruscio et al. |
| 10,015,990 B2 | 7/2018 | Mironov |
| 10,031,183 B2 | 7/2018 | Novak, III et al. |
| 10,070,667 B2 | 9/2018 | Lord et al. |
| 10,104,911 B2 | 10/2018 | Thorens et al. |
| 10,130,780 B2 | 11/2018 | Talon |
| 10,136,673 B2 | 11/2018 | Mironov |
| 10,159,283 B2 | 12/2018 | Mironov |
| 10,194,697 B2 | 2/2019 | Fernando et al. |
| 10,299,513 B2 | 5/2019 | Perez et al. |
| 10,368,584 B2 | 8/2019 | Fernando et al. |
| 10,439,419 B2 | 10/2019 | Bernauer et al. |
| 10,440,987 B2 | 10/2019 | Zeng et al. |
| 10,448,670 B2 | 10/2019 | Talon et al. |
| 10,492,542 B1 | 12/2019 | Worm et al. |
| 10,548,350 B2 | 2/2020 | Greim et al. |
| 10,555,553 B2 | 2/2020 | Binassi et al. |
| 10,588,351 B2 | 3/2020 | Ricketts |
| 10,645,971 B2 | 5/2020 | Zitzke |
| 10,667,329 B2 | 5/2020 | Bernauer et al. |
| 10,668,058 B2 | 6/2020 | Rose et al. |
| 10,716,329 B2 | 7/2020 | Matsumoto et al. |
| 10,813,174 B2 | 10/2020 | Schneider et al. |
| 10,869,503 B2 | 12/2020 | Yamada et al. |
| 10,881,137 B2 | 1/2021 | Suzuki et al. |
| 11,039,642 B2 | 6/2021 | Zuber et al. |
| 11,147,316 B2 | 10/2021 | Farine et al. |
| 2004/0261802 A1 | 12/2004 | Griffin et al. |
| 2005/0045198 A1 | 3/2005 | Larson et al. |
| 2005/0172976 A1 | 8/2005 | Newman et al. |
| 2008/0001052 A1 | 1/2008 | Kalous et al. |
| 2010/0307518 A1 | 12/2010 | Wang |
| 2011/0155151 A1 | 6/2011 | Newman et al. |
| 2011/0290269 A1 | 12/2011 | Shimizu |
| 2012/0247494 A1 | 10/2012 | Oglesby et al. |
| 2013/0037041 A1 | 2/2013 | Worm et al. |
| 2013/0213419 A1 | 8/2013 | Tucker et al. |
| 2013/0284192 A1 | 10/2013 | Peleg et al. |
| 2013/0319439 A1 | 12/2013 | Gorelick et al. |
| 2013/0340775 A1 | 12/2013 | Juster et al. |
| 2014/0020698 A1 | 1/2014 | Fiebelkorn |
| 2014/0096782 A1 | 4/2014 | Ampolini et al. |
| 2014/0116455 A1 | 5/2014 | Youn |
| 2014/0246035 A1 | 9/2014 | Minskoff et al. |
| 2014/0299137 A1 | 10/2014 | Kieckbusch et al. |
| 2014/0318559 A1 | 10/2014 | Thorens et al. |
| 2014/0345634 A1 | 11/2014 | Zuber et al. |
| 2014/0363145 A1 | 12/2014 | Plojoux et al. |
| 2015/0007838 A1 | 1/2015 | Fernando et al. |
| 2015/0013696 A1 | 1/2015 | Plojoux et al. |
| 2015/0024355 A1 | 1/2015 | Ghofrani et al. |
| 2015/0027474 A1 | 1/2015 | Zuber et al. |
| 2015/0100441 A1 | 4/2015 | Alarcon et al. |
| 2015/0136124 A1 | 5/2015 | Aronie et al. |
| 2015/0136154 A1 | 5/2015 | Mitrev et al. |
| 2015/0201676 A1 | 7/2015 | Shin |
| 2015/0208725 A1 | 7/2015 | Tsai |
| 2015/0245654 A1 | 9/2015 | Memari et al. |
| 2015/0257445 A1 | 9/2015 | Henry, Jr. et al. |
| 2015/0272211 A1 | 10/2015 | Chung |
| 2016/0031032 A1 | 2/2016 | Malgat et al. |
| 2016/0150824 A1 | 6/2016 | Memari et al. |
| 2016/0205998 A1 | 7/2016 | Matsumoto et al. |
| 2016/0270437 A1 | 9/2016 | Nappi |
| 2016/0286861 A1 | 10/2016 | Liu |
| 2016/0302488 A1 | 10/2016 | Fernando et al. |
| 2016/0331032 A1 | 11/2016 | Malgat et al. |
| 2016/0345629 A1 | 12/2016 | Mironov |
| 2016/0366946 A1 | 12/2016 | Murison et al. |
| 2016/0374402 A1 | 12/2016 | Fernando et al. |
| 2017/0006916 A1 | 1/2017 | Liu |
| 2017/0027229 A1 | 2/2017 | Cameron |
| 2017/0027234 A1 | 2/2017 | Farine et al. |
| 2017/0042243 A1 | 2/2017 | Plojoux et al. |
| 2017/0055580 A1 | 3/2017 | Blandino et al. |

(56) References Cited

U.S. PATENT DOCUMENTS

| | | |
|---|---|---|
| 2017/0071251 A1 | 3/2017 | Goch |
| 2017/0095006 A1 | 4/2017 | Egoyants et al. |
| 2017/0150757 A1 | 6/2017 | Worm et al. |
| 2017/0164659 A1 | 6/2017 | Schneider et al. |
| 2017/0172214 A1 | 6/2017 | Li et al. |
| 2017/0172215 A1 | 6/2017 | Li et al. |
| 2017/0188634 A1 | 7/2017 | Plojoux et al. |
| 2017/0238596 A1 | 8/2017 | Matsumoto et al. |
| 2018/0177234 A1 | 6/2018 | Lee |
| 2018/0206556 A1 | 7/2018 | Thorens et al. |
| 2018/0235283 A1 | 8/2018 | Zuber et al. |
| 2019/0014826 A1 | 1/2019 | Thorens et al. |
| 2019/0075849 A1 | 3/2019 | Hawes |
| 2019/0320719 A1 | 10/2019 | Liu et al. |
| 2019/0364975 A1 | 12/2019 | Fernando et al. |
| 2020/0120983 A1 | 4/2020 | Chen |
| 2020/0232766 A1 | 7/2020 | Flick |
| 2020/0305508 A1 | 10/2020 | Talon |
| 2020/0352224 A1 | 11/2020 | Plojoux et al. |
| 2020/0413495 A1 | 12/2020 | Schneider et al. |
| 2021/0000182 A1 | 1/2021 | Ruscio et al. |
| 2021/0120875 A1 | 4/2021 | Mironov |

FOREIGN PATENT DOCUMENTS

| | | | |
|---|---|---|---|
| CN | 1102964 | A | 5/1995 |
| CN | 1209731 | A | 3/1999 |
| CN | 1973706 | A | 6/2007 |
| CN | 101043827 | A | 9/2007 |
| CN | 101444335 | A | 6/2009 |
| CN | 102006790 | A | 4/2011 |
| CN | 102438470 | A | 5/2012 |
| CN | 202407082 | U | 9/2012 |
| CN | 202774134 | U | 3/2013 |
| CN | 103096741 | A | 5/2013 |
| CN | 103281920 | A | 9/2013 |
| CN | 103338665 | A | 10/2013 |
| CN | 203457802 | U | 3/2014 |
| CN | 103859606 | A | 6/2014 |
| CN | 203633505 | U | 6/2014 |
| CN | 103929988 | A | 7/2014 |
| CN | 203689071 | U | 7/2014 |
| CN | 103974640 | A | 8/2014 |
| CN | 103997921 | A | 8/2014 |
| CN | 103997922 | A | 8/2014 |
| CN | 203789137 | U | 8/2014 |
| CN | 104023568 | A | 9/2014 |
| CN | 104023574 | A | 9/2014 |
| CN | 104039183 | A | 9/2014 |
| CN | 104095295 | A | 10/2014 |
| CN | 104106842 | A | 10/2014 |
| CN | 203943078 | U | 11/2014 |
| CN | 204070570 | U | 1/2015 |
| CN | 204146338 | U | 2/2015 |
| CN | 104382237 | A | 3/2015 |
| CN | 104470387 | A | 3/2015 |
| CN | 104489933 | A | 4/2015 |
| CN | 104544559 | A | 4/2015 |
| CN | 204317494 | U | 5/2015 |
| CN | 204317504 | U | 5/2015 |
| CN | 104754964 | A | 7/2015 |
| CN | 104770878 | A | 7/2015 |
| CN | 104812260 | A | 7/2015 |
| CN | 204444239 | U | 7/2015 |
| CN | 204763414 | U | 11/2015 |
| CN | 105163610 | A | 12/2015 |
| CN | 105208882 | A | 12/2015 |
| CN | 105208884 | A | 12/2015 |
| CN | 105341993 | A | 2/2016 |
| CN | 105342011 | A | 2/2016 |
| CN | 105357994 | A | 2/2016 |
| CN | 205018293 | U | 2/2016 |
| CN | 105361250 | A | 3/2016 |
| CN | 105453598 | A | 3/2016 |
| CN | 205180371 | U | 4/2016 |
| CN | 205197003 | U | 5/2016 |
| CN | 205337598 | U | 6/2016 |
| CN | 105747281 | A | 7/2016 |
| CN | 105831812 | A | 8/2016 |
| CN | 105876869 | A | 8/2016 |
| CN | 205512358 | U | 8/2016 |
| CN | 205597118 | U | 9/2016 |
| CN | 106037014 | A | 10/2016 |
| CN | 205648910 | U | 10/2016 |
| CN | 106102492 | A | 11/2016 |
| CN | 106132217 | A | 11/2016 |
| CN | 106163307 | A | 11/2016 |
| CN | 205728067 | U | 11/2016 |
| CN | 106174699 | A | 12/2016 |
| CN | 106231934 | A | 12/2016 |
| CN | 106413439 | A | 2/2017 |
| CN | 106413444 | A | 2/2017 |
| CN | 106455708 | A | 2/2017 |
| CN | 106455714 | A | 2/2017 |
| CN | 106455716 | A | 2/2017 |
| CN | 106473233 | A | 3/2017 |
| CN | 106901404 | A | 6/2017 |
| DE | 3302518 | A1 | 7/1984 |
| EA | 012169 | B1 | 8/2009 |
| EA | 201390819 | A1 | 9/2013 |
| EP | 1119267 | B1 | 7/2004 |
| EP | 2 113 178 | A1 | 11/2009 |
| EP | 2 201 850 | A1 | 6/2010 |
| EP | 2 531 053 | B1 | 9/2015 |
| EP | 3 098 738 | A1 | 11/2016 |
| EP | 2 432 339 | B1 | 3/2017 |
| EP | 3275319 | A1 | 1/2018 |
| ER | 2253233 | A1 | 11/2010 |
| ER | 3 179 828 | A1 | 6/2017 |
| ER | 3 289 895 | A1 | 3/2018 |
| GB | 2542018 | A | 3/2017 |
| JP | 3-232481 | A | 10/1991 |
| JP | 7-184627 | A | 7/1995 |
| JP | 11-164679 | A | 6/1999 |
| JP | 3645921 | B2 | 5/2005 |
| JP | 2006-320286 | A | 11/2006 |
| JP | 4278306 | B2 | 6/2009 |
| JP | 2010-526553 | A | 8/2010 |
| JP | 2011-87569 | A | 5/2011 |
| JP | 2011-518567 | A | 6/2011 |
| JP | 4739433 | B2 | 8/2011 |
| JP | 2012-527222 | A | 11/2012 |
| JP | 2014-500017 | A | 1/2014 |
| JP | 2014-521419 | A | 8/2014 |
| JP | 2014-525237 | A | 9/2014 |
| JP | 2014-533513 | A | 12/2014 |
| JP | 2014-534813 | A | 12/2014 |
| JP | 2015-503916 | A | 2/2015 |
| JP | 2015-507477 | A | 3/2015 |
| JP | 2015-508996 | | 3/2015 |
| JP | 2015506170 | A | 3/2015 |
| JP | 2015-524261 | A | 8/2015 |
| JP | 2015-180214 | A | 10/2015 |
| JP | 2015-529458 | A | 10/2015 |
| JP | 2015-204833 | A | 11/2015 |
| JP | 2016-528910 | A | 9/2016 |
| JP | 2017-51189 | A | 3/2017 |
| JP | 2017-70297 | A | 4/2017 |
| JP | 2017-514463 | A | 6/2017 |
| JP | 2010178730 | A | 8/2020 |
| KR | 10-0304044 | B1 | 11/2001 |
| KR | 10-0806461 | B1 | 2/2008 |
| KR | 10-0965099 | B1 | 6/2010 |
| KR | 10-1001077 | A | 12/2010 |
| KR | 10-2011-0096548 | A | 8/2011 |
| KR | 20-2011-0009632 | U | 10/2011 |
| KR | 10-1098112 | B1 | 12/2011 |
| KR | 10-2012-0027029 | A | 3/2012 |
| KR | 10-2012-0101637 | A | 9/2012 |
| KR | 10-2012-0109634 | A | 10/2012 |
| KR | 10-2012-0114333 | A | 10/2012 |
| KR | 10-2012-0121314 | A | 11/2012 |
| KR | 10-2013-0027909 | A | 3/2013 |
| KR | 20-0466757 | Y1 | 5/2013 |

(56) References Cited

FOREIGN PATENT DOCUMENTS

| | | |
|---|---|---|
| KR | 10-2013-0081238 | 7/2013 |
| KR | 10-2013-0139296 A | 12/2013 |
| KR | 10-1383577 B1 | 4/2014 |
| KR | 10-2014-0068203 A | 6/2014 |
| KR | 10-2014-0092312 A | 7/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-1523088 B2 | 5/2015 |
| KR | 10-2015-0099704 A | 9/2015 |
| KR | 10-2015-0099771 A | 9/2015 |
| KR | 10-1184499 | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0015144 A | 2/2016 |
| KR | 10-2016-0040643 A | 4/2016 |
| KR | 10-1609715 B1 | 4/2016 |
| KR | 10-2016-0052607 A | 5/2016 |
| KR | 10-2016-0060006 A | 5/2016 |
| KR | 10-1619032 A | 5/2016 |
| KR | 10-1619032 B1 | 5/2016 |
| KR | 20-2016-0001476 | 5/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-1656061 B1 | 9/2016 |
| KR | 10-2016-0114743 A | 10/2016 |
| KR | 10-2016-0124091 A | 10/2016 |
| KR | 10-1667124 B1 | 10/2016 |
| KR | 10-1668175 B1 | 10/2016 |
| KR | 10-2016-0129024 | 11/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 A | 1/2017 |
| KR | 10-2017-0044158 A | 4/2017 |
| KR | 10-2017-0071486 A | 6/2017 |
| KR | 10-2017-0074898 A | 6/2017 |
| KR | 10-1740160 B1 | 6/2017 |
| RU | 2302806 C2 | 7/2007 |
| RU | 2425608 C2 | 8/2011 |
| RU | 2 531 890 C2 | 10/2014 |
| RU | 2564600 C1 | 10/2015 |
| RU | 2014 125 232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 053 C2 | 11/2016 |
| RU | 2 602 962 C2 | 11/2016 |
| RU | 2 603 559 C2 | 11/2016 |
| RU | 2 604 012 C2 | 12/2016 |
| WO | 94/06314 A1 | 3/1994 |
| WO | 98/23171 A1 | 6/1998 |
| WO | 00/27232 A1 | 5/2000 |
| WO | 2010/133342 A1 | 11/2010 |
| WO | 2011/028372 A1 | 3/2011 |
| WO | 2011/050964 A1 | 5/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A2 | 5/2013 |
| WO | 2013/098395 A1 | 7/2013 |
| WO | 2013/098398 A3 | 7/2013 |
| WO | 2013/098409 A1 | 7/2013 |
| WO | 2013/102612 A2 | 7/2013 |
| WO | 2013102609 A2 | 7/2013 |
| WO | 2013/120565 A3 | 8/2013 |
| WO | 2013/126777 A2 | 8/2013 |
| WO | 2013/137084 A1 | 9/2013 |
| WO | 2013/171217 A1 | 11/2013 |
| WO | 2013/190036 A1 | 12/2013 |
| WO | 2014/029880 A2 | 2/2014 |
| WO | 2015/046386 A1 | 4/2015 |
| WO | 2015/088744 A1 | 6/2015 |
| WO | 2015128665 | 9/2015 |
| WO | 2015/155289 A1 | 10/2015 |
| WO | 2015/165813 A1 | 11/2015 |
| WO | 2015/177044 A1 | 11/2015 |
| WO | 2015/197627 A1 | 12/2015 |
| WO | 2016/059073 A1 | 4/2016 |
| WO | 2016/075028 A1 | 5/2016 |
| WO | 2016/076147 A1 | 5/2016 |
| WO | 2016/107766 A1 | 7/2016 |
| WO | 2016/124550 A1 | 8/2016 |
| WO | 2016/124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016/159013 A1 | 10/2016 |
| WO | 2016/166064 A1 | 10/2016 |
| WO | 2016/178377 A1 | 11/2016 |
| WO | 2017/029088 A1 | 2/2017 |
| WO | 2017/029089 A1 | 2/2017 |
| WO | 2017/037457 A1 | 3/2017 |
| WO | 2017/042297 A1 | 3/2017 |
| WO | 2017/075759 A1 | 5/2017 |
| WO | 2017/139963 A1 | 8/2017 |
| WO | 2018/050449 A1 | 3/2018 |
| WO | 2018/189195 A1 | 10/2018 |
| WO | 2019/020826 A1 | 1/2019 |
| WO | 2019/030172 A1 | 2/2019 |
| WO | 2019/095268 A1 | 5/2019 |

OTHER PUBLICATIONS

Office Action dated Dec. 11, 2019 in Korean Application No. 10-2018-0010836.
Office Action dated Dec. 11, 2019 in Korean Application No. 10-2018-0010841.
Office Action dated Dec. 19, 2019 in Korean Application No. 10-2018-0090910.
Office Action dated Jan. 3, 2020 in Korean Application No. 10-2018-0012456.
Office Action dated Jan. 3, 2020 in Korean Application No. 10-2017-0084389.
Office Action dated Jan. 3, 2020 in Korean Application No. 10-2017-0084386.
Office Action dated Jan. 3, 2020 in Korean Application No. 10-2018-0018693.
Office Action dated Jan. 8, 2020 in Korean Application No. 10-2017-0128293.
Office Action dated Jan. 8, 2020 in Korean Application No. 10-2017-0119664.
Office Action dated Jan. 16, 2020 in Korean Application No. 10-2017-0084388.
Office Action dated Jan. 16, 2020 in Korean Application No. 10-2017-0084387.
Office Action dated Feb. 11, 2020 in Korean Application No. 10-2018-0010834.
Office Action dated Feb. 11, 2020 in Korean Application No. 10-2018-0010835.
Office Action dated Feb. 13, 2020 in Korean Application No. 10-2018-0010837.

(56) References Cited

OTHER PUBLICATIONS

Office Action dated Feb. 18, 2020 in Russian Application No. 2019121813.
Office Action dated Nov. 14, 2019 in Korean Application No. 10-2017-0084385.
Office Action dated Nov. 14, 2019 in Korean Application No. 10-2017-0147605.
Office Action dated Aug. 7, 2019 in Korean Application No. 10-2018-0067035 and translation.
Office Action dated Jun. 27, 2019, in Korean Application No. 10-2018-0063759 and translation.
Office Action dated Jul. 2, 2019 in Korean Application No. 10-2019-0018815 and translation.
Office Action dated Jul. 3, 2019 in Korean Application No. 10-2019-0017391 and translation.
International Preliminary Report on Patentability (Chapter I) dated Jun. 18, 2019, in PCT/KR2017/012486 and translation.
International Search Report in PCT/KR2017/012486 dated May 29, 2018 and translation (now WO 2018/110834).
Written Opinion of the International Searching Authority in PCT/KR2017/012486 dated May 29, 2018 and translation.
Partial supplementary European search report dated Aug. 3, 2020 in Application No. 17880867.1.
Extended European search report dated Nov. 4, 2020 by the European Patent Office in Application No. 17880867.1.
Office Action dated Oct. 29, 2020 by the Korean Patent Office in Application No. 10-2018-0010837.
Office Action dated Nov. 4, 2020 by the Japanese Patent Office in Application No. 2019-554453.
Decision on Grant dated Nov. 26, 2020 by the Russian Federal Service For Intellectual Property Patent Application No. 2020124607.
Office Action dated Nov. 26, 2020 by Russian Federal Service For Intellectual Property Office Patent Application No. 2020124609.
Decision on Grant dated Oct. 26, 2020 by Russian Federal Service For Intellectual Property in Application No. 2020124610.
Office Action dated Jun. 29, 2020 by the Korean Patent Office in Application No. 10-2018-0010836.
Office Action dated Nov. 4, 2020 by the Japanese Patent Office in Application No. 2020-128346.
Extended European Search Report dated Jan. 14, 2021 in European Application No. 18783776.0.
Extended European Search Report dated Jan. 25, 2021 in European Application No. 18785166.2.
Extended European Search Report dated Jan. 29, 2021 in European Application No. 18784464.2.
Extended European Search Report dated Mar. 15, 2021 in European Application No. 18785061.5.
Extended European Search Report dated Mar. 19, 2021 in European Application No. 18784164.8.
Extended European Search Report dated Mar. 24, 2021 in European Application No. 18784268.7.
Extended European Search Report dated Mar. 25, 2021 in European Application No. 18784370.1.
Extended European Search Report dated Mar. 25, 2021 in European Application No. 18784841.1.
Office Action dated Feb. 24, 2021 in Japanese Application No. 2019-555168.
Office Action datedFeb. 24, 2021 in Japanese Application No. 2019-555203.
Office Action dated Feb. 24, 2021 in Japanese Application No. 2019-555204.
Office Action dated Feb. 4, 2021 in Russian Application No. 2020124609.
Office Action dated Feb. 9, 2021 in Japanese Application No. 2019-555184.
Office Action dated Jan. 26, 2021 in Japanese Application No. 2020-501521.
Office Action dated Mar. 2, 2021 in Japanese Application No. 2019-555170.
Office Action dated Mar. 2, 2021 in Japanese Application No. 2019-555182.
Office Action dated Mar. 30, 2021 in Japanese Application No. 2020-501377.
Office Action dated Jan. 19, 2021 in Indonesian Application No. P00201906007.
Communication dated Jan. 15, 2021 by the European Patent Office in application No. 20188949.0.
Extended European Search Report dated Dec. 10, 2020 in European Application No. 20188932.6.
Extended European Search Report dated Dec. 16, 2020 in European Application No. 20188985.4.
Extended European Search Report dated Dec. 18, 2020 in European Application No. 18775504.6.
Extended European Search Report dated Dec. 18, 2020 in European Application No. 20188926.8.
Extended European Search Report dated Nov. 19, 2020 in European Application No. 20188792.4.
Office Action dated Dec. 1, 2020 in Japanese Application No. 2020-501188.
Office Action dated Dec. 11, 2020 in Russian Application No. 2020124653.
Office Action dated Dec. 28, 2020 in Russian Application No. 2020124652.
Office Action dated Dec. 30, 2020 in Russian Application No. 2020124651.
Office Action dated Jan. 12, 2021 in Japanese Application No. 2019-555169.
Office Action dated Jan. 12, 2021 in Japanese Application No. 2019-555201.
Office Action dated Jan. 19, 2021 in Japanese Application No. 2019-553569.
Office Action dated Jan. 19, 2021 in Japanese Application No. 2020-501514.
Office Action dated May 28, 2020 in Korean Application No. 10-2017-0147605.
Office Action dated Sep. 24, 2020 in Korean Application No. 10-2018-0012456.
Extended European Search Report dated Apr. 1, 2021 in European Application No. 18805933.1.
Extended European Search Report dated Jun. 14, 2021 in European Application No. 18842951.8.
Extended European Search Report dated Jun. 16, 2021 in European Application No. 18853434.1.
Office Action dated Apr. 2, 2019 in Korean Application No. 10-2019-0021286.
Office Action dated Apr. 25, 2019 in Korean Application No. 10-2019-0033721.
Office Action dated Apr. 25, 2019 in Korean Application No. 10-2019-0033784.
Office Action dated Apr. 3, 2019 in Korean Application No. 10-2019-0018812.
Office Action dated Apr. 4, 2019 in Korean Application No. 10-2019-0019194.
Office Action dated Apr. 4, 2019 in Korean Application No. 10-2019-0019195.
Office Action dated Apr. 4, 2019 in Korean Application No. 10-2019-0020484.
Office Action dated Apr. 9, 2021 in Korean Application No. 10-2020-0116256.
Office Action dated May 5, 2021 in Canadian Application No. 3,047,236.
International Search Report dated Feb. 28, 2019 from the International Searching Authority in International Application No. PCT/KR2018/009100.
International Search Report dated Jul. 24, 2018 from the International Searching Authority in International Application No. PCT/KR2018/003691.
International Search Report dated Nov. 14, 2018 from the International Searching Authority in International Application No. PCT/KR2018/004118.

(56) References Cited

OTHER PUBLICATIONS

International Search Report dated Nov. 26, 2018 from the International Searching Authority in International Application No. PCT/KR2018/009094.
International Search Report dated Nov. 6, 2018 from the International Searching Authority in International Application No. PCT/KR2018/004129.
International Search Report dated Nov. 6, 2018 from the International Searching Authority in International Application No. PCT/KR2018/004130.
International Search Report dated Nov. 6, 2018 from the International Searching Authority in International Application No. PCT/KR2018/004178.
International Search Report dated Septembers, 2018 from the International Searching Authority in International Application No. PCT/KR2018/004176.
International Search Report dated Septembers, 2018 from the International Searching Authority in International Application No. PCT/KR2018/004179.
International Search Report dated Sep. 7, 2018 from the International Searching Authority in International Application No. PCT/KR2018/004171.
International Search Report dated Sep. 7, 2018 from the International Searching Authority in International Application No. PCT/KR2018/004172.
International Search Report dated Aug. 29, 2018 in International Application No. PCT/KR2018/005945.
International Search Report dated Dec. 4, 2018 in International Application No. PCT/KR2018/006747.
International Search Report dated Nov. 30, 2018 in International Application No. PCT/KR2018/006702.
Communication dated Jun. 29, 2021 by the Chinese Patent Office in Chinese Application No. 201880022072.2.
Extended European Search Report dated Jul. 1, 2021 in European Application No. 18854661.8.
Office Action dated Jul. 22, 2021 in Korean Application No. 10-2021-0051359.
Office Action dated Apr. 5, 2019 in Korean Application No. 10-2019-0027638.
Office Action dated Jun. 10, 2021 in Russian Application No. 2020124657.
Office Action dated Jun. 10, 2021 in Russian Application No. 2020124658.
Communication dated Aug. 16, 2021 by the Chinese Patent Office in Chinese Application No. 201880024006.9.
Communication dated Aug. 26, 2021 by the Chinese Patent Office in Chinese Application No. 201880024107.6.
Communication dated Aug. 4, 2021 by the Chinese Patent Office in Chinese Application No. 201880024289.7.
Communication dated Jul. 16, 2021 by the Chinese Patent Office in Chinese Application No. 201880024367.3.
Communication dated Jul. 19, 2021 by the Chinese Patent Office in Chinese Application No. 201880024070.7.
Communication dated Jul. 26, 2021 by the Chinese Patent Office in Chinese Application No. 201880024059.0.
Communication dated Jul. 27, 2021 by the Chinese Patent Office in Chinese Application No. 201780084891.5.
Communication dated Sep. 17, 2021 by the Chinese Patent Office in Chinese Application No. 201880030699.2.
Extended European Search Report dated Oct. 27, 2021 in European Application No. 18844735.3.
Office Action dated Oct. 28, 2021 in Chinese Application No. 201880046418.2.
Office Action dated Sep. 24, 2021 in Chinese Application No. 201880024010.5.
Office Action dated Sep. 29, 2021 in Chinese Application No. 201880024276.X.
Office Action dated Sep. 29, 2021 in Chinese Application No. 201880024311.8.
Office Action dated Nov. 25, 2021 in Chinese Application No. 201880047174.X.
Office Action dated Dec. 1, 2021 in Chinese Application No. 201880046367.3.

* cited by examiner

AEROSOL GENERATION METHOD AND APPARATUS

This application is a Continuation of U.S. application Ser. No. 16/469,643, filed Jun. 14, 2019, which is a National Stage of International Application No. PCT/KR2017/012486 filed Nov. 6, 2017, which claims priority to Korean Application Nos. 10-2016-0172889 filed Dec. 16, 2016; 10-2017-0046938 filed Apr. 11, 2017; 10-2017-0055756 filed Apr. 28, 2017; 10-2017-0068665 filed Jun. 1, 2017; 10-2017-0077586 filed Jun. 19, 2017; 10-2017-0101343, 10-2017-0100888, 10-2017-0101350, and 10-2017-0101348 filed Aug. 9, 2017; 10-2017-0113954 filed Sep. 6, 2017; and 10-2017-0146623 filed Nov. 6, 2017, all of which are incorporated herein by reference in their entirety.

TECHNICAL FIELD

The present disclosure relates to a method and an apparatus for generating aerosols. More particularly, the present disclosure relates to a method and an apparatus for generating aerosol by heating an aerosol generating material in a cigarette.

BACKGROUND ART

Recently, there is a growing demand for alternative methods for resolving problems of a common cigarette. For example, there is a growing demand for a method of generating aerosol by heating an aerosol generating material in a cigarette instead of burning the cigarette to generate aerosol. Therefore, researches on heating-type cigarettes or heating-type aerosol generating apparatuses are being actively carried out.

DESCRIPTION OF EMBODIMENTS

Technical Problem

Provided are a method and an apparatus for generating aerosols. Also, provided is a computer-readable recording medium having recorded thereon a program for executing the above method on a computer. Technical problems to be solved are not limited to the technical problems as described above, and other technical problems may exist.

Solution to Problem

According to an aspect of the present disclosure, an aerosol generating system includes a holder configured to generate aerosol by heating a cigarette; and a cradle including an inner space into which the holder is inserted, wherein the holder is inserted into the inner space of the cradle and then tilted to generate the aerosol.

Advantageous Effects of Disclosure

A holder may generate aerosol by heating a cigarette. Also, aerosol may be generated independently by the holder or even when the holder is inserted into a cradle and is tilted. Particularly, when the holder Is tilted, a heater may be heated by power of a battery of the cradle.

Also, the heater has a smooth surface for smooth insertion of a cigarette, and the heater is not damaged by frictional force during insertion of a cigarette.

Also, the operation of the holder may be continuously monitored in any state including a state in which the holder is coupled with the cradle and tilted or a state in which the holder is separated from the cradle.

Also, a cooling structure included in a cigarette may cool aerosol passing through the cooling structure. Particularly, uniform channels are distributed in the cooling structure, and thus aerosol may flow smoothly and the aerosol cooling effect may be improved.

The cooling structure also has the effect of filtering certain materials included in aerosol. Also, since the cooling structure may be made of pure polylactic acid, specific materials may be prevented from being generated as aerosol passes through the cooling structure.

Also, as a vortex is formed while aerosol is passing through the cooling structure, the aerosol cooling effect and specific material filtering effect are improved.

Also, an aerosol generating apparatus in which a holder and a cradle are combined (integrated) may be provided. According to the aerosol generating apparatus, a user may mount a cigarette in the aerosol generating apparatus by pushing the cigarette along the accommodating path of an accommodating portion.

Also, after the use of the cigarette is completed, the user may easily separate the cigarette from the aerosol generating apparatus by a simple action for separating the cigarette from the accommodating portion of a casing.

Also, since the accommodating portion may be separated from the casing, a tobacco material which is generated during smoking and attached to the periphery of the cigarette may be easily discharged out of the casing together with the accommodating portion.

Also, when the accommodating portion is separated from the casing, a protruding tube and a heater are exposed to the outside, and thus the user may directly check the states thereof and easily perform a cleaning operation.

In addition, while a cigarette is being inserted into the accommodating portion of the aerosol generating apparatus, a protruding portion protruding from the accommodating path or a cigarette supporting protrusion of the cover comes into contact with the cigarette, and thus the cigarette is stably supported. Therefore, the state that a cigarette is accommodated in the aerosol generating apparatus is stably maintained while the aerosol generating apparatus is being used, and thus a user may safely enjoy the aerosol generating apparatus Also, as the protruding portion contacts a portion of the outer surface of a cigarette, a flow path in which the air may pass is formed between the accommodating path and the cigarette, and thus the outside air to assist generation of aerosol may be supplied smoothly and sufficiently into the aerosol generating apparatus.

Also, by reducing a contact area between a cigarette and the accommodating path, a heat conduction area through which heat is transmitted from the cigarette to the casing may be reduced.

Also, since a cigarette and the accommodating path are apart from each other, even when the heater is inserted into the cigarette and the cigarette expands, the cigarette is easily inserted into the accommodating path of the accommodating portion.

When there is no space between a cigarette and the accommodating portion, the outer wall of the cigarette expands while the heater is being inserted into the cigarette and the frictional force between the cigarette and the accommodating portion increases, and thus it becomes difficult to insert the cigarette into the accommodating portion.

Also, the accommodating portion may be cooled by introducing the outside air stream into the space formed between the outer surface of the cigarette and the accommodating path.

Also, the air introduced into the cigarette may be preheated by the configuration of the aerosol generating apparatus with the accommodating path and the protruding portion.

Also, since a mechanism for moving the accommodating portion with regard to the aerosol generating apparatus when the accommodating portion is not separated from the aerosol generating apparatus is not used, the number of components is reduced, thereby simplifying the overall configuration of the aerosol generating apparatus and preventing frequent troubles related to a movable accommodating portion.

BEST MODE

Figure 1:
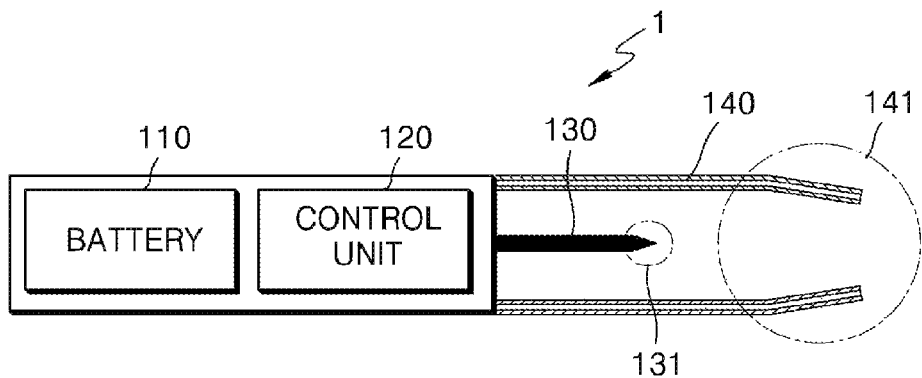
FIG. 1 is a block diagram showing an example of an aerosol generating apparatus.

According to an aspect of the present disclosure, there is provided an aerosol generating system including a holder configured to generate aerosol by heating a cigarette; and a cradle including an inner space into which the holder is inserted, wherein the holder is inserted into the inner space of the cradle and then tilted to generate the aerosol.

In the above-described aerosol generating system, the holder is tilted at an angle of equal to or greater than 5° and less than or equal to 90° when the holder is being inserted into the cradle.

In the above-described aerosol generating system, when the holder is tilted, the holder heats a heater included in the holder by using power supplied from a battery included in the cradle.

According to another aspect of the present disclosure, there is provided a heater including a heating unit including a base portion having a tubular shape and a tip portion formed at one terminal end of the base portion; a first sheet Including a plurality of electrically conductive tracks respectively formed on both surfaces surrounding at least a portion of an outer circumferential surface of the base portion; a second sheet surrounding at least a portion of the first sheet and having hardness; and a coating layer configured to planarize a stepped surface formed by a stacked structure including the heating unit, the first sheet, and the second sheet.

In the heater described above, the coating layer includes a heat resistant composition.

In the heater described above, the plurality of electrically conductive tracks include a first electrically conductive track formed on a first surface of the both surfaces of the first sheet and having a resistance temperature coefficient characteristic used for detecting a temperature of the heating unit; and a second electrically conductive track formed on a second surface of the both surfaces of the first sheet and being configured to heat the heating unit as a current flows therein.

According to another aspect of the present disclosure, there is provided an aerosol generating system including a holder configured to generate aerosol by heating an inserted cigarette when a cigarette is inserted; and a cradle Including an inner space for accommodating the holder, wherein the holder is tilted together with the inner space, such that the cigarette is insertable into the holder while the holder is accommodated in the inner space, wherein the holder cumulatively monitors a smoking pattern in a first state in which the holder is tilted in the cradle and a second state in which the holder is separated from the cradle and determines whether the cumulatively monitored smoking pattern satisfies a smoking restriction condition.

In the above-described aerosol generating system, the holder accumulates a smoking pattern monitored in the second state to a smoking pattern monitored in the first state when smoking is performed in the first state and subsequently performed in the second state later, and the holder controls the heater provided in the holder to stop heating the inserted cigarette when the accumulated smoking pattern satisfies the smoking restriction condition.

In the above-described aerosol generating system, the holder accumulates a smoking pattern monitored in the first state to a smoking pattern monitored in the second state when smoking is performed in the second state and subsequently performed in the first state later, and the holder controls the heater provided in the holder to stop heating the inserted cigarette when the accumulated smoking pattern satisfies the smoking restriction condition.

According to another aspect of the present disclosure, there is provided an aerosol generating apparatus including a casing; a hollow protruding tube protruding from a first end of the casing and Including an opening opened to the outside; a heater Installed in the casing, such that an end portion thereof is positioned inside the protruding tube, and configured generate heat when an electric signal is applied; and an accommodating portion, which includes a sidewall forming an accommodating path for accommodating a cigarette; an insertion hole opened to the outside at one end of the accommodating path for insertion of the cigarette thereinto; and a bottom wall configured to close the other end of the accommodating path and including a heater hole through which the end portion of the heater passes, wherein the accommodating portion is insertable into the protruding tube or separable from the protruding tube.

The aerosol generating apparatus described above further includes a cover, which comprises an outer hole capable of exposing the insertion hole of the accommodating portion to the outside, is attachable to a first end portion of the casing to cover the accommodating portion, and is removable from the casing.

In the above-described aerosol generating apparatus, an outside air introduction gap that allows the air outside the cover to flow into the cover is formed at a portion where the cover and the casing are attached to each other, the accommodating portion further includes an outer wall surrounding the sidewall and apart from the sidewall outwardly in the radial direction of the sidewall, the accommodating portion and the protruding tube are coupled with each other by inserting the protruding tube between the outer wall and the sidewall, an air Introducing gap is formed in a portion at which the outer wall of the accommodating portion and the protruding tube are attached to each other to allow the air outside the accommodating portion to flow into the accommodating portion, and the protruding tube further Includes an air hole through which the air passes toward an end portion of the cigarette accommodated in the accommodating portion.

According to another aspect of the present disclosure, there is provided an aerosol-generating article for generating aerosol in association with an aerosol generating apparatus, the aerosol-generating article including a tobacco rod; and a cooling structure fabricated by weaving at least one fiber bundle.

In the above-described aerosol-generating article, the fiber bundle is fabricated by using a biodegradable polymer material, and the biodegradable polymeric material includes at least one of polylactic acid (PLA), polyhydroxybutyrate (PHB), cellulose acetate, poly-epsilon-caprolactone (PCL), polyglycolic acid (PGA), polyhydroxyalkanoate (PHAs), and starch-based thermoplastic resins.

In the above-described aerosol-generating article, the fiber bundle is fabricated by weaving at least one fiber strand.

MODE OF DISCLOSURE

With respect to the terms in the various embodiments of the present disclosure, the general terms which are currently and widely used are selected in consideration of functions of structural elements in the various embodiments of the present disclosure. However, meanings of the terms may be changed according to intention, a judicial precedent, appearance of a new technology, and the like. In addition, in certain cases, a term which is not commonly used may be selected. In such a case, the meaning of the term will be described in detail at the corresponding part in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, exemplary embodiments of the present disclosure will be described in detail with reference to the accompanying drawings. The disclosure may, however, be embodied in many different forms and should not be construed as limited to the embodiments set forth herein.

Hereinafter, embodiments of the present disclosure will be described in detail with reference to the drawings.

FIG. 1 is a block diagram showing an example of an aerosol generating apparatus.

Referring to FIG. 1, an aerosol generating apparatus 1 (hereinafter referred to as a 'holder') includes a battery 110, a control unit 120, and a heater 130. The holder 1 also includes an inner space formed by a casing 140. A cigarette may be inserted into the inner space of the holder 1.

Only components associated with the present embodiment are shown in the holder 1 shown in FIG. 1. Therefore, it will be understood by one of ordinary skill in the art that general components other than the components shown in FIG. 1 may be further included in the holder 1.

When a cigarette is inserted into the holder 1, the holder 1 heats the heater 130. The temperature of an aerosol generating material in the cigarette is raised by the heated heater 130, and thus aerosol is generated. The generated aerosol is delivered to a user through a cigarette filter. However, even when a cigarette is not inserted into the holder 1, the holder 1 may heat the heater 130.

The casing 140 may be detached from the holder 1. For example, when a user rotates the casing 140 clockwise or counterclockwise, the casing 140 may be detached from the holder 1.

The diameter of a hole formed by a terminal end 141 of the casing 140 may be smaller than the diameter of a space formed by the casing 140 and the heater 130.

In this case, the hole may serve as a guide for a cigarette inserted into the holder 1.

The battery 110 supplies power used for the holder 1 to operate. For example, the battery 110 may supply power for heating the heater 130 and supply power for operating the control unit 120. In addition, the battery 110 may supply power for operating a display, a sensor, a motor, and the like installed in the holder 1.

The battery 110 may be a lithium iron phosphate ($LiFePO_4$) battery, but is not limited to the example described above. For example, the battery 110 may be a lithium cobalt oxide ($LiCoO_2$) battery, a lithium titanate battery, etc.

Also, the battery 110 may have a cylindrical shape having a diameter of 10 mm and a length of 37 mm, but is not limited thereto. The capacity of the battery 110 may be 120 mAh or more, and the battery 110 may be a rechargeable battery or a disposable battery. For example, when the battery 110 is rechargeable, the charging rate (C-rate) of the battery 110 may be 10 C and the discharging rate (C-rate) may be 16 C to 20 C. However, the present disclosure is not limited thereto. Also, for stable use, the battery 110 may be manufactured, such that 80% or more of the total capacity may be ensured even when charging/discharging are performed 8000 times.

Here, it may be determined whether the battery 110 is fully charged or completely discharged based on a level of power stored in the battery 110 as compared to the entire capacity of the battery 110. For example, when power stored in the battery 110 is equal to or more than 95% of the total capacity, it may be determined that the battery 110 is fully charged. Furthermore, when power stored in the battery 110 is 10% or less of the total capacity, it may be determined that the battery 110 is completely discharged. However, the criteria for determining whether the battery 110 is fully charged or completely discharged are not limited to the above examples.

The heater 130 is heated by power supplied from the battery 110. When a cigarette is inserted into the holder 1, the heater 130 is located inside the cigarette. Therefore, the heated heater 130 may raise the temperature of an aerosol generating material in the cigarette.

The shape of the heater 130 may be a combination of a cylindrical shape and a conical shape. The diameter of the heater 130 may be appropriately selected within the range from 2 mm to 3 mm. Preferably, the heater 130 may be fabricated to have a diameter of 2.15 mm, but is not limited thereto. In addition, the heater 130 may have a suitable length within the range from 20 mm to 30 mm. Preferably, the heater 130 may be fabricated to have a length of 19 mm, but is not limited thereto. Also, a terminal end 131 of the heater 130 may be formed to have an acute angle, but is not limited thereto. In other words, the heater 130 may have any shape as long as the heater 130 may be inserted into the cigarette. In addition, only a portion of the heater 130 may be heated. For example, assuming that the length of the heater 130 is 19 mm, only 12 mm from the terminal end 131 of the heater 130 may be heated, and the remaining portion of the heater 130 may not be heated.

The heater 130 may be an electro-resistive heater. For example, the heater 130 includes an electrically conductive track, and the heater 130 may be heated as a current flows through the electrically conductive track.

For stable use, the heater 130 may be supplied with power according to the specifications of 3.2 V, 2.4 A, and 8 W, but is not limited thereto. For example, when power is supplied to the heater 130, the surface temperature of the heater 130 may rise to 400° C. or higher. The surface temperature of the heater 130 may rise to about 350° C. before 15 seconds after the power supply to the heater 130 starts.

Hereinafter, the structure of the heater 130 will be described in detail with reference to FIGS. 2 to 5.

Figure 2:
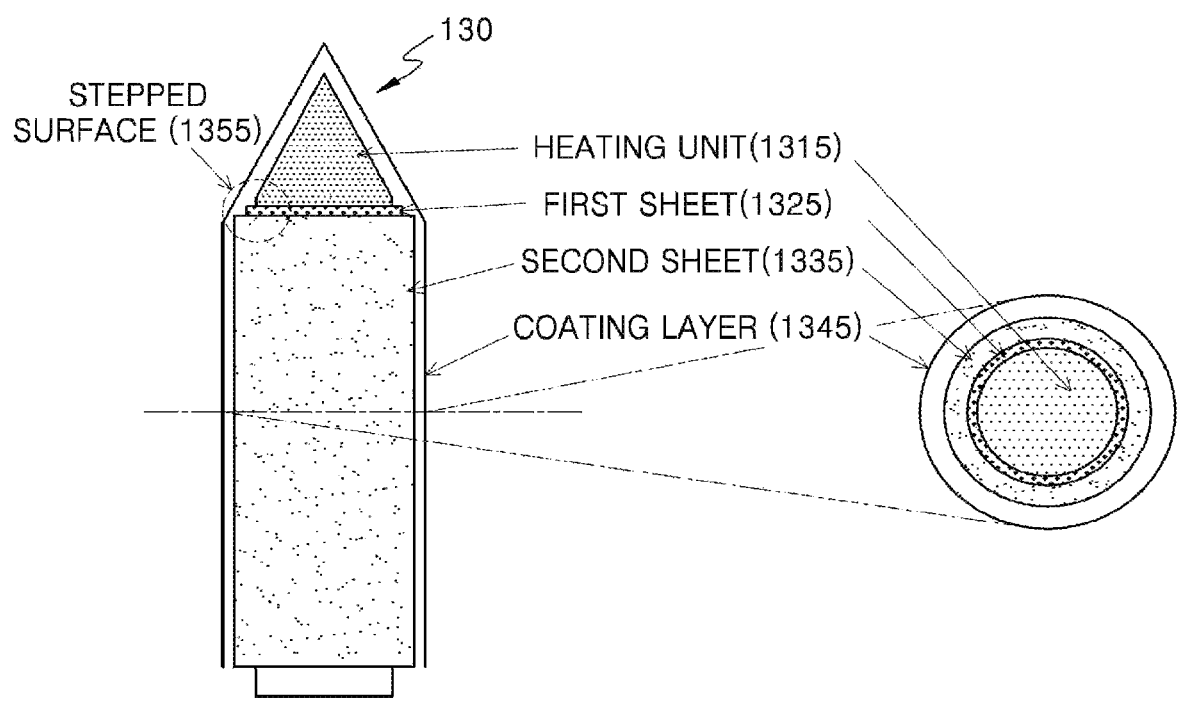
FIG. 2 is a diagram for describing an example of a heater.

FIG. 2 is a diagram for describing an example of a heater.

Referring to FIG. 2, the heater 130 may include a heating unit 1315, a first sheet 1325 surrounding a portion of the heating unit 1315, a second sheet 1335 protecting the first sheet 1325, and a coating layer 1345.

According to an embodiment, the heating unit 1315 may have a needle-like shape (e.g., a combination of a cylindrical shape and a conical shape). In addition, the heating unit 1315 may include a base portion and a tip portion. For example, the base portion of the heating unit 1315 may be formed to have a cylindrical shape, but is not limited thereto. Also, the tip portion of the heating unit 1315 may be formed at one end of the base portion to facilitate insertion into an aerosol forming material. At this time, the base portion and the tip portion may be formed as a single body. Alternatively, the base portion and the tip portion may be separately fabricated and then adhered to each other.

The heating unit 1315 may include a thermally conductive material. For example, the thermally conductive material may Include ceramic including alumina or zirconia, an anodized metal, a coated metal, polyimide (PI), etc., but is not limited thereto.

According to an embodiment, the first sheet 1325 may surround at least a portion of the heating unit 1315. For example, the first sheet 1325 may surround at least a portion of the outer circumferential surface of the base portion of the heater 130. Electrically conductive tracks may be formed on both sides of first sheet 1325.

Also, a first electrically conductive track formed on one of both sides of the first sheet 1325 may receive power from a battery. As a current flows through the first electrically conductive track, the temperature of the first electrically conductive track may rise. Also, as the temperature of the first electrically conductive track rises, heat is transferred to the heating unit 1315 adjacent to the first electrically conductive track, and thus the heating unit 1315 may be heated.

Depending on power consumption of a resistor of the first electrically conductive track, the heating temperature for the first electrically conductive track may be determined. Also, based on power consumption of the resistor of the first electrically conductive track, the resistance value of the first electrically conductive track may be set.

For example, the resistance value of the first electrically conductive track may be between 0.5 ohms and 1.2 ohms at a room temperature of 25° C., but is not limited thereto. At this time, the resistance value of the first electrically conductive track may be set based on the material, the length, the width, the thickness, and the pattern of the first electrically conductive track.

The Internal resistance of the first electrically conductive track may increase as the temperature thereof rises, due to the resistive temperature coefficient characteristics. For example, the temperature of the first electrically conductive track may be proportional to the magnitude of the resistance of the first electrically conductive track in a predetermined temperature section.

For example, a predetermined voltage may be applied to the first electrically conductive track, and a current flowing through the first electrically conductive track may be measured by a current sensor. In addition, the resistance of the first electrically conductive track may be calculated based on a ratio between the measured current to the applied voltage. Based on the calculated resistance, the temperature of the first electrically conductive track or the heating unit 1315 may be estimated, according to the resistance temperature coefficient characteristic of the first electrically conductive track.

For example, the first electrically conductive track may Include tungsten, gold, platinum, silver copper, nickel palladium, or a combination thereof. Also, the first electrically conductive track may be doped with a suitable dopant and may include an alloy.

One or both surfaces of the first sheet 1325 may Include a second electrically conductive track, which has a resistance temperature coefficient characteristic and is used to detect the temperature of the heating unit 1315. The internal resistance of the second electrically conductive track may Increase as the temperature rises, according to the resistive temperature coefficient characteristics. For example, the temperature of the second electrically conductive track may be proportional to the magnitude of the resistance of the second electrically conductive track in a predetermined temperature section.

The second electrically conductive track may be disposed adjacent to the heating unit 1315. Accordingly, when the temperature of the heating unit 1315 rises, the temperature of the second electrically conductive track adjacent thereto may also rise. A predetermined voltage may be applied to the second electrically conductive track, and a current flowing through the second electrically conductive track may be measured through a current detector. In addition, the resistance of the second electrically conductive track may be determined based on a ratio between the measured current to the applied voltage. Based on the determined resistance, the temperature of the heating unit 1315 may be determined, according to the resistance temperature coefficient characteristic of the second electrically conductive track.

Depending on the temperature of the second electrically conductive track, the resistance value of the second electrically conductive track may change. Therefore, based on the change of the resistance value of the second electrically conductive track, the temperature change of the second electrically conductive track may be measured. For example, the resistance value of the second electrically conductive track may be between 7 ohms and 18 ohms at a room temperature of 25° C., but Is not limited thereto. At this time, the resistance value of the second electrically conductive track may be set based on the material, the length, the width, the thickness, and the pattern of the second electrically conductive track.

For example, the second electrically conductive track may include tungsten, gold, platinum, silver copper, nickel palladium, or a combination thereof. Also, the second electrically conductive track may be doped with a suitable dopant or may include an alloy.

The first electrically conductive track may be connected to a battery through an electrical connecting portion. As described above, as power is supplied from the battery, the temperature of the first electrically conductive track may rise.

The second electrically conductive track may include an electrical connecting portion to which a DC voltage is applied. The electrical connecting portion of the second electrically conductive track is separated from the electrical connecting portion of the first electrically conductive track. Also, when a DC voltage applied to the second electrically conductive track is constant, the magnitude of a current flowing through the second electrically conductive track may be determined based on the resistance of the second electrically conductive track.

The second electrically conductive track may be connected to an operating amplifier (OP Amp). The OP Amp includes a power supply unit that receives DC power from the outside, an input unit that is electrically connected to the second electrically conductive track and receives a DC voltage and/or a current, and an output unit that outputs a signal based on the DC voltage and/or the current applied to the input unit.

The OP Amp may receive a DC voltage through the power supply unit. Also, the OP Amp may receive a DC voltage through the input unit. At this time, the magnitude of the DC voltage applied through the input unit of the OP Amp and the magnitude of the DC voltage applied through the power supply unit of the OP Amp may be the same. Also, the DC voltage applied to the input unit of the OP Amp may be equal to the DC voltage applied to the electrically connecting portion of the second electrically conductive track.

The electrical connecting portion of the second electrically conductive track and the input unit of the OP Amp may be separated from the electrical connecting portion of the first electrically conductive track.

As the temperature of the second electrically conductive track changes, the resistance value of the second electrically conductive track may change. Thus, the second electrically conductive track functions as a variable resistor that is controlled by the temperature as a control variable and, as the resistance value of the second electrically conductive track changes, a current flowing into the input unit of the OP Amp electrically connected to the second electrically conductive track changes. As the resistance of the second electrically conductive track increases, a current flowing into the input unit of the OP Amp electrically connected to the second electrically conductive track is reduced. At this time, even when the resistance value of the second electrically conductive track is changed, the DC voltage applied to the input unit of the OP Amp may be constant.

As the current flowing into the input unit of the OP Amp changes, a voltage and/or a current of a signal output from the output unit of the OP Amp may change. For example, as an input current of the OP Amp increases, an output voltage of the OP Amp may increase. In another example, as the input current of the OP Amp increases, the output voltage of the OP Amp may decrease.

A relationship between the temperature and the resistance value of the second electrically conductive track, a relationship between the resistance value of the second electrically conductive track and the input current applied to the OP Amp, and a relationship between the input current and the output voltage of the OP Amp when a constant DC voltage is applied to the input unit of the OP Amp may be experimentally obtained or set. Therefore, the output voltage and/or a change of the output voltage of the OP Amp may be measured to detect a change in temperature and/or a change of temperature of the second electrically conductive track.

For example, the OP Amp may have a characteristic that the voltage of the output unit of the OP Amp increases as the input current flowing into the input unit increases. In this case, the temperature of a heater rises as power is supplied to the first electroconductive track. As a result, the temperature of the second electrically conductive track rises. At this time, since the resistance value of the second electrically conductive track increases, the magnitude of the input current applied to the input unit of the OP Amp may be reduced. Therefore, the voltage at the output unit of the OP Amp decreases. On the contrary, the voltage at the output unit of the OP Amp increases as power supply to the first electrically conductive track is interrupted or power supplied to the first electrically conductive track decreases and the temperature of a heater decreases.

In another example, the OP Amp may have a characteristic that the voltage of the output unit of the OP Amp decreases as the input current flowing into the input unit increases. In this case, the temperature of a heater rises as power is supplied to the first electroconductive track. As a result, the temperature of the second electrically conductive track rises. At this time, since the resistance value of the second electrically conductive track increases, the magnitude of the input current applied to the input unit of the OP Amp may be reduced. Therefore, the voltage at the output unit of the OP Amp Increases. On the contrary, the voltage at the output unit of the OP Amp decreases as power supply to the first electrically conductive track is interrupted or power supplied to the first electrically conductive track decreases and the temperature of a heater decreases.

The output unit of the OP Amp may be connected to a processor. For example, the processor may be an micro controller unit (MCU). The processor may detect the temperature of the second electrically conductive track or a heating unit based on the output voltage of the OP Amp. The processor may also adjust a supply voltage supplied to the first electrically conductive track based on the temperature of the heating unit.

According to an embodiment, the first electrically conductive track and the second electrically conductive track may be formed on both sides of the first sheet 1325, respectively. For example, the first electrically conductive track may be included on one side of the first sheet 1325 in contact with the heating unit 1315, and the second electrically conductive track may be included on the other side. In another example, the second electrically conductive track may be included on one side of the first sheet 1325 in contact with the heating unit 1315, and the first electrically conductive track may be included on the other side.

According to another embodiment, the first electrically conductive track and the second electrically conductive track may be included on the same side of the both sides of the first sheet 1325. For example, both the first electrically conductive track and the second electrically conductive track may be included on one of the both side of the first sheet 1325 in contact with the heating unit 1315. In another example, both the first electrically conductive track and the second electrically conductive track may be included on one of the both side of the first sheet 1325 not in contact with the heating unit 1315.

For example, the first sheet 1325 may be a green sheet including a ceramic composite material. Here, the ceramic may include, but not limited to, compounds like alumina and zirconia.

According to an embodiment, the second sheet 1335 may surround at least a portion of the first sheet 1325. Also, the second sheet 1335 may have rigidity.

Therefore, the second sheet 1335 protects the first sheet 1325 and electrically conductive tracks when the heater 130 is inserted into an aerosol-forming material.

For example, the second sheet 1335 may be a green sheet including a ceramic composite material. Here, the ceramic may include, but not limited to, compounds like alumina and zirconia.

the second sheet 1335 may be coated with glaze to facilitate insertion of the heater 130 into a cigarette 3 and to improve the durability of the heater 130. As the second sheet 1335 is coated with glaze, the rigidity of the second sheet 1335 may be increased.

Each of the heating unit 1315, the first sheet 1325, and the second sheet 1335 may selectively include a material in the same material group, e.g., ceramics that are compounds like alumina and zirconia.

Also, each of the first electrically conductive track and the second electrically conductive track may selectively include a material in the same material group, e.g., tungsten, gold, platinum, silver copper, nickel palladium, or a combination thereof. Here, even when the first electrically conductive track and the second electrically conductive track include the same material, the resistance values of the first electrically conductive track and the second electrically conductive track may be different from each other due to differences in lengths, widths, or patterns of the first electrically conductive track and the second electrically conductive track.

According to an embodiment, the first electrically conductive track for heating the heating unit 1315 may be included in the heating unit 1315, the first sheet 1325, or the second sheet 1335. Alternatively, a plurality of electrically conductive tracks (e.g., first electrically conductive tracks) for heating the heating unit 1315 may be included in at least one of the heating unit 1315, the first sheet 1325, and the second sheet 1335.

According to an embodiment, the second electrically conductive track for detecting the temperature of the heating unit 1315 may be included in the heating unit 1315, the first sheet 1325, or the second sheet 1335. Alternatively, a plurality of electrically conductive tracks (e.g., second electrically conductive tracks) for detecting the temperature of the heating unit 1315 may be included in at least one of the heating unit 1315, the first sheet 1325, and the second sheet 1335.

According to an embodiment, the first electrically conductive track for heating the heating unit 1315 and the second electrically conductive track for detecting the temperature of the heating unit 1315 may be included in the same component from among the heating unit 1315, the first sheet 1325, and the second sheet 1335. Alternatively, the first electrically conductive track for heating the heating unit 1315 and the second electrically conductive track for detecting the temperature of the heating unit 1315 may be Included in different components from among the heating unit 1315, the first sheet 1325, and the second sheet 1335, respectively.

As the heater 130 is provided with a coating layer 1345, a stepped surface formed by a stacked structure including the heating unit 1315, the first sheet 1325, and the second sheet 1335 may be planarized. For example, a stepped surface 1355 may be formed because the edge portion of the first sheet 1325 and the edge portion of the second sheet 1335 do not form a continuos surface or due to the thicknesses of the first sheet 1325 and the second sheet 1335. For example, due to the stepped surface 1355, friction may increase when the heater 130 is inserted into an aerosol forming material. In addition, deposition of a deposition material or residues from the aerosol-forming material on the stepped surface 1355 contaminates the heater 130, thereby deteriorating the performance (e.g., the thermal conductivity) of the heater 130. Therefore, the coating layer 1345 may be formed on the outer surface of the heater 130 to planarize the stepped surface 1355.

The outer surface of the heater 130, which is formed by the coating layer 1345, may include a tip portion of the coating layer 1345 corresponding to a tip portion of the heating unit 1315, a base portion of heating unit 1315, and a base portion of the coating layer 1345 corresponding to the first sheet 1325 and the second sheet 1335. At this time, a portion of the coating layer 1345 extending from the tip portion of the coating layer 1345 to the base portion of the coating layer 1345 may have a smooth outer surface without the stepped surface 1355 or a concavo-convex portion.

The coating layer 1345 may include a heat resistant composition. For example, the coating layer 1345 may include, but is not limited to, a single coating layer of a glass coating layer, a Teflon coating layer, and a molar coating layer. Also, the coating layer 1345 may include, but is not limited to, a composite coating layer composed of a combination of two or more of a glass coating layer, a Teflon coating layer, and a molar coating layer.

Figure 3:
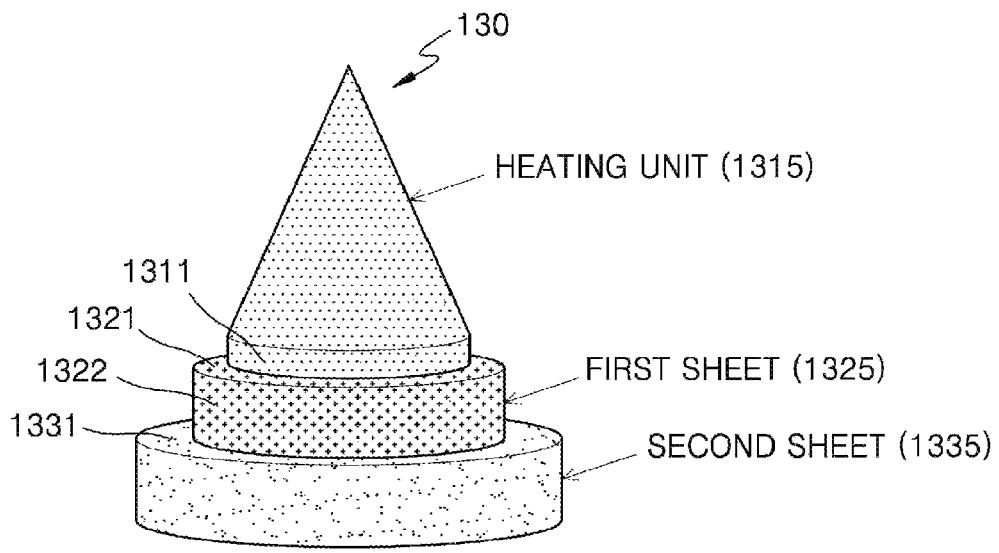
FIG. 3 is a diagram for describing an example of the stepped surface shown in FIG. 2.

FIG. 3 is a diagram for describing an example of the stepped surface shown in FIG. 2.

Referring to FIG. 3, the stepped surface 1355 may be formed by the base portion of the heater 130 and the first sheet 1325 and the second sheet 1335 surrounding the base portion.

For example, a terrace 1321 may be formed by the thickness of the first sheet 1325. Furthermore, the terrace 1331 may be formed by the thickness of the second sheet 1335.

Furthermore, a step 1311 may be formed because the boundary between the tip portion and the base portion of a heating unit does not coincide with the edge portion of the first sheet 1325. Furthermore, since the edge portion of the first sheet 1325 does not coincide with the edge portion of the second sheet 1335, a step 1322 may be formed.

At this time, deposition or debris of an aerosol forming material may be piled in the space formed by the stepped surface 1355, and thus the heater may be contaminated. As described above with reference to FIG. 2, the coating layer 1345 may fill a gap formed by the stepped surface 1355 to planarize the stepped surface 1355.

Figure 4:
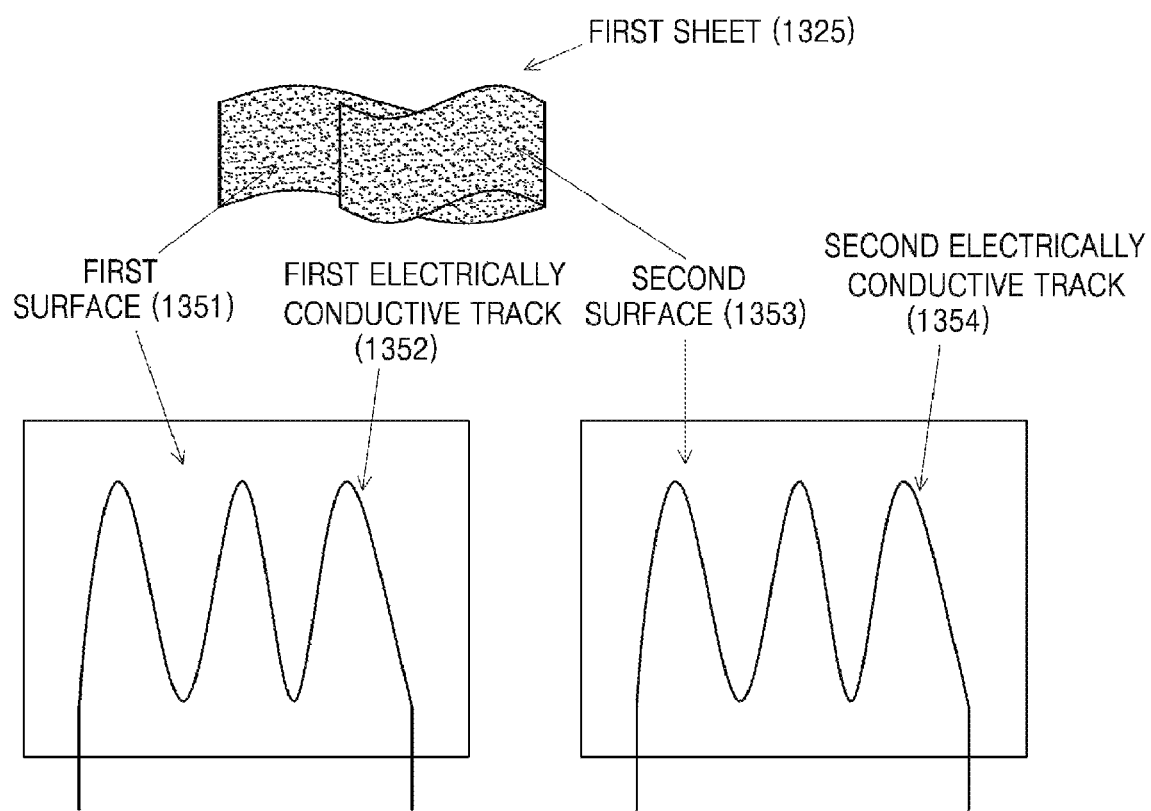
FIG. 4 is a diagram for describing an example of electrically conductive tracks.

FIG. 4 is a diagram for describing an example of electrically conductive tracks.

A first surface 1351 of the first sheet 225 may include a first electrically conductive track 1352 and a second surface 1353 may include a second electrically conductive track 1354.

The first electrically conductive track 1352 may heat the heating unit 1315 of the heater 130 as a current flows therein. An electrically conductive track may be connected to an external power source via a connection. Also, as power is supplied to the electrically conductive track from an external power source, a current may flow in the electrically conductive track. Therefore, the electrically conductive track may generate heat and transfer the heat to a nearby heating unit 1315, thereby heating the heating unit 1315.

For example, the first electrically conductive track 1352 of the first surface 1351 may be formed in various patterns, such as a curved shape and a mesh shape.

A second surface 1353 of the first sheet 1325 may include a second electrically conductive track 1354, which has a resistance temperature coefficient characteristic and is used to detect the temperature of the heating unit 1315. As described above, the internal resistance of the second electrically conductive track 1354 may increase as the temperature rises, according to the resistance temperature coefficient characteristic. For example, the temperature of the second electrically conductive track 1354 may be proportional to the magnitude of the resistance of the second electrically conductive track 1354 in a predetermined temperature section.

The second electrically conductive track 1354 may be disposed adjacent to the heating unit 1315. For example, heat may be transferred from the heating unit 1315 to the second electrically conductive track 1354 as the heating unit 1315 is heated. When the temperature of the heating unit 1315 rises, the temperature of the second electrically conductive track 1354 also rises, and the resistance of the second electrically conductive track 1354 may increase. On the contrary, when the temperature of the heating unit 1315 decreases, as the temperature of the second electrically conductive track 1354 also decreases, the resistance of the second electrically conductive track 1354 may decrease.

The second electrically conductive track 1354 may be connected to the control unit through a connection. For example, the second electrically conductive track 1354 may be connected to a processor that controls the temperature of the heating unit 1315. For example, the second electrically conductive track 1354 may be connected to the control unit. By using the relationship between the resistance and the temperature of the second electrically conductive track 1354, the resistance of the second electrically conductive track 1354 is determined from a voltage and a current of the second electrically conductive track 1354, and the temperature of the heating unit 1315 may be determined based on the determined resistance. Based on the temperature determined by using the second electrically conductive track 1354, power supplied to the first electrically conductive track 1352 may be adjusted.

The second electrically conductive track 1354 may be disposed adjacent to the heating unit 1315 to receive the heat from the heating unit 1315. Also, the first electrically conductive track 1352 of the second surface 1353 may be formed in various patterns, such as a curved shape and a mesh shape.

The first surface 1351 including the first electrically conductive track 1352 may be one of surfaces of the first sheet 1325 that contacts the heating unit 1315 and the second surface including the second electro-1353 may not be the other one of the surfaces of the first sheet 1325 that does not contact the heating unit 1315. On the contrary, the second surface 1353 including the second electrically conductive track 1354 may be one surface that contacts the heating unit 1315, and the first surface 1351 including the first electrically conductive track 1352 may be the other surface that does not contact the heating unit 1315.

FIG. 4 is a diagram for describing an embodiment in which the first electrically conductive track 1352 and the second electrically conductive track 1354 are disposed on the respective surfaces of the first sheet 1325. However, as described above, the first electrically conductive track 1352 and the second electrically conductive track 1354 may be formed on the same surface of the first sheet 1325.

Figure 5:
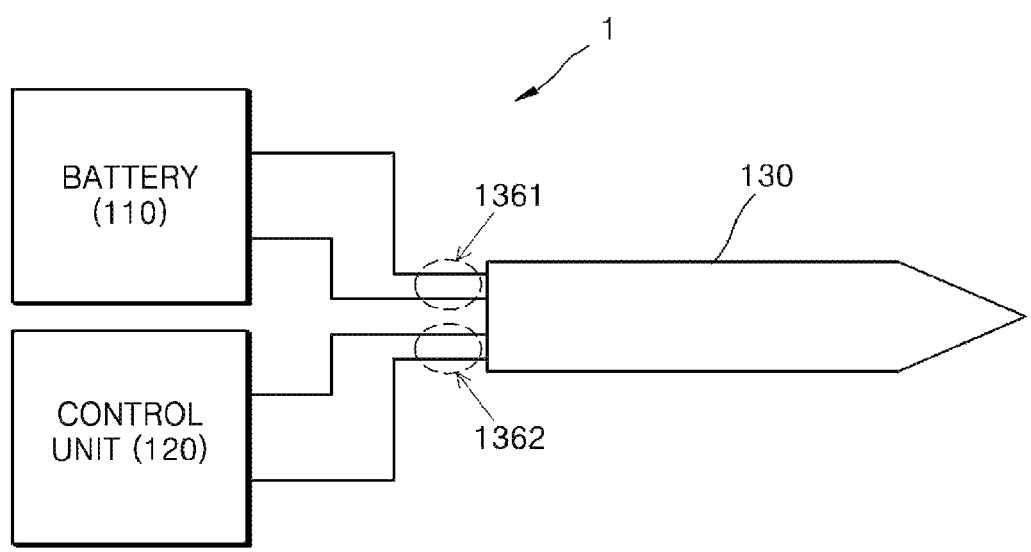
FIG. 5 is a diagram for describing an example in which the heater, the battery, and the control unit shown in FIG. 1 are connected.

FIG. 5 is a diagram for describing an example in which the heater, the battery, and the control unit shown in FIG. 1 are connected.

Referring to FIG. 5, the holder 1 may include the heater 130, the battery 110, and the control unit 120. Since the heater 130 of FIG. 5 is the same as the heater 130 described above with reference to FIGS. 1 to 4, detailed descriptions of the heater 130 will be omitted.

The battery 110 may be connected to the heater 130 via a first connector 1361. For example, the battery 110 may be electrically connected to a first electrically conductive track of a first sheet of the heater 130 and supply power to the first electrically conductive track.

The battery 110 may include a power source and a circuit for supplying power. For example, the battery 110 may provide a supply voltage to the first electrically conductive track via the first connector 1361. The supply voltage may be a DC or AC voltage, a pulse voltage having a constant period, or a pulse voltage having a fluctuating period, but is not limited thereto.

The control unit 120 may include a processor. For example, the processor may be, but is not limited to, an MCU.

The control unit 120 may be connected to the heater 130 via a second connector 1362. For example, the control unit 120 may be electrically connected to the second electrically conductive track of the first sheet of the heater 130 and determine the temperature of the heater 130. The control unit 120 may also adjust the temperature of the heater 130 based on the determined temperature of the heater 130.

For example, the control unit 120 may determine whether to adjust the temperature of the heater 130 based on the determined temperature of the heater 130. The control unit 120 may adjust power supplied from the battery 110 to the heater 130 based on the determination of whether to adjust the temperature of the heater 130. For example, the control unit 120 may adjust the magnitude or the period of a pulse voltage supplied from the battery 110 to the heater 130.

The control unit 120 according to an embodiment may Include an OP Amp.

The second electrically conductive track may be connected to the OP Amp via the second connector 1362. The OP Amp includes a power supply unit that receives DC power from the outside, an input unit that is electrically connected to the second electrically conductive track and receives a DC voltage and/or a current, and an output unit that outputs an electric signal based on the DC voltage and/or the current applied to the input unit.

The OP Amp may receive a DC voltage through the power supply unit. Also, the OP Amp may receive a DC voltage through the input unit. At this time, the magnitude of the DC voltage applied through the input unit of the OP Amp and the magnitude of the DC voltage applied through the power supply unit of the OP Amp may be the same. Also, the DC voltage applied to the input unit of the OP Amp may be equal to the DC voltage applied to the second connector 1362 of the second electrically conductive track.

The second connector 1382 of the second electrically conductive track and the input unit of the OP Amp may be separated from the first connector 1361 of the first electrically conductive track.

As the temperature of the second electrically conductive track changes, the resistance value of the second electrically conductive track may change. Thus, the second electrically conductive track functions as a variable resistor that is controlled by the temperature as a control variable and, as the resistance value of the second electrically conductive track changes, a current flowing into the input unit of the OP Amp electrically connected to the second electrically conductive track changes. As the resistance of the second electrically conductive track increases, a current flowing into the input unit of the OP Amp electrically connected to the second electrically conductive track is reduced. At this time, even when the resistance value of the second electrically conductive track is changed, the DC voltage applied to the input unit of the OP Amp may be constant.

As the current flowing into the input unit of the OP Amp changes, a voltage and/or a current of a signal output from the output unit of the OP Amp may change. For example, as an input current of the OP Amp Increases, an output voltage of the OP Amp may increase. In another example, as the input current of the OP Amp increases, the output voltage of the OP Amp may decrease.

A relationship between the temperature and the resistance value of the second electrically conductive track, a relationship between the resistance value of the second electrically conductive track and the input current applied to the OP Amp, and a relationship between the input current and the output voltage of the OP Amp when a constant DC voltage is applied to the input unit of the OP Amp may be experimentally obtained or set. Therefore, the output voltage and/or a change of the output voltage of the OP Amp may be measured to detect a change in temperature and/or a change of temperature of the second electrically conductive track.

For example, the OP Amp may have a characteristic that the voltage of the output unit of the OP Amp increases as the input current flowing into the input unit increases. In this case, the temperature of a heater rises as power is supplied to the first electroconductive track. As a result, the temperature of the second electrically conductive track rises. At this time, since the resistance value of the second electrically conductive track increases, the magnitude of the input current applied to the input unit of the OP Amp may be reduced. Therefore, the voltage at the output unit of the OP Amp decreases. On the contrary, the voltage at the output unit of the OP Amp increases as power supply to the first electrically conductive track is interrupted or power supplied to the first electrically conductive track decreases and the temperature of a heater decreases.

In another example, the OP Amp may have a characteristic that the voltage of the output unit of the OP Amp decreases as the input current flowing into the input unit increases. In this case, the temperature of a heater rises as power is supplied to the first electroconductive track. As a result, the temperature of the second electrically conductive track rises. At this time, since the resistance value of the second electrically conductive track increases, the magnitude of the input current applied to the input unit of the OP Amp may be reduced. Therefore, the voltage at the output unit of the OP Amp increases. On the contrary, the voltage at the output unit of the OP Amp decreases as power supply to the first electrically conductive track is interrupted or power supplied to the first electrically conductive track decreases and the temperature of a heater decreases.

The output unit of the OP Amp may be connected to a processor. The processor may be, for example, an MCU. The processor may detect the temperature of the second electrically conductive track or a heating unit based on the output voltage of the OP Amp. The processor may also adjust a supply voltage supplied to the first electrically conductive track based on the temperature of the heating unit.

Referring back to FIG. 1, the holder 1 may be provided with a separate temperature sensor. Alternatively, the holder 1 may not be provided with a temperature sensing sensor, and the heater 130 may serve as a temperature sensing sensor.

Alternatively, the heater 130 of the holder 1 may function as a temperature sensor, and the holder 1 may further include a temperature sensor. For the heater 130 to function as a temperature sensing sensor, the heater 130 may include at least one electrically conductive track for heating and temperature sensing. The heater 130 may further Include a second electrically conductive track for temperature sensing in addition to the first electrically conductive track for generating heat.

For example, when a voltage applied to the second electrically conductive track and a current flowing through the second electrically conductive track are measured, a resistance R may be determined. At this time, a temperature T of the second electrically conductive track may be determined by Equation 1 below.

$$R = R_0\{1 + \alpha(T - T_0)\} \quad \text{[Equation 1]}$$

In Equation 1, R denotes a current resistance value of the second electrically conductive track, $R_0$ denotes a resistance value at a temperature $T_0$ (e.g., 0° C.), and a denotes a resistance temperature coefficient of the second electrically conductive track. Since conductive materials (e.g., metals) have inherent resistance temperature coefficients, a may be determined in advance according to a conductive material constituting the second electrically conductive track. Therefore, when the resistance R of the second electrically conductive track is determined, the temperature T of the second electrically conductive track may be calculated according to Equation 1.

The heater 130 may include at least one electrically conductive track (a first electrically conductive track and a second electrically conductive track). For example, the heater 130 may Include, but is not limited to, two first electrically conductive tracks and one or two second electrically conductive tracks.

An electrically conductive track include an electro-resistive material. For example, an electrically conductive track may include a metal. In another example, an electrically conductive track may include an electrically conductive ceramic material, a carbon, a metal alloy, or a composite of a ceramic material and a metal.

In addition, the holder 1 may include both an electrically conductive track, which serve as temperature sensing sensors, and a temperature sensing sensor.

The control unit 120 controls the overall operation of the holder 1. Specifically, the control unit 120 controls not only operations of the battery 110 and the heater 130, but also operations of other components included in the holder 1. The control unit 120 may also check the status of each of the components of the holder 1 and determine whether the holder 1 is in an operable state.

The control unit 120 includes at least one processor. A processor may be Implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

For example, the control unit 120 may control the operation of the heater 130. The control unit 120 may control an amount of power supplied to the heater 130 and a time for supplying the power, such that the heater 130 may be heated to a predetermined temperature or maintained at a proper temperature. The control unit 120 may also check the status of the battery 110 (e.g., the remaining amount of the battery 110) and generate a notification signal as occasions demand.

Also, the control unit 120 may check the presence or absence of a user's puff, check the strength of the puff, and count the number of puffs. Also, the control unit 120 may continuously check the time during which the holder 1 is operating. The control unit 120 may also check whether a cradle 2 to be described below is coupled with the holder 1 and control the operation of the holder 1 based on whether the cradle 2 is coupled with or separated from and the holder 1.

Meanwhile, the holder 1 may further include general-purpose components other than the battery 110, the control unit 120, and the heater 130.

For example, the holder 1 may include a display capable of outputting visual information or a motor for outputting tactile information. For example, when a display is included in the holder 1, the control unit 120 may provide a user information about the state of the holder 1 (e.g., availability of the holder, etc.), information about the heater 130 (e.g., start of preheating, progress of preheating, completion of preheating, etc.), information about the battery 110 (e.g., remaining power of the battery 110, availability, etc.), information about resetting of the holder 1 (e.g., reset timing, reset progress, reset completion, etc.), information about cleaning of the holder 1 (e.g., cleaning timing, cleaning progress, cleaning completion, etc.), information about charging of the holder 1 (e.g., need of charging, charging progress, charging completed, etc.), information about puff (e.g., the number of puffs, notification of expected completion of puffs, etc.), or information about safety (e.g., time of use, etc.) via the display. In another example, when a motor is included in the holder 1, the control unit 120 may transmit the above-described Information to a user by generating a vibration signal by using the motor.

The holder 1 may also include a terminal coupled with at least one input device (e.g., a button) and/or the cradle 2 through which a user may control the function of the holder 1. For example, a user may perform various functions by using the input device of the holder 1. By adjusting the number of times a user presses the input device (e.g., once, twice, etc.) or the time during which the input device Is being pressed (e.g., 0.1 second, 0.2 second, etc.), a desired function from among a plurality of functions of the holder 1 may be executed. As a user manipulates the input device, the holder 1 may perform a function of preheating the heater 130, a function of regulating the temperature of the heater 130, a function of cleaning the space in which a cigarette is inserted, a function of checking whether the battery 110 is in an operable state, a function of displaying the remaining power (available power) of the battery 110, a function of resetting the holder 1, etc. However, the functions of the holder 1 are not limited to the examples described above.

For example, the holder 1 may clean the space in which a cigarette is inserted by controlling the heater 130 as follows. For example, the holder 1 may clean the space in which a cigarette is inserted by heating the heater 130 to a sufficiently high temperature. Here, the sufficiently high temperature refers to a temperature suitable for cleaning the space in which a cigarette is inserted. For example, the holder 1 may heat the heater 130 to the highest temperature in a temperature range in which an aerosol may be generated from an inserted cigarette and a temperature range for preheating the heater 130, but the present invention is not limited thereto.

In addition, the holder 1 may maintain the temperature of the heater 130 at a sufficiently high temperature for a predetermined period of time. Here, the predetermined period of time refers to a period of time sufficient for the space in which a cigarette is inserted to be cleaned. For example, the holder 1 may maintain the temperature of the heated heater 130 for a suitable period of time from 10 seconds to 10 minutes, but the present disclosure is not limited thereto. Preferably, the holder 1 may maintain the temperature of the heated heater 130 for a suitable period of time selected within the range from 20 seconds to 1 minute. More preferably, the holder 1 may maintain the temperature of the heated heater 130 for a suitable period of time selected within the range from 20 seconds to 1 minute 30 seconds.

As the holder 1 heats the heater 130 to a sufficiently high temperature and also maintains the temperature of the heated heater 130 for a predetermined period of time, a material deposited on a surface of the heater 130 and/or the spece in which a cigarette is inserted is volatilized, and thus cleaning effect may be obtained.

The holder 1 may also include a puff detecting sensor, a temperature sensing sensor, and/or a cigarette insertion detecting sensor. For example, the puff detecting sensor may be implemented by a common pressure sensor. Alternatively, the holder 1 may detect puffs based on a resistance change of an electrically conductive track included in the heater 130 without a separate puff detecting sensor. Here, the electrically conductive track includes an electrically conductive track for generating heat and/or an electrically conductive track for sensing temperature. Alternatively, the holder 1 may further include a puff detecting sensor separately from detection of puffs using an electrically conductive track included in the heater 130.

The cigarette insertion detecting sensor may be implemented by a common capacitive sensor or a resistance sensor. Also, the holder 1 may be fabricated to have a structure in which the outside air may flow in/out even in the state where the cigarette is inserted.

Figure 6A:
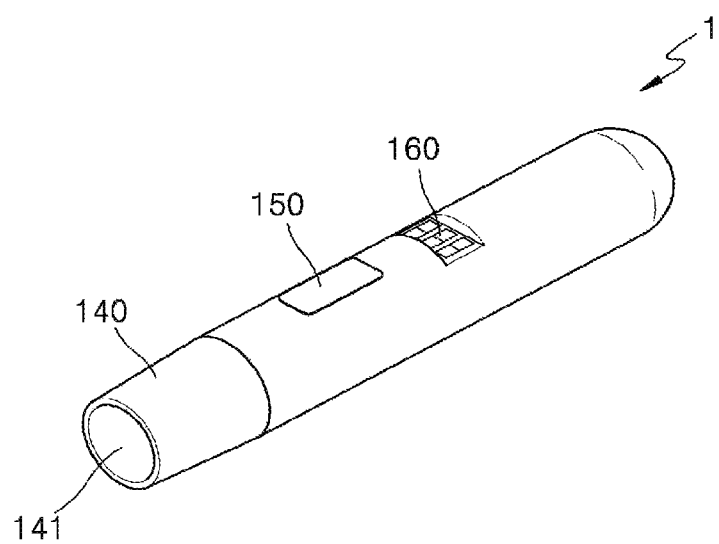
FIGS. 6A and 6B are diagrams showing various views of an example of a holder.
Figure 6B:
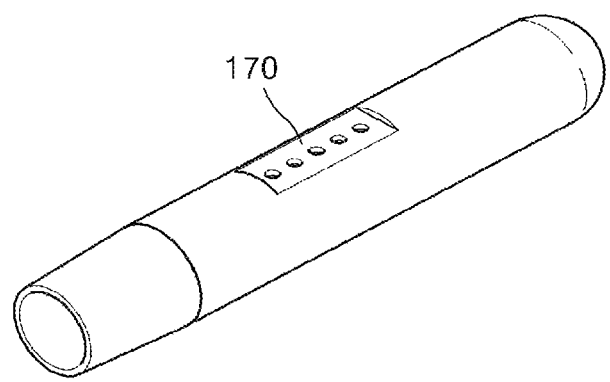

FIGS. 6A and 6B are diagrams showing various views of an example of a holder.

FIG. 6A is a diagram showing an example of the holder 1 viewed in a first direction. As shown in FIG. 6A, the holder 1 may be fabricated to have a cylindrical shape, but the present disclosure is not limited thereto. The casing 140 of the holder 1 may be separated by an action of a user and a cigarette may be Inserted into an terminal end 141 of the casing 140. The holder 1 may also include a button 150 for a user to control the holder 1 and a display 160 for outputting an image.

FIG. 6B is a diagram showing an example of the holder 1 viewed in a second direction. The holder 1 may include a terminal 170 coupled with the cradle 2. As the terminal 170 of the holder 1 is coupled with a terminal 260 of the cradle 2, the battery 110 of the holder 1 may be charged by power supplied by a battery 210 of the cradle 2. Also, the holder 1 may be operated by power supplied from the battery 210 of the cradle 2 through the terminal 170 and the terminal 260 and a communication (transmission/reception of signals) may be performed between the holder 1 and the cradle 2 through the terminal 170 and the terminal 260. For example, the terminal 170 may Include four micro pins, but the present disclosure is not limited thereto.

Figure 7:
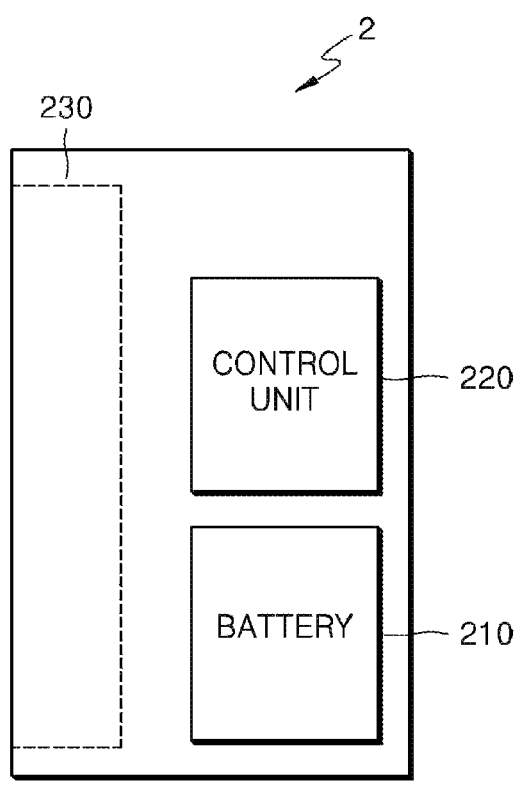
FIG. 7 is a diagram showing an example configuration of a cradle.

FIG. 7 is a diagram showing an example configuration of a cradle.

Referring to FIG. 7, the cradle 2 includes the battery 210 and a control unit 220. The cradle 2 also includes an inner space 230 into which the holder 1 may be inserted. For example, the inner space 230 may be formed on one side of the cradle 2. Therefore, the holder 1 may be inserted and fixed in the cradle 2 even when the cradle 2 does not Include a separate lid.

Only components of the cradle 2 related to the present embodiment are shown in FIG. 7. Therefore, it will be understood by one of ordinary skill in the art that general-purpose components other than the components shown in FIG. 7 may be further included in the cradle 2.

The battery 210 provides power used to operate the cradle 2. In addition, the battery 210 may supply power for charging the battery 110 of the holder 1. For example, when the holder 1 is inserted into the cradle 2 and the terminal 170 of the holder 1 is coupled with the terminal 260 of the cradle 2, the battery 210 of the cradle 2 may supply power to the battery 110 of the holder 1.

Also, when the holder 1 is coupled with the cradle 2, the battery 210 may supply power used for the holder 1 to operate. For example, when the terminal 170 of the holder 1 is coupled with the terminal 260 of the cradle 2, the holder 1 may operate by using power supplied by the battery 210 of the cradle 2 regardless of whether the battery 110 of the holder 1 is discharged or not.

For example, the battery 210 may be a lithium ion battery, but is not limited thereto. The capacity of the battery 210 may be greater than the capacity of the battery 110. For example, the capacity of the battery 210 may be, but is not limited to, 3000 mAh or greater.

The control unit 220 generally controls the overall operation of the cradle 2. The control unit 220 may control the overall operation of all the configurations of the cradle 2. The control unit 220 may also determine whether the holder 1 is coupled with the cradle 2 and control the operation of the cradle 2 according to coupling or separation of the cradle 2 and the holder 1.

For example, when the holder 1 is coupled with the cradle 2, the control unit 220 may supply power of the battery 210 to the holder 1, thereby charging the battery 110 or heating the heater 130. Therefore, even when remaining power of the battery 110 is low, a user may continuously smoke by coupling the holder 1 with the cradle 2.

The control unit 220 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

Meanwhile, the cradle 2 may further include general-purpose components other than the battery 210 and the control unit 220. For example, cradle 2 may include a display capable of outputting visual information. For example, when the cladle 2 includes a display, the control unit 220 generates a signal to be displayed on the display, thereby informing a user information regarding the battery 210 (e.g., the remaining power of the battery 210, availability of the battery 210, etc.), information regarding resetting of the cradle 2 (e.g., reset timing, reset progress, reset completion, etc.), information regarding cleaining of the holder 1 (e.g., cleaning timing, cleaning necessity, cleaining progress, cleaining completion, etc.), information regarding charging of the cradle 2 (e.g., charging necessity, charging progress, charging completion, etc.).

The cradle 2 may also include at least one input device (e.g., a button) for a user to control the function of the cradle 2, a terminal 260 to be coupled with the holder 1, and/or an interface for charging the battery 210 (e.g., an USB port, etc.).

For example, a user may perform various functions by using the input device of the cradle 2. By controlling the number of times that a user presses the input device or a period of time for which the input device is pressed, a desired function from among the plurality of functions of the cradle 2 may be executed. As a user manipulates the input device, the cradle 2 may perform a function of preheating the heater 130, a function of regulating the temperature of the heater 130, a function of cleaning the space in which a cigarette is inserted, a function of checking whether the cradle 2 is in an operable state, a function of displaying the remaining power (available power) of the battery 210 of the cradle 2, a function of resetting the cradle 2, etc. However, the functions of the cradle 2 are not limited to the examples described above.

Figure 8A:
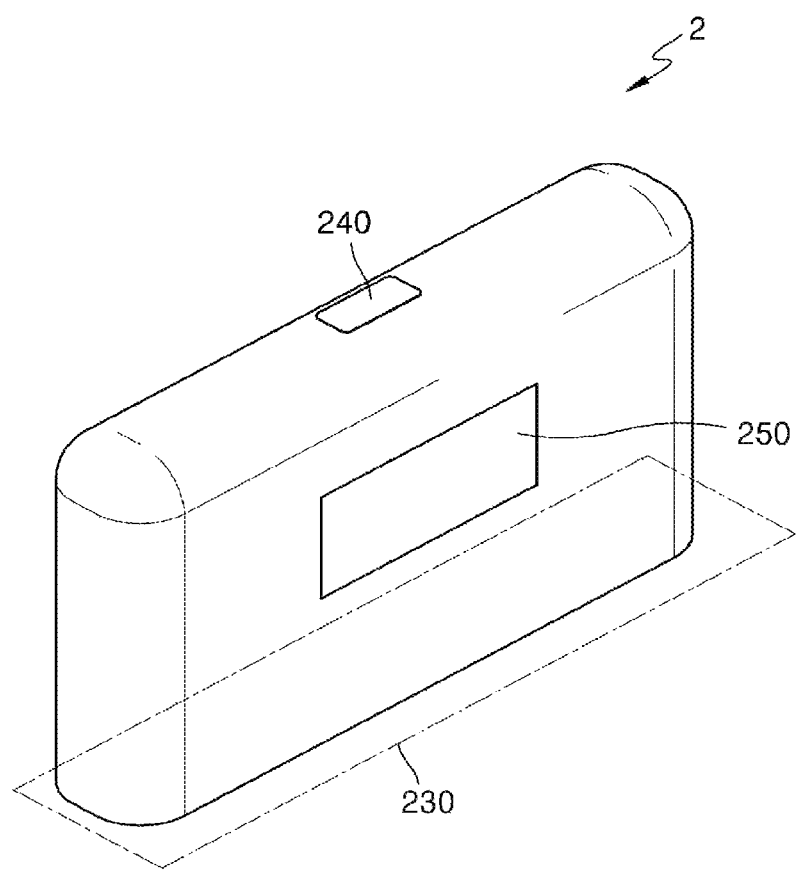
FIGS. 8A and 8B are diagrams showing various views of an example of a cradle.
Figure 8B:
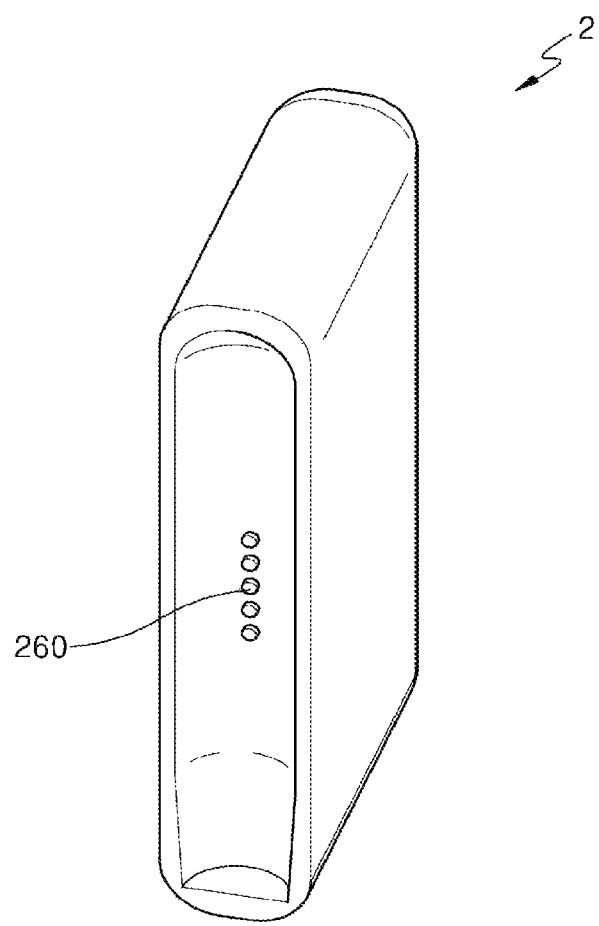

FIGS. 8A and 8B are diagrams showing various views of an example of a cradle.

FIG. 8A is a diagram showing an example of the cradle 2 viewed in a first direction. The inner space 230 into which the holder 1 may be inserted may be formed on one side of the cradle 2. Also, the holder 1 may be inserted and fixed in the cradle 2 even when the cradle 2 does not include a separate fixing unit like a lid. The cradle 2 may also include a button 240 for a user to control the cradle 2 and a display 250 for outputting an image.

FIG. 8B is a diagram showing an example of the cradle 2 viewed in a second direction. The cradle 2 may include a terminal 260 to be coupled with the inserted holder 1. The battery 110 of the holder 1 may be charged by power supplied by the battery 210 of the cradle 2 as the terminal 260 is coupled with the terminal 170 of the holder 1. Also, the holder 1 may be operated by power supplied from the battery 210 of the cradle 2 through the terminal 170 and the terminal 260 and transmission/reception of signals may be performed between the holder 1 and the cradle 2 through the terminal 170 and the terminal 260. For example, the terminal 260 may include four micro pins, but the present disclosure is not limited thereto.

The holder 1 may be inserted into the inner space 230 of the cradle 2, as described above with reference to FIGS. 1 to 8B. The holder 1 may be completely Inserted into the cradle 2 or may be tilted while being inserted into the cradle 2. Hereinafter, examples in which the holder 1 is inserted into the cradle 2 will be described with reference to FIGS. 9 and 10.

Figure 9:
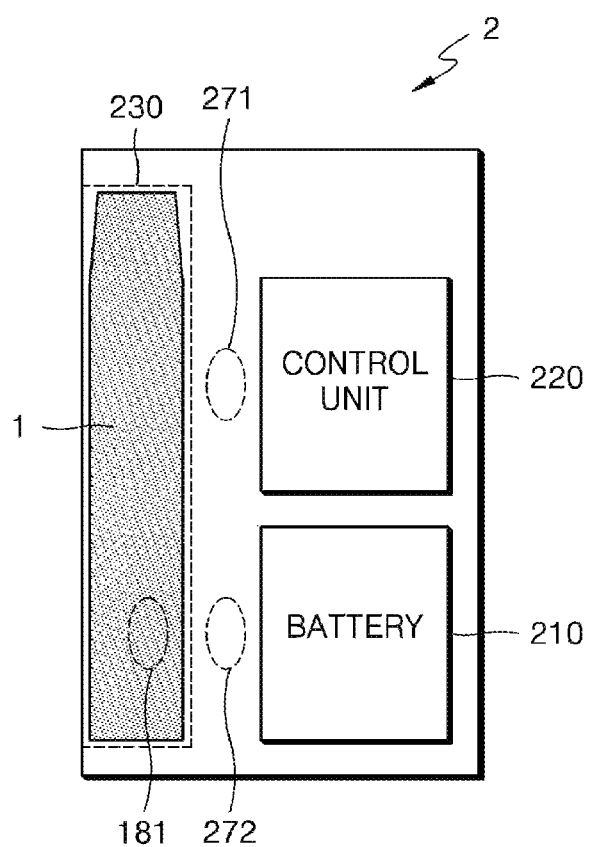
FIG. 9 is a diagram showing an example in which a holder is inserted into a cradle.

FIG. 9 is a diagram showing an example in which a holder is inserted into a cradle.

Referring to FIG. 9, an example in which the holder 1 is inserted into the cradle 2 is shown. Since the space 230 into which the holder 1 is to be inserted is present on one side surface of the cradle 2, the inserted holder 1 may not be exposed to the outside by the other side surfaces of the cradle 2. Therefore, the cradle 2 may not include another component (e.g., a lid) for not exposing the holder 1 to the outside.

The cradle 2 may include at least one attaching member 271 and/or 272 to increase attachment strength with the holder 1. Also, at least one attaching member 181 may be Included in the holder 1 as well. Here, attaching members 181, 271, and 272 may be magnets, but are not limited thereto. Although FIG. 5 shows that the holder 1 includes one attaching member 181 and the cradle 2 includes two attaching members 271 and 272 for convenience of explanation, the number of the attaching members 181, 271, and 272 is not limited thereto.

The holder 1 may include the attaching member 181 at a first position and the cradle 2 may include the attaching members 271 and 272 at a second position and a third position, respectively. In this case, the first position and the third position may be positions facing each other when the holder 1 is inserted into the cradle 2.

Since the attaching members 181, 271, and 272 are Included in the holder 1 and the cradle 2, the holder 1 and the cradle 2 may be attached to each other more strongly even when the holder 1 is inserted into one side surface of the cradle 2. In other words, as the holder 1 and the cradle 2 further include the attaching members 181, 271, and 272 in addition to the terminals 170 and 260, the holder 1 and the cradle 2 may be attached to each other more strongly. Therefore, even when there is no separate component (e.g., a lid) in the cradle 2, the Inserted holder 1 may not be easily separated from the cradle 2.

Also, when the control unit 220 also determines that the holder 1 is completely inserted into the cradle 2 through the terminals 170 and 260 and/or the attaching members 181, 271, and 272, the control unit 220 may charge the battery 110 of the holder 1 by using power of the battery 210.

Figure 10:
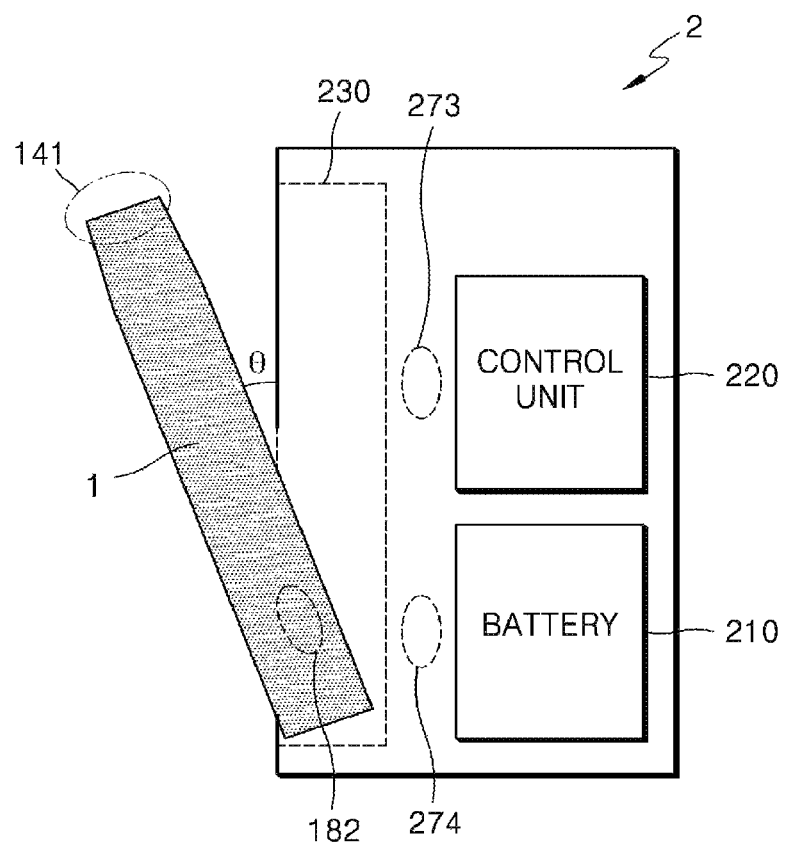
FIG. 10 is a diagram showing an example in which a holder is tilted while being inserted into a cradle.

FIG. 10 is a diagram showing an example in which a holder is tilted while being inserted into a cradle.

Referring to FIG. 10, the holder 1 is tilted inside the cradle 2. Here, the term 'tilting' indicates that the holder 1 is inclined at a certain angle in a state while the holder 1 is being inserted into the cradle 2.

As shown in FIG. 9, when the holder 1 is completely inserted into the cradle 2, a user may not smoke. In other words, once the holder 1 is completely inserted into the cradle 2, a cigarette may not be inserted into the holder 1. Therefore, when the holder 1 is completely inserted into the cradle 2, a user may not smoke.

As shown in FIG. 10, when the holder 1 is tilted, the terminal end 141 of the holder 1 is exposed to the outside. Therefore, the user may insert a cigarette into the terminal end 141 and smoke generated aerosol. A sufficient tilting angle θ may be secured to prevent a cigarette from being bent or damaged when the cigarette is inserted into the terminal end 141 of the holder 1. For example, the holder 1 may be tilted at a minimum angle at which an entire cigarette insertion hole included in the terminal end 141 is exposed to the outside or an angle greater than the minimum angle. For example, the range of the tilting angle θ may be greater than 0° and not greater than 180° and may preferably be not less than 5° and not greater than 90°. More preferably, the range of the tilting angle θ may be from 5° to 20°, from 5° to 30°, from 5° to 40°, from 5° to 50°, or from 5° to 60°. Even more preferably, the tilting angle θ may be 10°.

Also, even when the holder 1 is tilted, the terminal 170 of the holder 1 and the terminal 260 of the cradle 2 are coupled with each other. Therefore, the heater 130 of the holder 1 may be heated by power supplied by the battery 210 of the cradle 2. Therefore, the holder 1 may generate aerosol by using the battery 210 of the cradle 2 even when the remaining power of the battery 110 of the holder 1 is low or the battery 110 of the holder 1 is completely discharged.

FIG. 10 shows an example in which the holder 1 includes one attaching member 182 and the cradle 2 includes two attaching members 273 and 274. For example, the respective positions of the attaching members 182, 273, and 274 are as described above with reference to FIG. 5. Assuming that the attaching members 182, 273, and 274 are magnets, the magneting strength of the attaching member 274 may be greater than the magneting strength of the attaching member 273. Therefore, the holder 1 may not be completely separated from the cradle 2 due to the attaching member 182 and the attaching member 274 even when the holder 1 is tilted.

Also, when it is determined that the holder 1 titled through the terminals 170 and 260 and/or the attaching members 181, 271, and 272, the control unit 220 may heat the heater 130 of the holder 1 or charge the battery 110 by using power of the battery 210.

Figure 11:
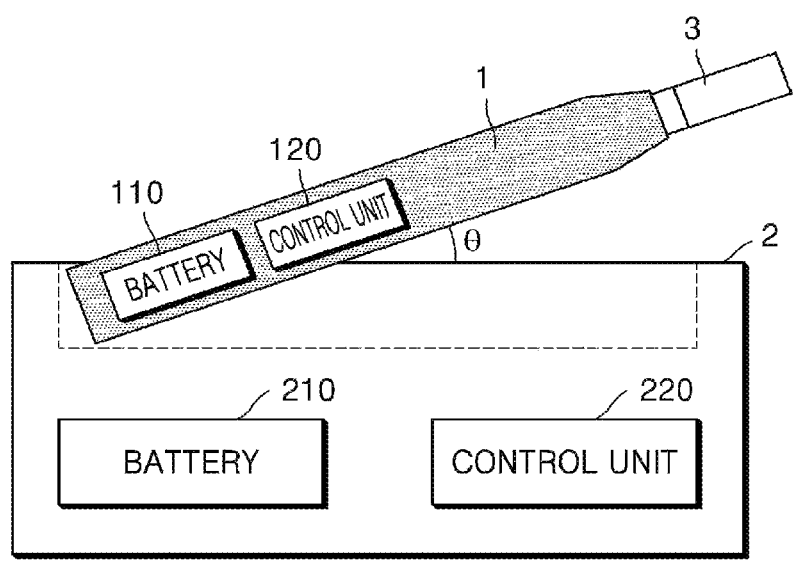
FIG. 11 is a diagram for describing an example of an action of smoking by using a holder tilted in a cradle.

FIG. 11 is a diagram for describing an example of an action of smoking by using a holder tilted in a cradle.

Referring to FIG. 11, the cradle 2 is provided with an inner space for accommodating the holder 1 and, while the holder 1 is being accommodated in the inner space, the inner space and the holder 1 may be tilted, such that the cigarette 3 may be Inserted into the holder 1. The holder 1 may be tilted at an arbitrary tilting angle θ while being coupled with the cradle 2. For example, as described above, the range of the tilting angle θ may be greater than 0° and not greater than 180° and may preferably be not less than 5° and not greater than 90°. More preferably, the range of the tilting angle θ may be from 5° to 20°, from 5° to 30°, from 5° to 40°, from 5° to 50°, or from 5° to 60. Even more preferably, the tilting angle θ may be 10°. A user may insert the cigarette 3 into one terminal end of the holder 1 and smoke while holding the cradle 2 in his/her hand. An aerosol generating system may include at least one of the holder 1, the cradle 2, and the cigarette 3.

In case of performing a smoking action while the holder 1 is being tilted in the cradle 2, the holder 1 may generate aerosols from the cigarette 3 by heating the heater (130 of FIG. 1) by using power supplied from the battery 210 of the cradle 2. Meanwhile, since the holder 1 is still coupled with the cradle 2 even when the holder 1 is tilted, the battery 110 of the holder 1 may be charged by power supplied from the battery 210 of the cradle 2. Meanwhile, the battery 110 of the holder 1 may be used to heat the heater (130 in FIG. 1) only when the holder 1 is separated from the cradle 2, but the present disclosure is not limited thereto.

The control unit 220 of the cradle 2 may determine whether the holder 1 and the cradle 2 are coupled with each other and whether the holder 1 is tilted. When the holder 1 and the cradle 2 are coupled with each other, the control unit 220 may control charging of the battery 110 by the battery 210. When the holder 1 is tilted, the control unit 220 may control the heating of the heater (130 in FIG. 1) of the holder 1 by power supplied from the battery 210, that is, control the temperature of the heater. As described above, when the holder 1 is tilted, a user may continuously smoke for a plurality of number of times through the holder 1 by using power of the battery 210. At this time, for example, one smoking may be set to 14 puffs.

The control unit 120 of the holder 1 may cumulatively monitor smoking patterns a first state in which the holder 1 is tilted in the cradle 2 and a second state in which the holder 1 is separated from the cradle 2 and determine whether the cumulatively monitored smoking patterns satisfy a smoking restriction condition.

In detail, the control unit 120 of the holder 1 may detect the presence of puffs and count the number of puffs. In addition, the control unit 120 of the holder 1 may measure an operation time during which the heater (130 in FIG. 1) is continuously heated. Furthermore, the control unit 120 may determine whether the holder 1 is coupled with the cradle 2, tilted in the cradle 2, or separated from the cradle 2.

When the holder 1 is tilted and the cigarette 3 is inserted into the holder 1, the control unit 120 determines whether the number of puffs of a user has reached a puff limit number or an operation time of the holder 1 reached an operation limit time. When the number of puffs or the operation time reaches the puff limit number or the operation limit time while the holder 1 is being tilted, the control unit 120 controls the heater (130 of FIG. 1) to stop heating the heater. At this time, the control unit 120 of the holder 1 may instruct the control unit 220 of the cradle 2 to stop supplying power of the battery 210, thereby stopping the heating of the heater 130.

The holder 1 may be operated based on a smoking pattern and a smoking restriction condition. The smoking pattern may include, for example, the number of puffs for the inserted cigarette 3. The smoking restriction condition may include the puff limit number. Accordingly, when the number of puffs that are cumulatively monitored in the first state and the second state reaches the puff limit number, the holder 1 may control the heater (130 of FIG. 1) included in the holder 1 to stop the heating of the inserted cigarette 3. Also, the smoking pattern may include an operation time of the holder 1 (e.g., a time for heating the heater (130 in FIG. 1)) and the smoking restriction condition may include an operation limit time. Here, when the operation time that is cumulatively monitored in the first state and the second state reaches the operation limit time, the holder 1 may control the heater (130 of FIG. 1) included in the holder 1 to stop the heating of the inserted cigarette 3.

As described above, the control unit 120 may stop heating of the heater (130 in FIG. 1) when the holder 1 is tilted and the holder 1 is separated from the cradle 2 by a user. At this time, the user may start smoking again by coupling holder 1 with cradle 2.

On the other hand, even when the holder 1 is tilted and separated by the user, the control unit 120 may accumulate and sum the number of counted puffs in the tilted state and the counted number of puffs in the separated state and compare the total number of puffs with a puff limit number, thereby determining whether to heat the heater (130 in FIG. 1). In other words, the control unit 120 of the holder 1 continuously monitors the number of puffs even when the holder 1 is tilted or the holder 1 is separated. Like the number of puffs, the control unit 120 of the holder 1 continuously monitors the operation time of the holder 1 even when the holder 1 is tilted or the holder 1 is separated. As a result, the termination of the operation of the holder 1, that is, the termination of heating of the heater (130 in FIG. 1) may depend on the determination of the control unit 120 of the holder 1.

Figure 12:
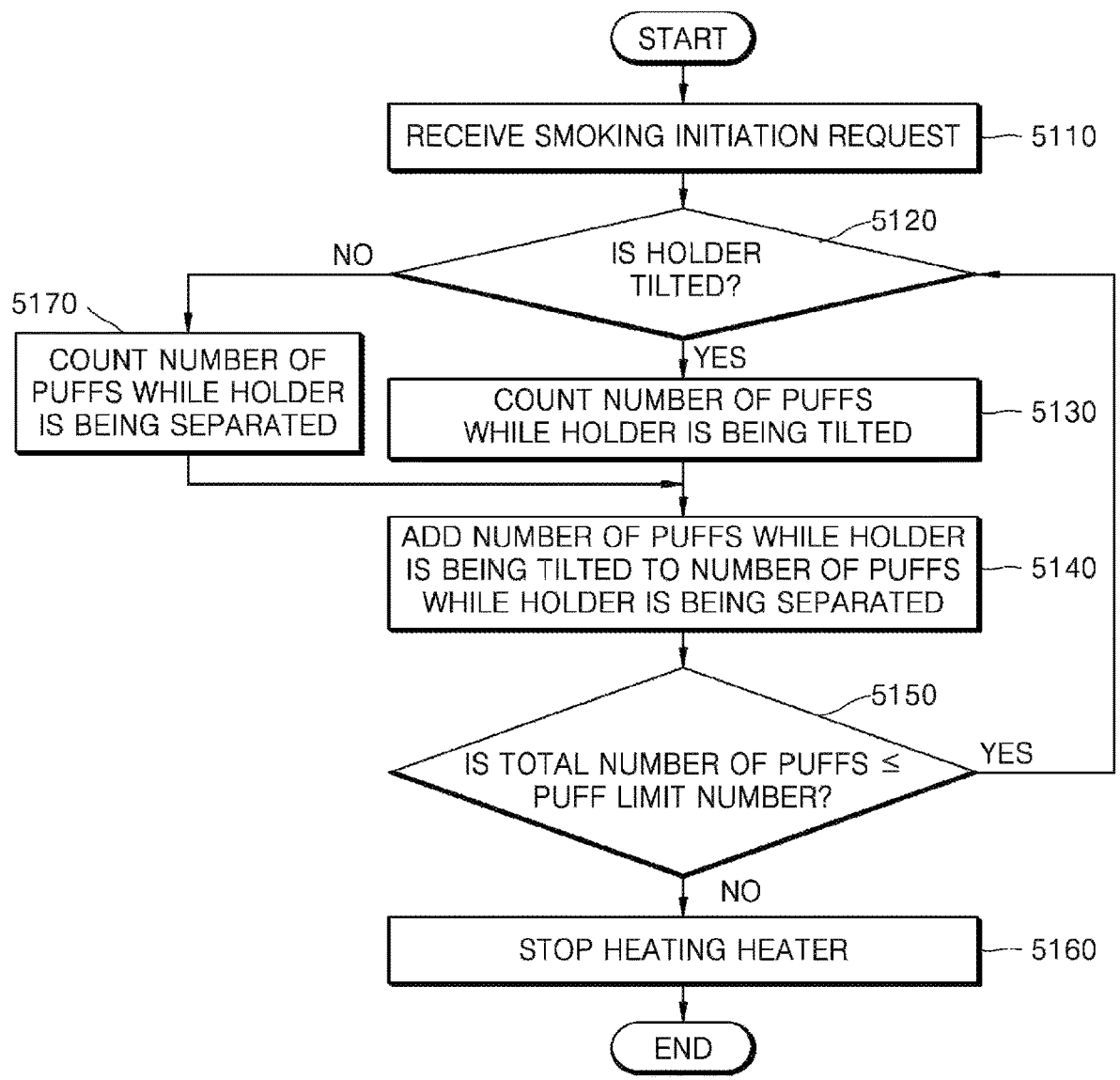
FIG. 12 is a flowchart of a method of counting the number of puffs when a holder is tilted and separated.

FIG. 12 is a flowchart of a method of counting the number of puffs when a holder is tilted and separated.

In operation 5110, the holder 1 or cradle 2 receives a smoking initiation request from a user. The smoking initiation request may be received from the user via an input device provided in the holder 1 or cradle 2. The control unit 120 of the holder 1 or the control unit 220 of the cradle 2 may determine that a smoking initiation request is received when there is an user input. On the other hand, smoking may be performed when the holder 1 is tilted or the holder 1 is separated from the cradle 2. However, when the holder 1 is neither separated from the cradle 2 nor tilted, the holder 1 may operate to prevent the user from smoking, and may not operate a heater or operate the heater only to a temperature or a heating time that is not sufficient for the user to smoke.

Hereinafter, the operation of the holder 1 will be described on the assumption that the holder 1 is tilted or separated from the cradle 2.

In operation 5120, the control unit 120 of the holder 1 determines whether the holder 1 coupled with the cradle 2 is tilted. On the other hand, the control unit 220 of the cradle 2 may also determine whether the holder 1 is tilted. When the holder 1 is tilted, the method proceeds to operation 5130. However, when the holder 1 is separated, the method proceeds to operation 5170.

In operation 5130, the control unit 120 of the holder 1 counts the number of puffs in the tilted state.

In operation 5140, the control unit 120 of the holder 1 sums the number of puffs in the tilted state and the number of puffs in the separated state. When the user puffs the cigarette 3 only in the tilted state, the number of puffs in the separated state is zero.

In operation 5150, the control unit 120 of the holder 1 compares the total number of puffs with a preset puff limit number. For example, the puff limit number may be 14, but is not limited thereto. When the total number of puffs is less than or equal to the puff limit number, the method proceeds to operation 5120. However, when the total number of puffs reaches the puff limit number, the method proceeds to operation 5160.

In operation 5160, the control unit 120 of the holder 1 controls the heater 130 to stop heating the heater (130 in FIG. 1). On the other hand, when the holder 1 is still tilted, the control unit 220 of the cradle 2 may also control the heater 130 to stop heating of the heater 130.

In operation 5170, when the holder 1 is separated from the cradle 2, the control unit 120 of the holder 1 counts the number of puffs in the separated state. Accordingly, in operation 5140, the control unit 120 of the holder 1 may count the total number of puffs by summing the number of counted puffs in the separated state and the number of counted puffs in the tilted state.

Figure 13:
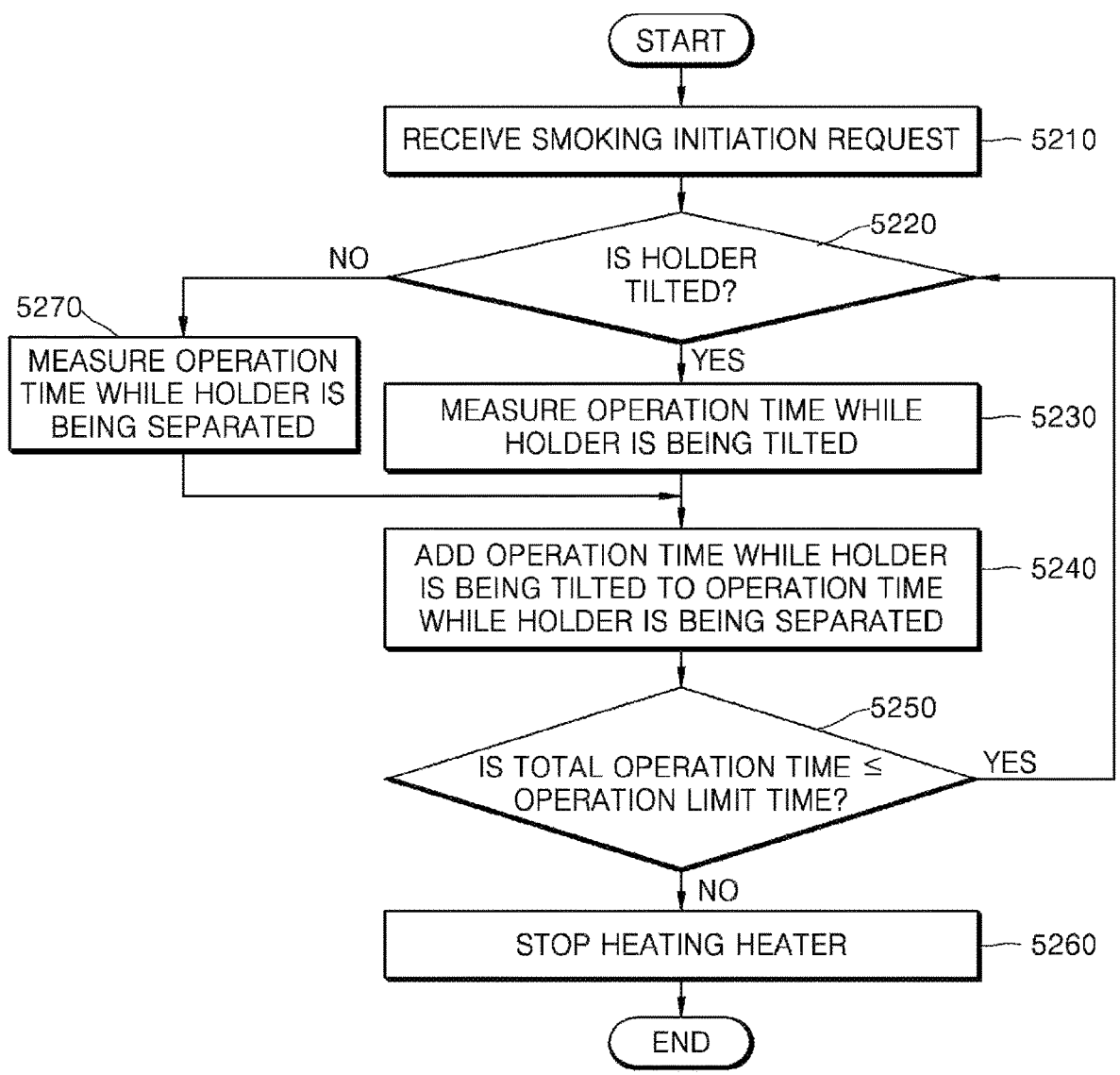
FIG. 13 is a flowchart of a method of measuring an operation time when a holder is tilted and separated.

FIG. 13 is a flowchart of a method of measuring an operation time when a holder is tilted and separated.

In operation 5210, the holder 1 or cradle 2 receives a smoking initiation request from a user.

In operation 5220, the control unit 120 of the holder 1 determines whether the holder 1 coupled with the cradle 2 is tilted. On the other hand, the control unit 220 of the cradle 2 may also determine whether the holder 1 is tilted. When the holder 1 is tilted, the method proceeds to operation 5230. However, when the holder 1 is separated, the method proceeds to operation 5270.

In operation 5230, the control unit 120 of the holder 1 measures an operation time in the tilted state.

In step 2615240, the control unit 120 of the holder 1 adds up the operation time in the tilted state and the operation time in the separated state. When a user operated the holder 1 only when the holder 1 is tilted, the operation time in the separated state is 0 hours.

In operation 5150, the control unit 120 of the holder 1 compares the total operation time with a preset operation limit time. For example, the operation limit time may be 10 minutes, but is not limited thereto. When the total operation time is less than or equal to the operation limit time, the method proceeds to operation 5220. However, when the total operation time reaches the operation limit time, the method proceeds to operation 5260.

In operation 5260, the control unit 120 of the holder 1 controls the heater 130 to stop heating the heater (130 in FIG. 1). On the other hand, when the holder 1 is still tilted, the control unit 220 of the cradle 2 may also control the heater 130 to stop heating of the heater 130.

In operation 5270, when the holder 1 is separated from the cradle 2, the control unit 120 of the holder 1 measures the operation time in the separated state. Accordingly, in operation 5240, the control unit 120 of the holder 1 may measure the total number of puffs by summing the operation time in the separated state and the operation time in the tilted state.

On the other hand, when at least one of the number of puffs described in FIG. 12 and the operation time described in FIG. 13 satisfies a predetermined restriction condition, the holder 1 may control the heater (130 in FIG. 1) to stop heating.

In detail, when smoking is performed in a first state and then performed later in a second state, the holder accumulates a smoking pattern monitored in the second state to a smoking pattern monitored in the first state and, when an accumulated smoking pattern satisfies a smoking restriction condition, the holder 1 controls the heater (130 in FIG. 1) provided in the holder 1 to stop the heating of an inserted cigarette. Also, when smoking is performed in the second state and then performed later in the first state, the holder accumulates a smoking pattern monitored in the first state to a smoking pattern monitored in the second state and, when an accumulated smoking pattern satisfies a smoking restriction condition, the holder 1 controls the heater (130 in FIG. 1) provided in the holder 1 to stop the heating of an inserted cigarette.

Figure 14:
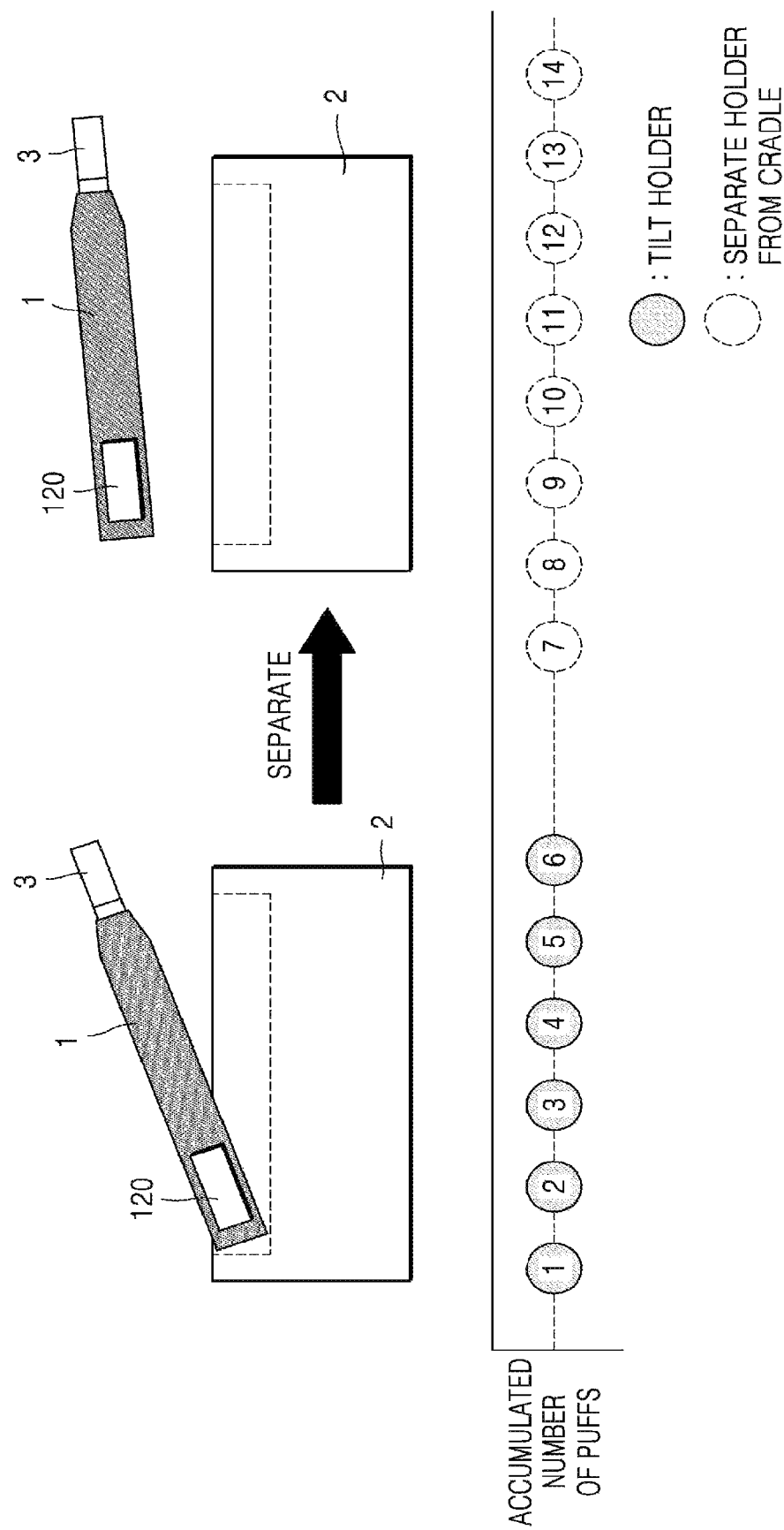
FIG. 14 is a diagram for describing an example that a holder counts the number of puffs.

FIG. 14 is a diagram for describing an example that a holder counts the number of puffs.

Referring to FIG. 14, smoking may be started when the holder 1 tilted in the cradle 2 and the cigarette 3 inserted into the holder 1. A user may puff the cigarette 3 from a first puff to a sixth puff while the holder 1 is being tilted and then separate the holder 1 from the cradle 2. The control unit 120 of the holder 1 cumulatively counts the number of puffs during six puffs.

The user may puff eight more times by using the separated holder 1. At this time, the control unit 120 of the holder 1 may cumulatively count a first puff performed by using the separate holder 1 as a seventh subsequent to the sixth puff in the tilted state. In other words, the control unit 120 of the holder 1 may cumulatively count all puffs performed while the holder 1 is being tilted and being separated. When a cumulative total number of puffs reaches the puff limit number (i.e., when a fourteenth puff is completed), the control unit 120 of the holder 1 may terminate the operation of the holder 1.

Figure 15:
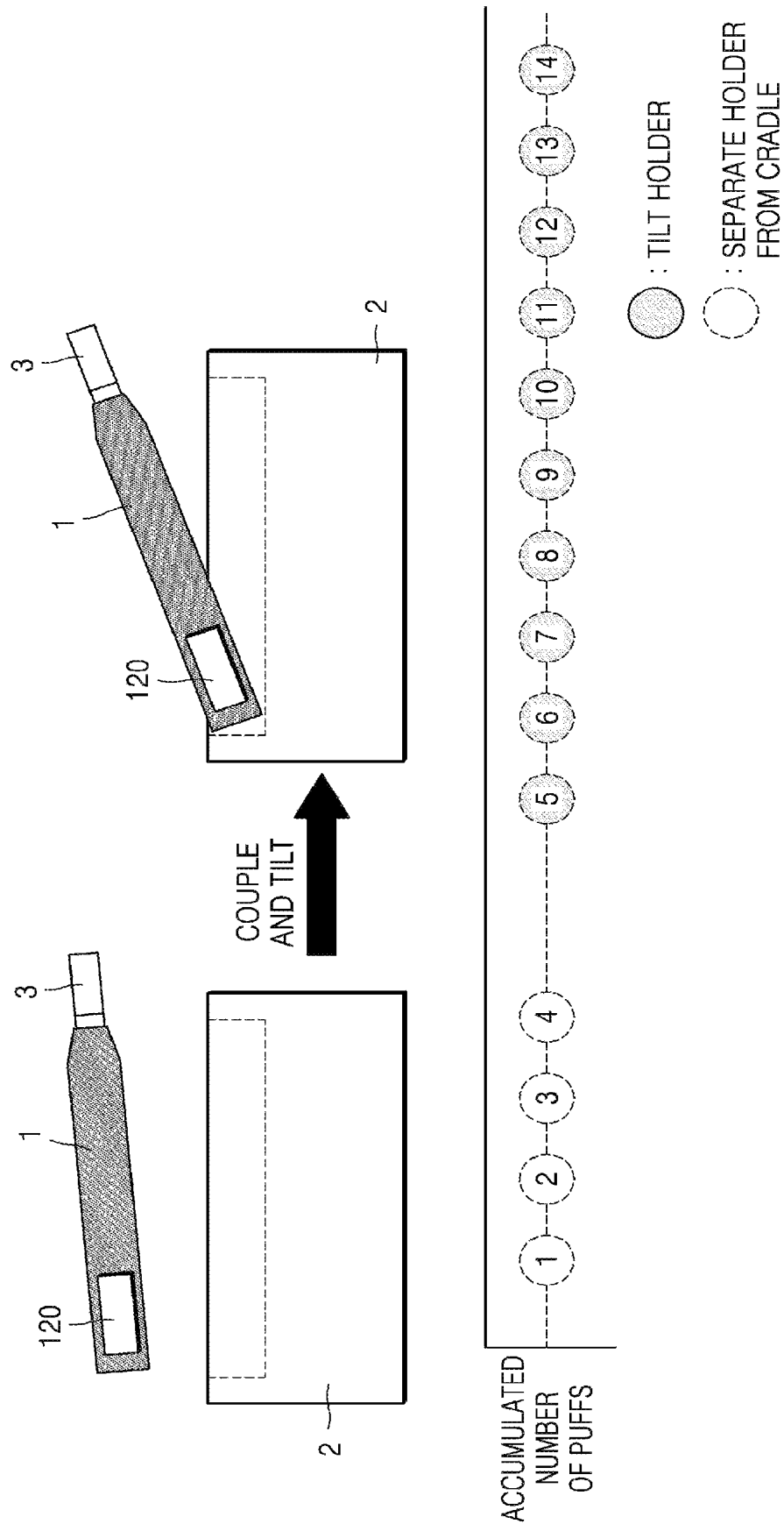
FIG. 15 is a diagram for describing another example that a holder counts the number of puffs.

FIG. 15 is a diagram for describing another example that a holder counts the number of puffs.

Referring to FIG. 15, a case opposite to that of FIG. 14 is described. Smoking may be started after the cigarette 3 is inserted into the holder 1 while the holder 1 is being separated from the cradle 2. A user may puff the cigarette 3 from a first puff to a fourth puff by using the separate holder 1, and then the user may couple the holder 1 with the cradle 2 and tilt the holder 1. The control unit 120 of the holder 1 cumulatively counts the number of puffs during four puffs.

The user may puff ten more times by using the tilted holder 1. At this time, the control unit 120 of the holder 1 may cumulatively count a first puff performed by using the titled holder 1 as a fifth subsequent to the fourth puff in the separated state. In other words, the control unit 120 of the holder 1 may cumulatively count all puffs performed while the holder 1 is being separated and being tilted. When a cumulative total number of puffs reaches the puff limit number (i.e., when a fourteenth puff is completed), the control unit 120 of the holder 1 may terminate the operation of the holder 1.

Figure 16A:
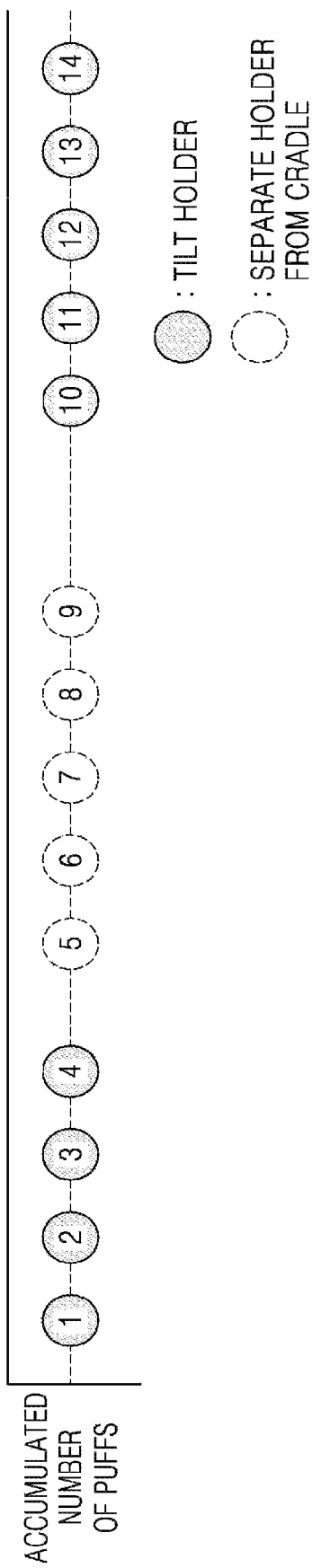
FIGS. 16A and 16B are diagrams for describing another example that a holder counts the number of puffs.
Figure 16B:
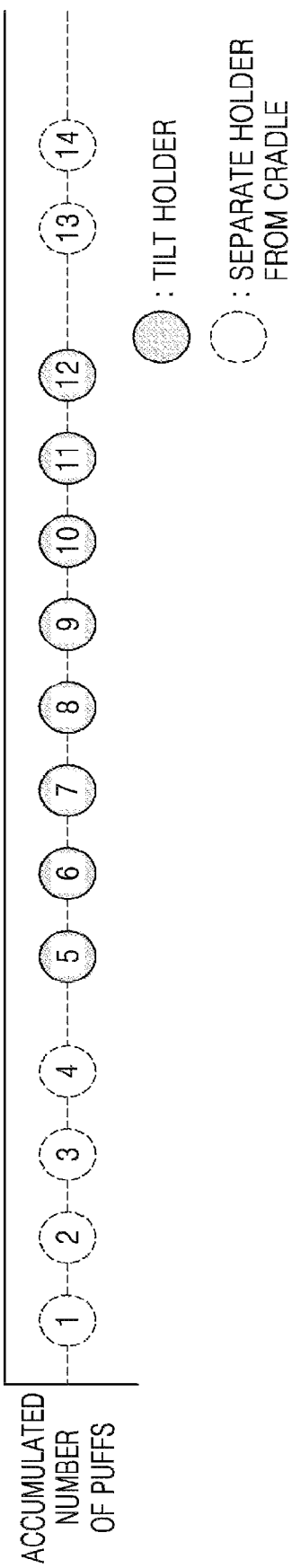

FIG. 16 is a diagram for describing another example that a holder counts the number of puffs.

Referring to FIG. 16A, even when a user uses the holder 1 in the tilted state, uses the holder 1 after separating the holder 1 from the cradle 2, and then uses the holder 1 by tilting it again, the control unit 120 of the control unit 1 may cumulatively count the number of puffs that are performed after initiation of smoking (i.e., the first puff). Similarly, referring to FIG. 168, even when a user uses the holder 1 in the separated state, uses the holder 1 after tilting the holder 1, and then uses the holder 1 by separating it again, the control unit 120 of the control unit 1 may cumulatively count the number of puffs that are performed after initiation of smoking (i.e., the first puff).

In other words, the control unit 120 of the holder 1 cumulatively may count the number of puffs performed after initiation of smoking regardless of whether the holder 1 is tilted or separated and control the operation of the holder 1 based on an accumulated total number of puffs.

Figure 17:
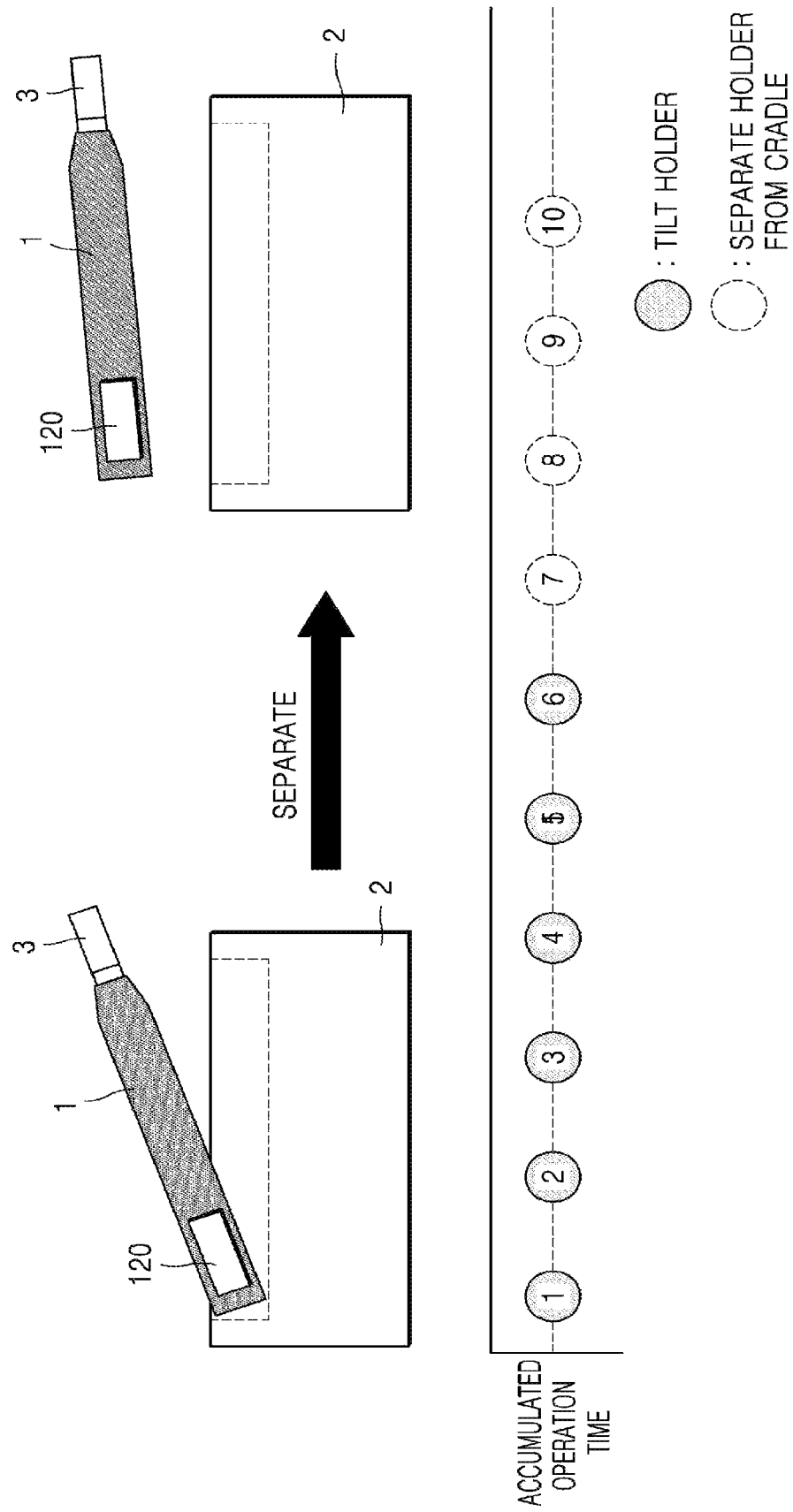
FIG. 17 is a diagram for describing a method that a holder measures an operation time.

FIG. 17 is a diagram for describing a method that a holder measures an operation time.

Referring to FIG. 17, smoking may be started when the holder 1 tilted in the cradle 2 and the cigarette 3 inserted into the holder 1. A user may puff the cigarette 3 for 6 minutes while the holder 1 is being tilted and then separate the holder 1 from the cradle 2. The control unit 120 of the holder 1 measures the operation time while the holder 1 is being tilted.

when the operation time in the tilted state did not reach an operation limit time, the user may further puff by using the separated holder 1. In the example shown in FIG. 20, the user may puff for 4 more minutes. At this time, the control unit 120 of the holder 1 may consider that the operation time before the holder 1 is separated is an operation time that has been already elapsed. In other words, the control unit 120 of the holder 1 may cumulatively measure the entire operation time elapsed while the holder 1 is being tilted and being separated. When a cumulative operation time reaches the operation limit time (i.e., after 10 minutes), the control unit 120 of the holder 1 may terminate the operation of the holder 1.

Figure 18A:
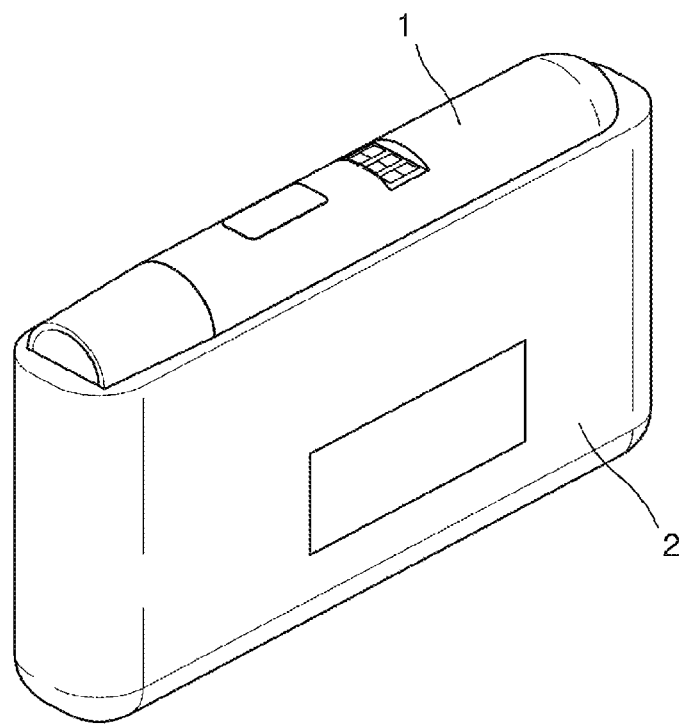
FIGS. 18A to 18B are diagrams showing examples in which a holder is inserted into a cradle.
Figure 18B:
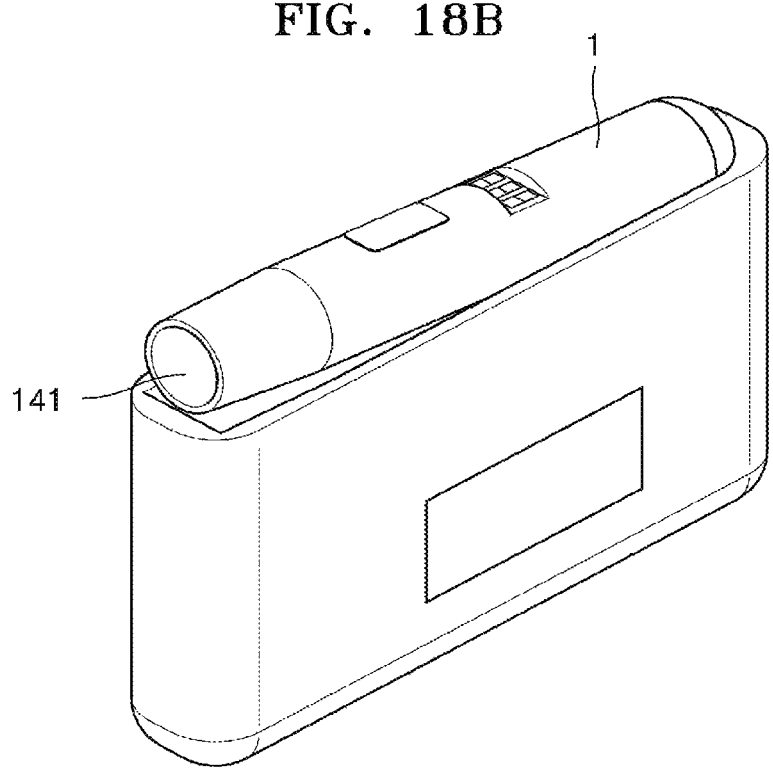

FIGS. 18A to 18B are diagrams showing examples in which a holder is inserted into a cradle.

FIG. 18A shows an example in which the holder 1 is completely inserted into the cradle 2. The cradle 2 may be fabricated to provide the sufficient inner space 230 of the cradle 2 to minimize the contact of a user with the holder 1 when the holder 1 is completely inserted into the cradle 2. When the holder 1 is completely inserted into the cradle 2, the control unit 220 supplies power of the battery 210 to the holder 1, such that the battery 110 of the holder 1 is charged.

FIG. 18B shows an example in which the holder 1 is tilted while being inserted into the cradle 2. When the holder 1 is tilted, the control unit 220 supplies power of the battery 210 to the holder 1, such that the battery 110 of the holder 1 is charged or the heater 130 of the holder 1 is heated.

Figure 19:
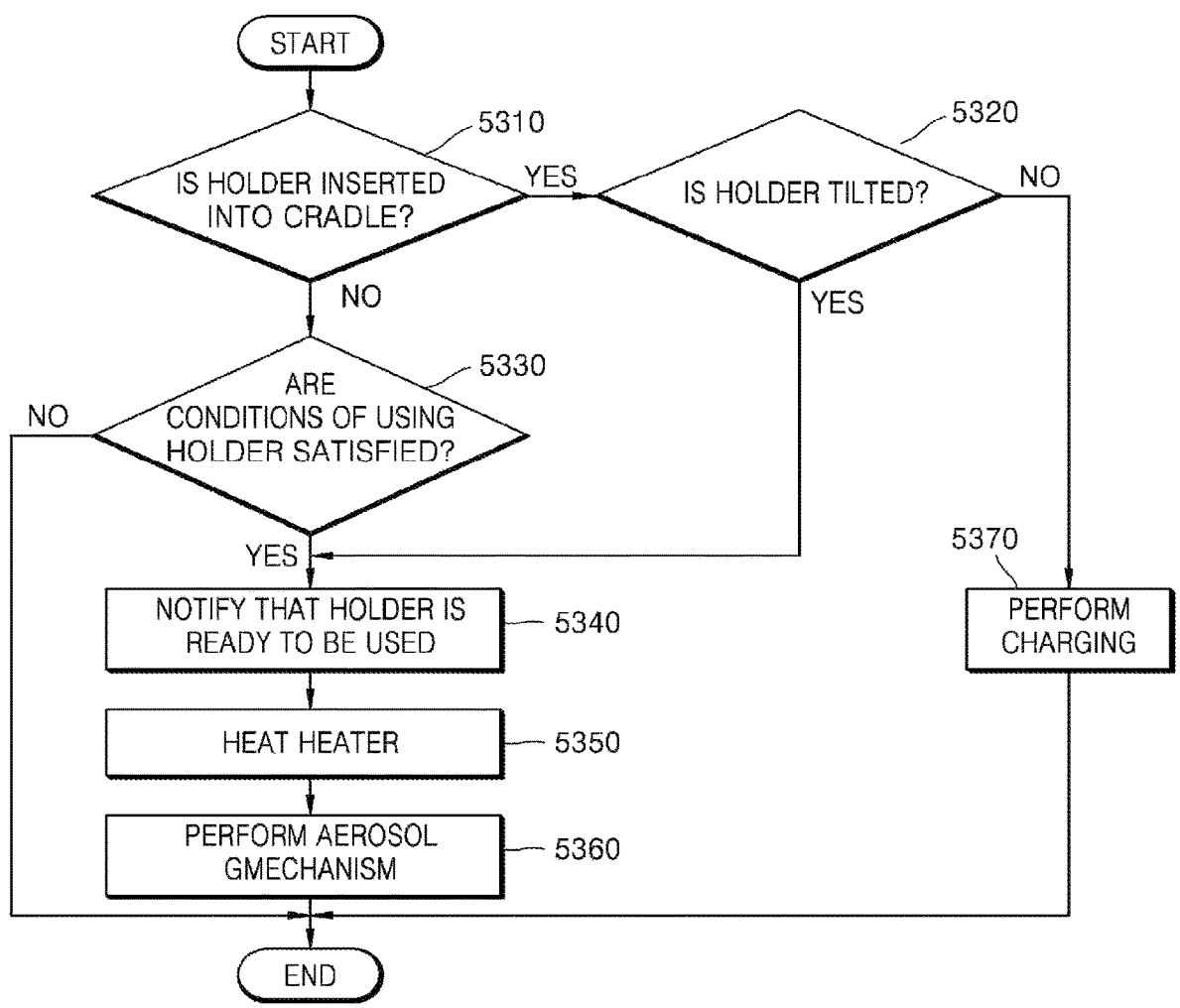
FIG. 19 is a flowchart for describing an example in which a holder and a cradle operates.

FIG. 19 is a flowchart for describing an example in which a holder and a cradle operates.

A method for generating aerosols shown in FIG. 19 includes operations that are performed in a time-series manner by the holder 1 or the cradle 2 shown in FIGS. 1 to 18B. Therefore, it will be understood that the descriptions given above with respect to the holder 1 and the cradle 2 shown in FIGS. 1 to 18B also apply to the method of FIG. 19, even when the descriptions are omitted below.

In operation 5310, the holder 1 determines whether it is inserted in the cradle 2. For example, the control unit 120 may determine whether the holder 1 is inserted into the cradle 2 based on whether the terminals 170 and 260 of the holder 1 and the cradle 2 are connected to each other and/or whether the attaching members 181, 271, and 272 are operating.

When the holder 1 is inserted into the cradle 2, the method proceeds to operation 5320. When the holder 1 is separated from the cradle 2, the method proceeds to operation 5330.

In operation 5320, the cradle 2 determines whether the holder 1 is tilted. For example, the control unit 220 may determine whether the holder 1 is inserted into the cradle 2 based on whether the terminals 170 and 260 of the holder 1 and the cradle 2 are connected to each other and/or whether attaching members 182, 273, and 274 are operating.

Although it is described that the cradle 2 determines whether the holder 1 is tilted in operation 5320, the present disclosure is not limited thereto. In other words, the control unit 120 of the holder 1 may determine whether the holder 1 is tilted.

When the holder 1 is tilted, the method proceeds to operation 5340. When the holder 1 is not tilted (i.e., the holder 1 is completely inserted into the cradle 2), the method proceeds to operation 5370.

In operation 5330, the holder 1 determines whether conditions of using the holder 1 are satisfied. For example, the control unit 120 may determine whether the conditions for using the holder 1 are satisfied by checking whether the remaining power of the battery 110 and whether other components of the holder 1 may be normally operated.

When the conditions for using the holder 1 are satisfied, the method proceeds to operation 5340. Otherwise, the method is terminated.

In operation 5340, the holder 1 informs a user that the holder 1 is ready to be used. For example, the control unit 120 may output an image indicating that the holder 1 is ready to be used on the display of the holder 1 or may control the motor of the holder 1 to generate a vibration signal.

In operation 5350, the heater 130 is heated. For example, when the holder 1 is separated from the cradle 2, the heater 130 may be heated by power of the battery 110 of the holder 1. In another example, when the holder 1 is tilted, the heater 130 may be heated by power of the battery 210 of the cradle 2.

The control unit 120 of the holder 1 or the control unit 220 of the cradle 2 may check the temperature of the heater 130 in real time and control an amount of power supplied to the heater 130 and a time for supplying the power to the heater 130. For example, the control unit 120 or 220 may check the temperature of the heater 130 in real time through a temperature sensor Included in the holder 1 or an electrically conductive track of the heater 130.

In operation 5360, the holder 1 performs an aerosol generation mechanism. For example, the control unit 120, 220 may check the temperature of the heater 130, which changes as a user performs puffs, and adjust an amount of power supplied to the heater 130 or stop supplying power to the heater 130. Also, the control unit 120 or 220 may count the number of puffs of the user and output information indicating that the holder 1 needs to be cleaned when the number of puffs reaches a certain number of times (e.g., 1500).

In operation 5370, the cradle 2 performs charging of the holder 1. For example, the control unit 220 may charge the holder 1 by supplying power of the battery 210 of the cradle 2 to the battery 110 of the holder 1.

Meanwhile, the control unit 120 or 220 may stop the operation of the holder 1 according to the number of puffs of the user or the operation time of the holder 1. Hereinafter, an example in which the control unit 120 or 220 stops the operation of the holder 1 will be described with reference to FIG. 20.

Figure 20:
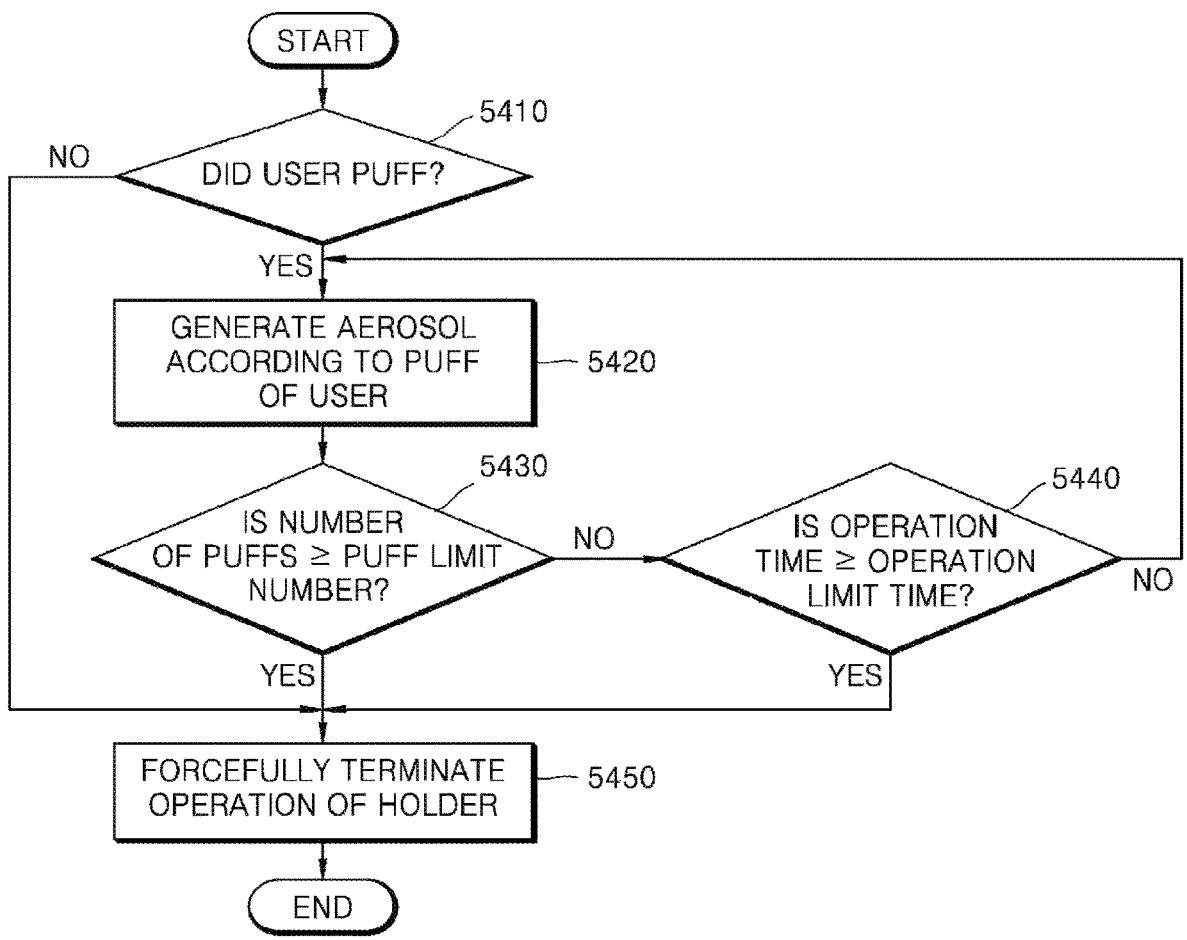
FIG. 20 is a flowchart for describing another example in which a holder operates.

FIG. 20 is a flowchart for describing another example in which a holder operates.

A method for generating aerosols shown in FIG. 20 includes operations that are performed in a time-series manner by the holder 1 and the cradle 2 shown in FIGS. 1 to 18B. Therefore, it will be understood that the descriptions given above with respect to the holder 1 and the cradle 2 shown in FIGS. 1 to 18B also apply to the method of FIG. 20, even when the descriptions are omitted below.

In operation 5410, the control unit 120 or 220 determines whether a user puffed. For example, the control unit 120 or 220 may determine whether the user puffed through the puff detecting sensor included in the holder 1. Alternatively, the control unit 120 or 220 may determine whether the user puffed by using the resistance change of the electrically conductive track included in the heater 130. Here, the electrically conductive track includes an electrically conductive track for generating heat and/or an electrically conductive track for sensing temperature. Alternatively, the control unit 120 or 220 may determine whether the user puffed by using both the resistance change of the electrically conductive track included in the heater 130 and the puff detecting sensor.

In operation 5420, aerosol is generated according to the puff of the user. The control unit 120 or 220 may adjust power supplied to the heater 130 according to the puff of the user the temperature of the heater 130, as described above with reference to FIG. 19. Also, the control unit 120 or 220 counts the number of puffs of the user.

In operation 5430, the control unit 120 or 220 determines whether the number of puffs of the user equal to or greater than a puff limit number. For example, assuming that the puff limit number is set to 14, the control unit 120 or 220 determines whether the number of counted puffs is 14 or more. However, the puff limit number is not limited to 14. For example, the puff limit number may be set to an appropriate number of times from 10 to 16.

On the other hand, when the number of puffs of the user is close to the puff limit number (e.g., when the number of puffs of the user is 12), the control unit 120 or 220 may output a warning signal through a display or a vibration motor.

When the number of puffs of the user is equal to or greater than the puff limit number, the method proceeds to operation 5450. When the number of puffs of the user is less than the puff limit number, the method proceeds to operation 5440.

In operation 5440, the control unit 120 or 220 determines whether the operation time of the holder 1 is equal to or greater than an operation limit time. Here, the operation time of the holder 1 refers to accumulated time from a time point at which the holder 1 started its operation to a current time point. For example, assuming that the operation limit time is set to 10 minutes, the control unit 120 or 220 determines whether the holder 1 is operating for 10 minutes or longer.

On the other hand, when the operation time of the holder 1 is close to the operation limit time (e.g., when the holder 1 is operating for 8 minutes), the control unit 120 or 220 may output a warning signal through a display or a vibration motor.

When the holder 1 is operating for the operation limit time or longer, the method proceeds to operation 5450. When the operation time of the holder 1 is less than the operation limit time, the method proceeds to operation 5420.

In operation 5450, the control unit 120 or 220 forcibly terminates the operation of the holder 1. In other words, the control unit 120 or 220 terminates the aerosol generation mechanism of the holder 1. For example, the control unit 120 or 220 may forcibly terminate the operation of the holder 1 by interrupting the power supplied to the heater 130.

Figure 21:
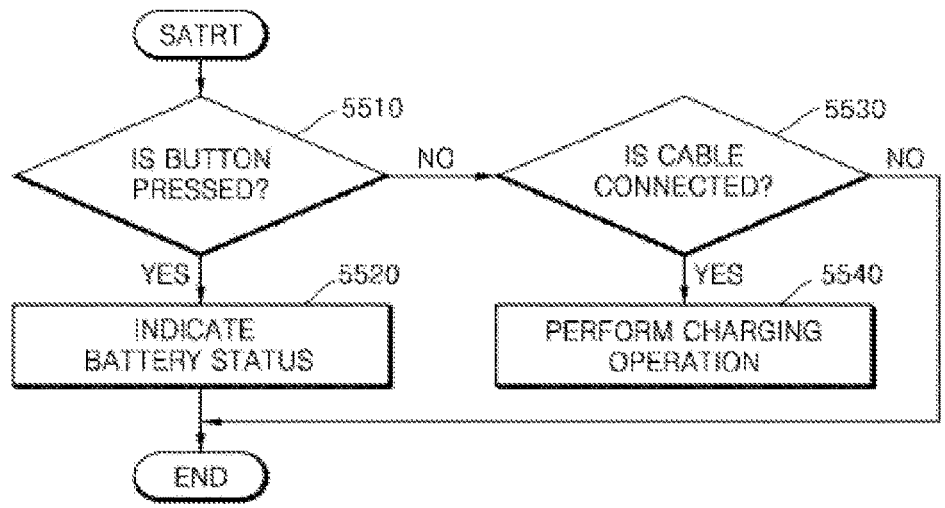
FIG. 21 is a flowchart for describing an example in which a cradle operates.

FIG. 21 is a flowchart for describing an example in which a cradle operates.

The flowchart shown in FIG. 21 includes operations that are performed in a time-series manner by the cradle 2 shown in FIGS. 7 to 18B. Therefore, it will be understood that the descriptions given above with respect to the cradle 2 shown in FIGS. 7 to 18B also apply to the method of FIG. 21, even when the descriptions are omitted below.

Although not shown in FIG. 21, the operation of the cradle 2 to be described below may be performed regardless of whether the holder 1 is inserted into the cradle 2.

In operation 5510, the control unit 220 of the cradle 2 determines whether the button 240 is pressed. When the button 240 is pressed, the method proceeds to operation 5520. When the button 240 is not pressed, the method proceeds to operation 5530.

In operation 5520, the cradle 2 indicates the status of the battery 210. For example, the control unit 220 may output information regarding the current state of the battery 210 (e.g., remaining power, etc.) on the display 250.

In operation 5530, the control unit 220 of the cradle 2 determines whether a cable is connected to the cradle 2. For example, the control unit 220 determines whether a cable is connected to an interface (e.g., a USB port, etc.) included in the cradle 2. When a cable is connected to the cradle 2, the method proceeds to operation 5540. Otherwise, the method is terminated.

In operation 5540, the cradle 2 performs a charging operation. For example, the cradle 2 charges the battery 210 by using power supplied through a connected cable.

As described above with reference to FIG. 1, a cigarette may be inserted into the holder 1. The cigarette includes an aerosol generating material and aerosol is generated by the heated heater 130.

Hereinafter, an example of a cigarette that may be Inserted into the holder 1 will be described with reference to FIGS. 22 to 38C.

Figure 22:
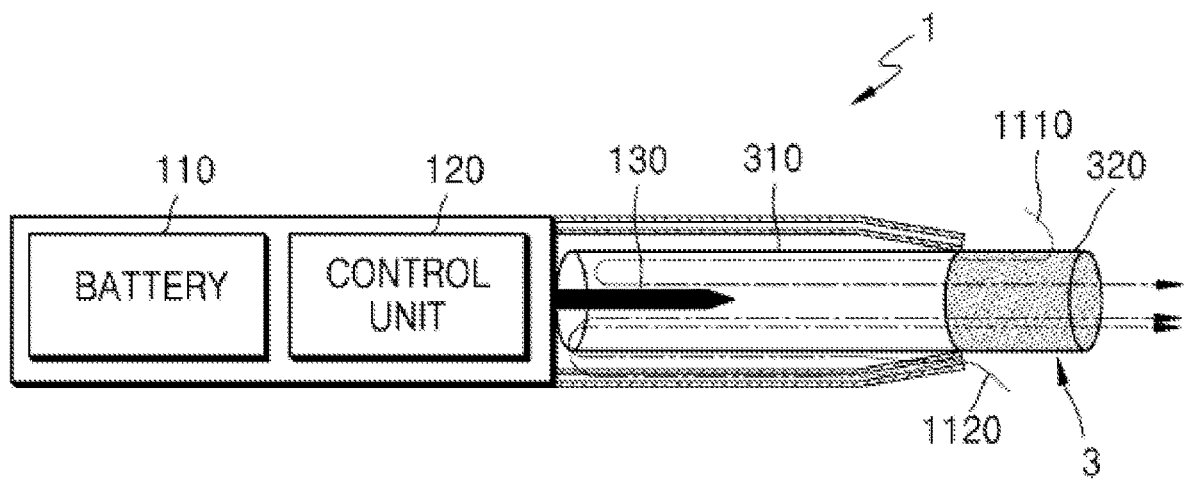
FIG. 22 is a diagram showing an example in which a cigarette is inserted into a holder.

FIG. 22 is a diagram showing an example in which a cigarette is inserted into a holder.

Referring to FIG. 22, the cigarette 3 may be inserted into the holder 1 through the terminal end 141 of the casing 140. When the cigarette 31s inserted into the holder 1, the heater 130 is located inside the cigarette 3. Therefore, the heated heater 130 heats the aerosol generating material of the cigarette 3, thereby generating aerosol.

The cigarette 3 may be similar to a typical burning cigarette. For example, the cigarette 3 may include a first portion 310 containing an aerosol generating material and a second portion 320 including a filter and the like. Meanwhile, the cigarette 3 according to one embodiment may also include an aerosol generating material in the second portion 320. For example, an aerosol generating material in the form of granules or capsules may be inserted into the second portion 320.

The entire first portion 310 may be inserted into the holder 1 and the second portion 320 may be exposed to the outside. Alternatively, only a portion of the first portion 310 may be inserted into the holder 1 or the entire first portion 310 and a portion the second portion 320 may be inserted into the holder 1.

A user may inhale the aerosol while holding the second portion 320 by his/her lips. At this time, the aerosol is generated by as the outside air passes through the first portion 310, and the generated aerosol passes through the second portion and is delivered to a user's mouth.

The outside air may be introduced (1120) through at least one air passage formed in the holder 1. For example, the opening and closing of the air passage formed in the holder 1 and/or the size of the air passage may be adjusted by a user. Accordingly, an amount of smoke and a smoking impression may be adjusted by the user.

Alternatively, the outside air may be introduced (1110) through at least one hole formed in the surface of the cigarette 3.

Figure 23A:
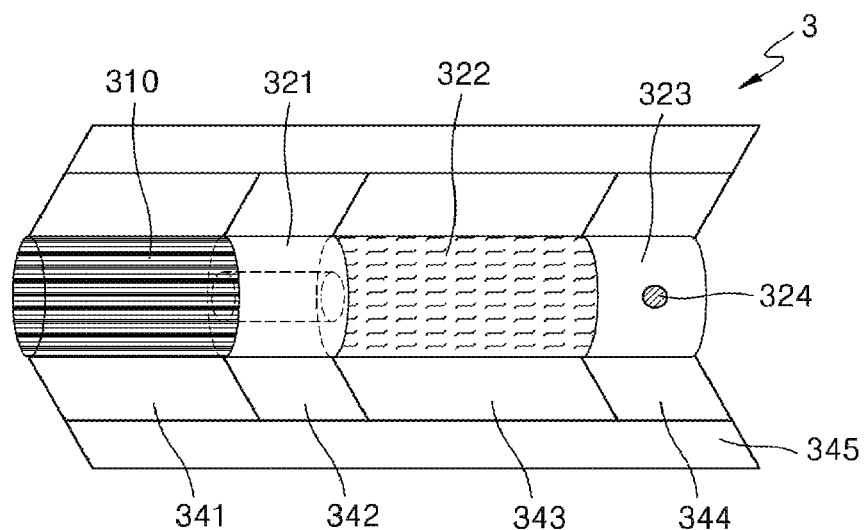
FIGS. 23A and 23B are block diagrams showing examples of a cigarette.
Figure 23B:
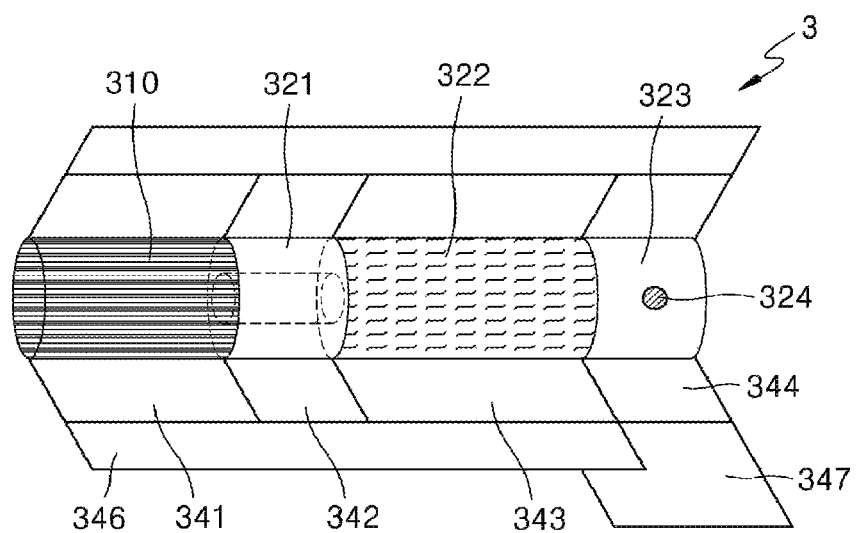

FIGS. 23A and 23B are block diagrams showing examples of a cigarette.

Referring to FIGS. 23A and 23B, the cigarette 3 includes a tobacco rod 310, a first filter segment 321, a cooling structure 322, and a second filter segment 323. The first portion 310 described above with reference to FIG. 11 includes the tobacco rod 310 and the second portion 320 includes the first filter segment 321, the cooling structure 322, and the second filter segment 323.

Referring to FIG. 23A, the cigarette 3 may be packaged by a total five wrappers 341, 342, 343, 344, and 345. Meanwhile, referring to FIG. 23B, the cigarette 3 may be packaged by a total of six wrappers 341, 342, 343, 344, 346, and 347. The tobacco rod 310 is packed by a first wrapper 341, and the first filter segment 321 is packaged by a second wrapper 342. Also, the cooling structure 322 is packed by a third wrapper 343, and the second filter segment 323 is packed by a fourth wrapper 344.

A fifth wrapper 345 of FIG. 23A may be wrapped around the first wrapper 341, the second wrapper 342, the third wrapper 343, and the fourth wrapper 344. In other words, the entire cigarette 3 may be double-packaged by the fifth wrapper 345.

On the other hand, a sixth wrapper 346 of FIG. 23B may be wrapped around the first wrapper 341, the second wrapper 342, and the third wrapper 343. In other words, the tobacco rod 310, the first filter segment 321, and the cooling structure 322 of the cigarette 3 may be double-packaged by the sixth wrapper 346. Also, a seventh wrapper 347 of FIG. 23B may be wrapped around at least a portion of the third wrapper 343 and the fourth wrapper 344. In other words, at least a portion of the cooling structure 322 and the second filter segment 323 of the cigarette 3 may be re-packaged by the seventh wrapper 347.

The first wrapper 341 and the second wrapper 342 may be fabricated using a general filter wrapping paper. For example, the first wrapper 341 and the second wrapper 342 may include a porous wrapping paper or a non-porous wrapping paper. Also, the first wrapper 341 and the second wrapper 342 may be made of an oil-resistant paper sheet and an aluminum laminate packaging material.

The third wrapper 343 may be made of a hard wrapping paper. For example, the basis weight of the third wrapper 343 may be, but is not limited to, 90 g/m$^2$.

The fourth wrapper 344 may be made of an oil-resistant hard wrapping paper. For example, the basis weight of the fourth wrapper 344 may be 92 g/m$^2$ and the thickness thereof may be 125 μm, but the present disclosure is not limited thereto.

The fifth wrapper 345, the sixth wrapper 346, and the seventh wrapper 347 may be made of a sterilized paper (MFW). Here, the MFW refers to a paper specially manufactured to have the tensile strength, the water resistance, the smoothness, and the like that are improved compared to those of ordinary paper. For example, the basis weight of the fifth wrapper 345, the sixth wrapper 346, and the seventh wrapper 347 may be 60 g/m$^2$ and the thickness thereof may be 67 m, but the present disclosure is not limited thereto. Also, the tensile strengths of the fifth wrapper 345, the sixth wrapper 346, and the seventh wrapper 347 may be within the range from 8 kgf/15 mm to 11 kgf/15 mm for dry type and may be 1.0 kgf/15 mm for wet type, but the present disclosure is not limited thereto.

A predetermined material may be included in the fifth wrapper 345, the sixth wrapper 346, and the seventh wrapper 347. Here, an example of the predetermined material may be, but is not limited to, silicon. For example, silicon exhibits characteristics like heat resistance with little change due to the temperature, oxidation resistance, resistances to various chemicals, water repellency, electrical insulation, etc. However, any material other than silicon may be applied to (or coated on) the fifth wrapper 345, the sixth wrapper 346, and the seventh wrapper 347 without limitation as long as the material exhibits the above-mentioned characteristics.

The fifth wrapper 345, the sixth wrapper 346, and the seventh wrapper 347 may prevent the cigarette 3 from being burned. For example, when the tobacco rod 310 is heated by the heater 130, there is a possibility that the cigarette 3 is burned. In detail, when the temperature is raised to a temperature above the ignition point of any one of materials included in the tobacco rod 310, the cigarette 3 may be burned. Even in this case, since the fifth wrapper 345, the sixth wrapper 346, and the seventh wrapper 347 include a non-combustible material, the burning of the cigarette 3 may be prevented.

Furthermore, the fifth wrapper 345, the sixth wrapper 346, and the seventh wrapper 347 may prevent the holder 1 from being contaminated by substances formed by the cigarette 3. Through puffs of a user, liquid substances may be formed in the cigarette 3. For example, as the aerosol formed by the cigarette 3 is cooled by the outside air, liquid materials (e.g., moisture, etc.) may be formed. As the fifth wrapper 345, the sixth wrapper 346, and the seventh wrapper 347 wrap the tobacco rod 310 and/or the first filter segment 321, the liquid materials formed in the cigarette 3 may be prevented from being leaked out of the cigarette 3. Accordingly, the casing 140 of the holder 1 and the like may be prevented from being contaminated by the liquid materials formed by the cigarette 3.

The diameter of the cigarette 3 may be within the range from 5 mm to 9 mm, and the length thereof may be about 48 mm. However, the present disclosure is not limited thereto. Preferably, the diameter of the cigarette 3 may be 7.2 mm, but is not limited thereto. In addition, the length of the tobacco rod 310 may be about 12 mm, the length of the first filter segment 321 may be about 10 mm, the length of the cooling structure 322 may be about 14 mm, and the length of the second filter segment 323 may be about 12 mm, but the present disclosure is not limited thereto.

The structures of the cigarette 3 shown in FIGS. 23A and 23B are merely examples, and some of the components may be omitted. For example, the cigarette 3 may not include one or more of the first filter segment 321, the cooling structure 322, and the second filter segment 323.

The tobacco rod 310 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol.

In addition, the tobacco rod 310 may include other additive materials like a flavoring agent, a wetting agent, and/or an organic acid. For example, the flavoring agent may Include licorice, sucrose, fructose syrup, isosweet, cocoa, lavender, cinnamon, cardamom, celery, fenugreek, cascara, sandalwood, bergamot, geranium, honey essence, rose oil, vanilla, lemon oil, orange oil, mint oil, cinnamon, keragene, cognac, jasmine, chamomile, menthol, cinnamon, ylang ylang, salvia, spearmint, ginger, coriander, coffee, etc. In addition, the wetting agent may include glycerin or propylene glycol.

For example, the tobacco rod 310 may be filled with cut tobacco leaves. Here, cut tobacco leaves may be formed by fine-cutting a tobacco sheet.

For a large wide tobacco sheet to be filled within the tobacco rod 310 having a narrow space, a special operation for facilitating folding of the tobacco sheet is further needed. Therefore, it is easier to fill the tobacco rod 310 with cut tobacco leaves compared to filling the tobacco rod 310 with a tobacco sheet, and thus the productivity and the efficiency of the process for producing the tobacco rod 310 may be improved.

In another example, the tobacco rod 310 may be filled with a plurality of cigarette strands formed by fine-cutting a tobacco sheet. For example, the tobacco rod 310 may be formed by combining a plurality of tobacco strands in the same direction (parallel to one another) or randomly. In detail, the tobacco rod 310 may be formed by combining a plurality of tobacco strands, and a plurality of vertical channels through which the heater 130 may be inserted or aerosol may pass may be formed.

At this time, depending on the sizes and arrangements of the tobacco strands, the vertical channels may be uniform or non-uniform.

For example, tobacco strands may be formed through the following operations. First, a raw tobacco material is pulverized to form a slurry in which an aerosol generating material (e.g., glycerin, propylene glycol, etc.), a flavoring liquid, a binder (e.g., guar gum, xanthan gum, carboxymethyl cellulose (CMC), etc.), and water are mixed, and then a sheet is formed by using the slurry. When forming the slurry, natural pulp or cellulose may be added to modify the physical properties of tobacco strands, and one or more binders may be mixed and used. Next, after drying the sheet, tobacco strands may be formed by fold-cutting or fine-cutting the dried sheet.

The raw tobacco material may be tobacco leaf fragments, tobacco stems, and/or fine tobacco powders formed during treatment of tobacco. The tobacco sheet may also include other additives like wood cellulose fibers.

The slurry may contain 5% to 40% aerosol generating material, and 2% to 35% aerosol generating material may remain in completed tobacco strands. Preferably, 10% to 25% of the aerosol generating material may remain in the completed tobacco strands.

Also, before the tobacco rod 310 is packaged by the first wrapper 341, a flavoring liquid like a menthol or a moisturizer may be spray-added to the center of the tobacco rod 310.

The tobacco strands may be fabricated to have cuboidal shapes having horizontal lengths from 0.5 mm to 2 mm, vertical lengths from 5 mm to 50 mm, and thicknesses (heights) from 0.1 mm to 0.3 mm, but the present disclosure is not limited thereto. Preferably, the tobacco strands may be fabricated to have a cuboidal shape having the horizontal length of 0.9 mm, the vertical length of 20 mm, and the thickness (height) of 0.2 mm. Also, one tobacco strand may be fabricated to have a basis weight from 100 g/m$^2$ to 250 g/m$^2$, but the present disclosure is not limited thereto. Preferably, one tobacco strand may be fabricated to have a basis weight of 180 g/m$^2$.

Compared to the tobacco rod 310 filled with a cigarette sheet, the tobacco rod 310 filled with tobacco strands may generate a greater amount of aerosol. In the case of filling the same space, compared to a tobacco sheet, tobacco strands ensure a wider surface area. A wider surface area indicates that an aerosol generating material has a greater chance of contacting the outside air. Therefore, when the tobacco rod 310 is filled with tobacco strands, more aerosol may be generated as compared to the tobacco rod 310 filled with a tobacco sheet.

Furthermore, when the cigarette 3 is separated from the holder 1, the tobacco rod 310 filled with tobacco strands may be separated more easily than the tobacco rod 310 filled with a tobacco sheet. In other words, when the tobacco rod 310 is filled with tobacco strands, the tobacco rod 310 may be more easily separated from the holder 1 than the tobacco sheet 310 filled with a tobacco sheet.

The first filter segment 321 may be a cellulose acetate filter. For example, the first filter segment 321 may have a tubular structure including a hollowness therein. The length of the first filter segment 321 may be any suitable length within the range from 4 mm to 30 mm, but is not limited thereto. Preferably, the length of the first filter segment 321 may be 10 mm, but is not limited thereto.

The diameter of the hollowness included in the first filter segment 321 may be any suitable diameter within the range from 3 mm to 4.5 mm, but is not limited thereto.

The hardness of the first filter segment 321 may be adjusted by adjusting the content of a plasticizer in during fabrication of the first filter segment 321.

To prevent the size of the first filter segment 321 from decreasing over time, the first filter segment 321 may be wrapped by a wrapper. Therefore, the first filter segment 321 may be easily combined with other components (e.g., other filter segments).

Also, the first filter segment 321 may be fabricated by inserting structures of the same type or different types like films or tubes thereinto (e.g., into the hollowness).

The first filter segment 321 may be fabricated using cellulose acetate. Therefore, the inner material of the tobacco rod 310 may be prevented from being pushed back when the heater 130 is inserted, and the effect of cooling an aerosol may occur.

The second filter segment 323 may also be a cellulose acetate filter. For example, the second filter segment 323 may be fabricated as a recess filter, but is not limited thereto. The length of the second filter segment 323 may be appropriately selected within the range from 4 mm to 20 mm. For example, the length of the second filter segment 323 may be about 12 mm, but is not limited thereto.

The second filter segment 323 may be fabricated to generate a flavor by spraying a flavoring liquid to the second filter segment 323 during fabrication of the second filter segment 323. Alternatively, separate fibers coated with a flavoring liquid may be inserted into the second filter segment 323. Aerosol formed in the tobacco rod 310 is cooled as it passes through the cooling structure 322, and the cooled aerosol is delivered to a user through the second filter segment 323. Therefore, when a flavoring material is added to the second filter segment 323, the effect of enhancing the persistence of a flavor delivered to the user may occur.

Also, the second filter segment 323 may include at least one capsule 324. Here, the capsule 324 may have a structure in which a content liquid containing a flavoring material is wrapped with a film. For example, the capsule 324 may have a spherical or cylindrical shape.

The film of the capsule 324 may be fabricated by using a material including agar, pectin, sodium alginate, carrageenan, gelatin, or a gum like guar gum. Furthermore, a gelling agent may be further used as a material for forming the film of the capsule 324. Here, as the gelling agent, for example, a calcium chloride group may be used. Furthermore, a plasticizer may be further used as a material for forming the film of the capsule 324. As the plasticizer, glycerin and/or sorbitol may be used. Furthermore, a coloring agent may be further used as a material for forming the film of the capsule 324.

For example, as a flavoring material included in the content liquid of the capsule 324, menthol, plant essential oil, and the like may be used. As a solvent of the flavoring material included in the content liquid, for example, a medium chain fatty acid triglyceride (MCT) may be used. Also, the content liquid may include other additives like a figment, an emulsifying agent, a thickening agent, etc.

The cooling structure 322 cools aerosol generated as the heater 130 heats the tobacco rod 310. Therefore, a user may inhale aerosol cooled to a suitable temperature.

The cooling structure 322 may cool aerosol by using the phase change phenomenon. For example, a material constituting the cooling structure 322 may cause a phase change action, such as melting or glass transition that needs absorption of thermal energy. As such a heat-absorbing reaction occurs at a temperature at which aerosol enters the cooling structure 322, the temperature of the aerosol passing through the cooling structure 322 is dropped.

The length or the diameter of the cooling structure 322 may vary depending on the shape of the cigarette 3. For example, the length of the cooling structure 322 may be suitably selected within the range from 7 mm to 20 mm. Preferably, the length of the cooling structure 322 may be about 14 mm, but is not limited thereto.

The cooling structure 322 may be fabricated using a polymer material or a biodegradable polymer material. For example, the polymer material includes, but is not limited to, gelatin, polyethylene (PE), polypropylene (PP), polyurethane (PU), fluorinated ethylene propylene (FEP), and combinations thereof. Also, the biodegradable polymeric material includes, but is not limited to, polylactic acid (PLA), polyhydroxybutyrate (PHB), cellulose acetate, poly-epsilon-caprolactone (PCL), polyglycolic acid (PGA), polyhydroxyaikanoate (PHAs), and starch-based thermoplastic resins.

Preferably, the cooling structure 322 may include pure polylactic acid only. For example, the cooling structure 322 may be a 3-dimensional structure fabricated using at least one fiber strand including pure polylactic acid (hereinafter referred to as a 'fiber strand'). Here, the thickness of the fiber strand, the length of the fiber strand, the number of fiber strands constituting the cooling structure 322, and the shape of the fiber strand may vary. As the cooling structure 322 is made of pure polylactic acid, certain materials may be prevented from being formed while aerosol passes through the cooling structure 322.

The cooling structure 322 may be fabricated through one or more operations, and an operation for wrapping the outer surfaces of the cooling structure 322 with a wrapper made of paper or a polymer material may be added. Here, the polymer material includes, but is not limited to, gelatin, polyethylene (PE), polypropylene (PP), polyurethane (PU), fluorinated ethylene propylene (FEP), and combinations thereof.

Hereinafter, with reference to FIGS. 24A to 25, examples of a fiber strand and a fiber bundle Including a plurality of fiber strands will be described.

Figure 24A:
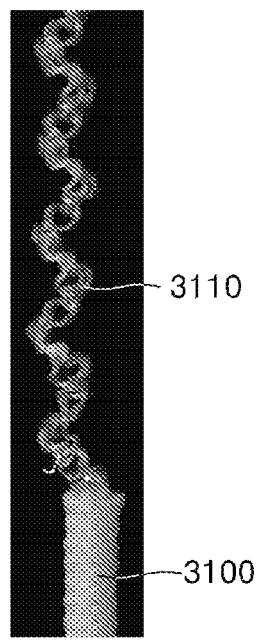
FIGS. 24A and 24B are diagrams for describing examples of a fiber bundle.
Figure 24B:
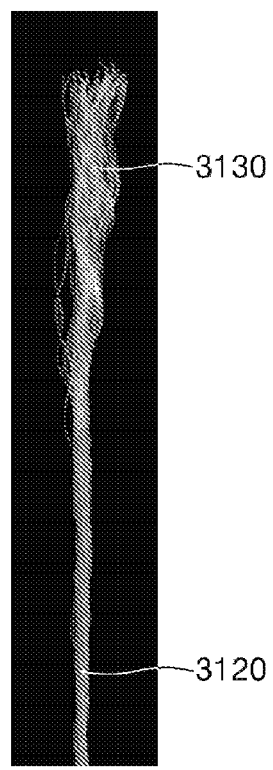

FIGS. 24A and 24B are diagrams for describing examples of a fiber bundle.

FIGS. 24A and 24B show examples of a fiber bundle constituting a cooling structure. Referring to FIG. 24A, a cooling structure 3100 may be fabricated by weaving at least one fiber bundle 3110. Referring to FIG. 248, one fiber bundle 3120 may include at least one fiber strand 3130. For example, one fiber bundle 3120 may be formed by twisting a plurality of fiber strands (e.g., 40 fiber strands).

The cooling structure 322 may be fabricated by weaving at least one fiber bundle 3110 and/or 3120. As occasions demand, the fiber bundles 3110 and 3120 may be formed by using fiber strands coated with a flavoring liquid. Alternatively, the fiber bundles 3110 and 3120 may be formed by using a separate fiber strand coated with a flavoring liquid and fiber strands 3130 made of polylactic acid. In addition, the fiber strands 3130 may be dyed to a predetermined color, and the fiber bundles 3110 and 3120 may be formed by using the dyed fiber strands 3130.

The advantages of fabricating the cooling structure 3100 by using the fiber bundles 3110 and 3120 are as follows.

First, aerosol may flow between the fiber strands 3130 and a vortex may be formed depending on the shape of the cooling structure 3100. The vortex expands an area of contact of the aerosol in the cooling structure 3100 and increases the time that the aerosol stays in the cooling structure 3100. Therefore, heated aerosol may be effectively cooled.

Figure 27A:
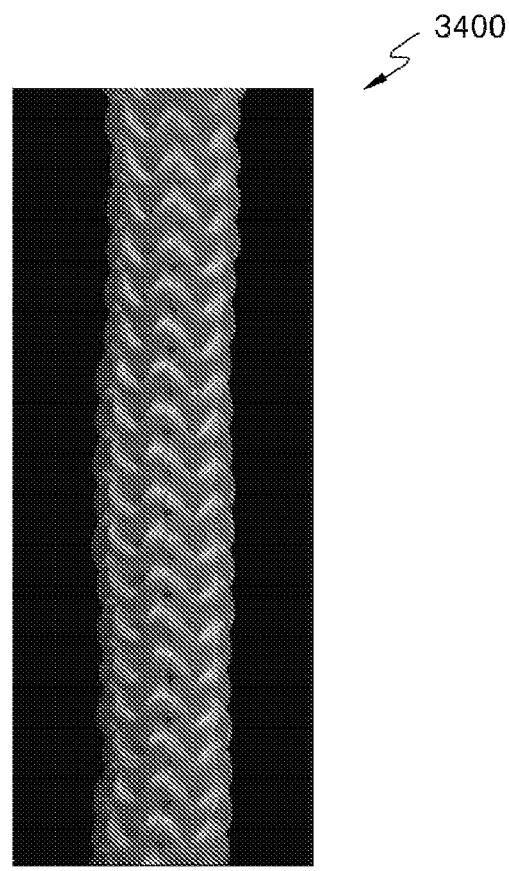
FIGS. 27A to 27C are diagrams for describing another example of a cooling structure including a single vertical channel.

Second, the cooling structure 3100 manufactured by using the fiber strands 3130 fabricated by using a raw material (e.g., polylactic acid) has a high yield relative to a typical prosthetic material. In other words, the cooling structure 3100 made of the fiber strands 3130 is easier to cut than a general prosthetic material. Therefore, since a large number of the cooling structures 3100 may be obtained by cutting a single cooling rod, the manufacturing yield is high as compared to the process for producing a prosthetic material.

Also, when a cooling structure is manufactured through extrusion molding or the like, the efficiency of the process is lowered due to the addition of operations like cutting of a structure. Also, there are limits in manufacturing a cooling structure in various shapes.

Third, the cooling structure 3100 manufactured by using the fiber strands 3130 facilitates cigarette production as compared to a film-type cooling structure. In other words, since a film-type cooling structure is easily crushed, it is difficult to insert the film-type cooling structure into the cigarette 3 having a small volume. On the other hand, the cooling structure 3100 manufactured by using fiber strands may be easily inserted into the cigarette 3.

Also, in case of inserting a film-type cooling structure into the cigarette 3, the film-type cooling structure may be crushed by an external impact. In this case, the aerosol cooling effect of the cooling structure is deteriorated.

As the cooling structure 3100 according to an embodiment is fabricated by using polylactic acid fibers (e.g., weaving), the risk of the cooling structure being deformed or losing function by an external impact may be reduced. Also, by changing the way of combining the fiber bundles 3110 and 3120, the cooling structure 3100 having various shapes may be fabricated.

Furthermore, by fabricating the cooling structure 3100 by using cooling fibers 3130, the surface area contacting with aerosol is increased. Therefore, the aerosol cooling effect of the cooling structure 3100 may be further improved.

FIG. 25 is a diagram for describing another example of a fiber bundle.

Referring to FIG. 25, a fiber bundle 3200 may Include one main stream 3210 and a plurality of sub streams 3220. Here, the main stream 3210 may include a plurality of fiber strands tangled with one another. Also, the sub stream 3220 is at least one fiber strand coupled with a space formed in the main stream 3210, and thus the fiber bundle 3200 may have a shape similar to a wing of a bird.

The number of fiber strands constituting main stream 3210 or sub stream 3220 is not limited. Therefore, the thickness of the main stream 3210 or the sub stream 3220 may vary according to the number of fiber strands.

Also, the sub streams 3220 connected to the main stream 3210 may not be aligned in any one direction. In other words, when the plurality of sub streams 3220 are included in the main stream 3210, orientations of the sub streams 3220 may be different from one another, or orientations of some of the sub streams 3220 may be different from one another.

Referring back to FIGS. 23A and 23B, at least one channel may be included in the cross-section of the cooling structure 322. The channel serves as a passage through which aerosol may pass. However, the direction of the channel is not limited to the vertical direction (i.e., the axial direction of the cooling structure 322), and channels may be formed in various directions.

Depending on the fabrication process of the cooling structure 322, the diameter of the channel may vary. For example, the diameter of the channel may be adjusted according to the thickness and/or the number of a fiber bundle constituting the cooling structure 322, or the diameter of the channel may be adjusted according to the woven pattern of the cooling structure 322.

Also, uniform channels may be distributed in the cooling structure 322. In other words, the cooling structure 322 may be fabricated, such that channels are uniformly distributed throughout cross-sections. Therefore, aerosol passing through the cooling structure 322 may flow smoothly.

Hereinafter, an example of the cooling structure 322 including a single vertical channel will be described with reference to FIGS. 26A to 28B.

FIGS. 26A and 26B are diagrams for describing an example of a cooling structure including a single vertical channel.

Referring to FIG. 26A, a cooling structure 3300 may have a cylindrical shape. For example, the cooling structure 3300 may be cylindrical shape with a filter including a single channel 3310. Also, FIG. 26B is a cross-sectional view of the cooling structure 3300 shown in FIG. 26A. In FIG. 26B, a hollowness 3320 of the cooling structure 3300 corresponds to a channel.

FIGS. 27A to 27C are diagrams for describing another example of a cooling structure including a single vertical channel.

FIGS. 27A to 27C show an example of a cooling structure 3400 fabricated by weaving a plurality of fiber bundles. Here, a fiber bundle refers to at least one fiber strand that is woven or tangled. In detail, FIGS. 27A to 27C show cross-sections at different positions of the cooling structure 3400 shown in FIG. 27A. A hollowness 3410 shown in FIG. 27B and a hollowness 3420 shown in FIG. 27C correspond to channels.

For example, the number of fiber bundles constituting the cooling structure 3400 may be two or greater, and the number of the fiber bundles is not limited. Also, the number of fiber strands included in a single fiber bundle may be one or greater, and the number of the fiber strands is not limited. Also, the number of fiber strands included in respective fiber bundles may be the same or may differ.

Figure 27B:
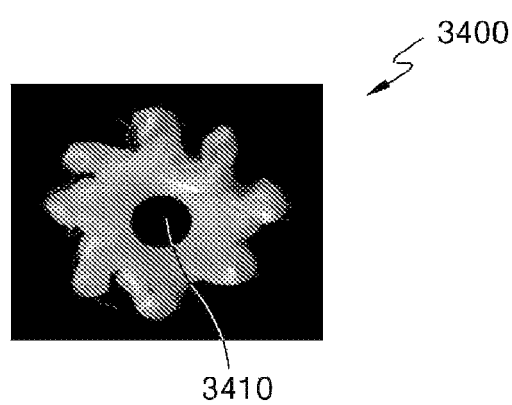
Figure 27C:
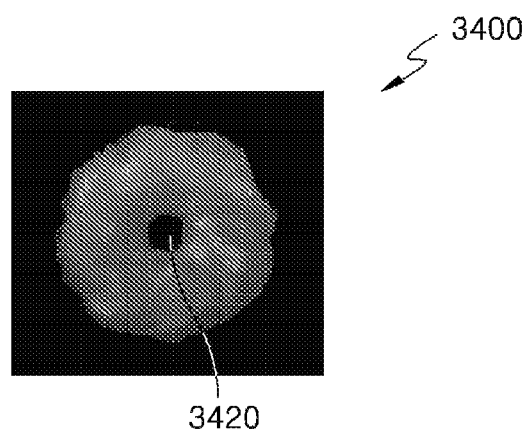

Although FIG. 27B shows that the cooling structure 3400 is fabricated by using eight fiber bundles, but the present disclosure is not limited thereto. For example, the cooling structure 3400 may be fabricated by using six or nine fiber bundles.

Figure 28A:
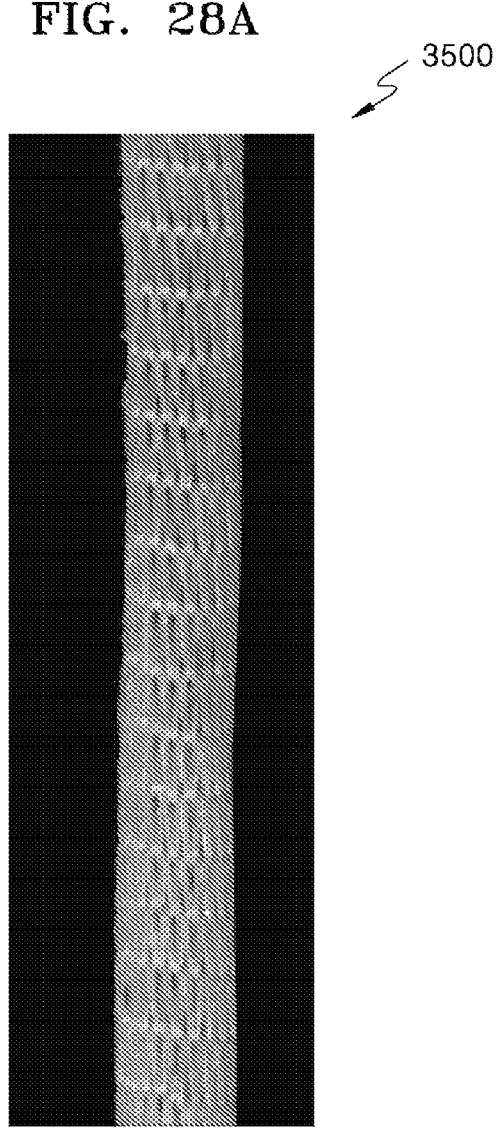
FIGS. 28A and 28B are diagrams for describing another example of a cooling structure including a single vertical channel.
Figure 28B:
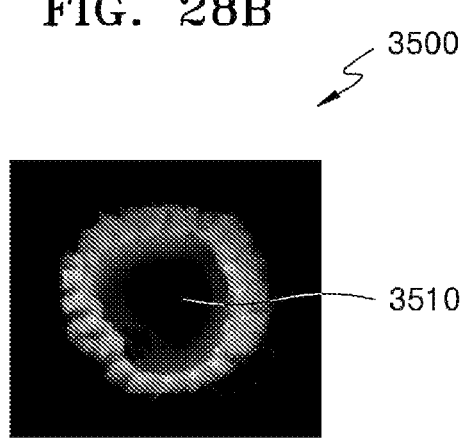

FIGS. 28A and 28B are diagrams for describing another example of a cooling structure including a single vertical channel.

FIGS. 28A and 28B show an example of a cooling structure 3500 fabricated by weaving a plurality of fiber bundles. In detail, FIG. 28B shows a cross-section of the cooling structure 3500 shown in FIG. 28A. For example, the cooling structure 3500 shown in FIGS. 28A and 28B and the cooling structure 1600 shown in FIGS. 28A and 28B may have different hardnesses. Also, a hollowness 3510 shown in FIG. 288 corresponds to a channel.

Meanwhile, the interiors of the channels of the cooling structures 3300, 3400, and 3500 shown in FIGS. 26A to 28B may be filled with a predetermined material (e.g., a sheet fabricated by using polylactic acid, other structures fabricated by using fiber strands, crimped fiber strands, etc.). Furthermore, depending on the fabrication processes of the cooling structures 3300, 3400, and 3500, the degree to which a predetermined material fills a channel (filling rate) may vary.

The number of fiber strands filling the interiors of the cooling structure 3300, 3400, and 3500 may be adjusted for various purposes, and various modifications may be made in the shape of the cooling structure 3300, 3400, and 3500. For example, various types of the cooling structures 3300, 3400, and 3500 may be fabricated by changing the total area of fibers or the arrangement of fiber strands.

Hereinafter, referring to FIGS. 29 to 31, an example in which the interiors of the cooling structures 3300, 3400, and 3500 are filled with a predetermined material (e.g., other cooling structures) will be described.

Figure 29:
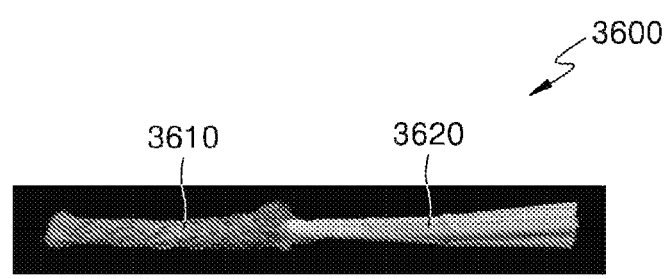
FIG. 29 is a diagram for describing an example of a cooling structure of which the interior is filled.

FIG. 29 is a diagram for describing an example of a cooling structure of which the interior is filled.

FIG. 29 shows an example of a cooling structure 3600 in which a second sub-structure 3620 fills the interior of a first sub-structure 3610. Here, the first sub-structure 3610 may be a cooling structure including at least one channel. For example, the first cooling structure 3610 may be, but is not limited to, the cooling structure 3300, 3400, or 3500 described above with reference to FIGS. 26A to 28B. In other words, the first sub-structure 3610 may be fabricated by weaving at least one fiber strand or at least one fiber bundle.

The at least one channel formed in the first sub-structure 3610 may be filled with the second sub-structure 3620. For example, FIG. 29 shows a crimped sheet-type filter as the second sub-structure 3620. The sheet-type filter will be described below with reference to FIG. 35.

Figure 30A:
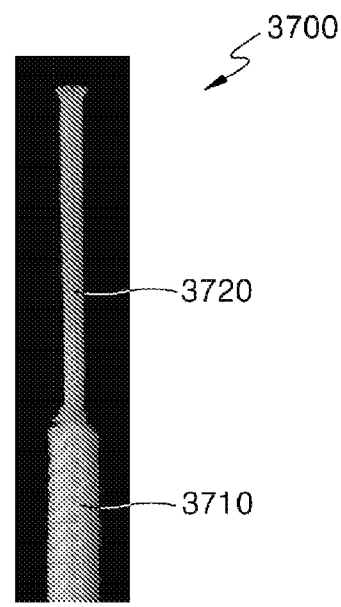
FIGS. 30A and 30B are diagrams for describing another example of a cooling structure of which the interior is filled.
Figure 30B:
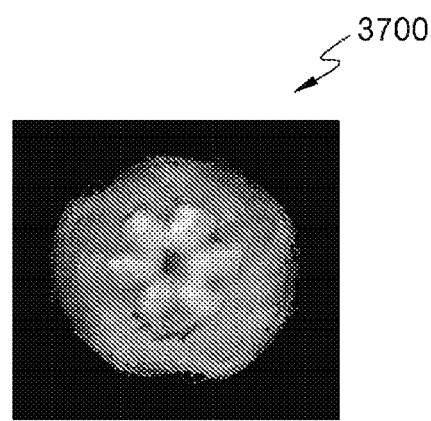

FIGS. 30A and 30B are diagrams for describing another example of a cooling structure of which the interior is filled.

FIGS. 30A and 30B show an example of a cooling structure 3700 in which a second sub-structure 3720 fills the interior of a first sub-structure 3710. FIG. 30B shows a cross-section of the cooling structure 3700 shown in FIG. 30A. The first sub-structure 3710 may be a cooling structure including at least one channel. For example, the first cooling structure 3710 may be, but is not limited to, the cooling structure 3300, 3400, or 3500 described above with reference to FIGS. 26A to 28B.

The second sub-structure 3720 filling the channel of the first sub-structure 3710 may be a structure fabricated by weaving a plurality of fiber bundles. For example, the diameter of the second sub-structure 3720 may be equal to the diameter of the channel of the first sub-structure 3710, and thus the second sub-structure 3720 may fill the channel of the first sub-structure 3710. Also, although FIGS. 30A and 30B show that there is only one second sub-structure 3720, the present disclosure is not limited thereto. In other words, depending on the diameter of the second sub-structure 3720, the channel of the first sub-structure 3710 may be filled with a plurality of second sub-structures 3720.

Figure 31:
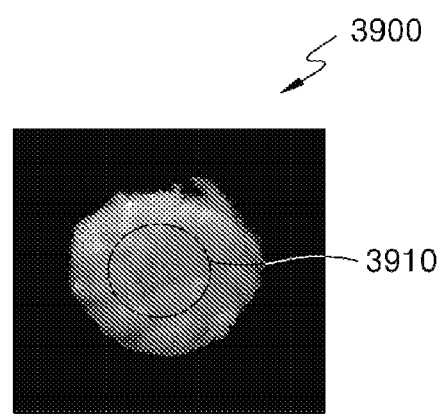
FIG. 31 is a diagram for describing another example of a cooling structure of which the interior is filled.

FIG. 31 is a diagram for describing another example of a cooling structure of which the interior is filled.

A cooling structure 3900 shown in FIG. 31 may have the same structure as those of the cooling structures 3600 and 3700 shown in FIGS. 29 to 30B. In other words, the cooling structure 3900 may have a structure in which a channel 3910 of a first sub-structure is filled with a different material. For example, the channel 3910 may be filled with a plurality of fiber strands. At this time, the fiber strands may have an irregularly tangled shape (e.g., a cotton-like shape), but the present disclosure is not limited thereto.

As described above with reference to FIGS. 26A to 31, a cooling structure may include a single vertical channel. However, the present disclosure is not limited thereto. In other words, to increase the surface area per unit area (i.e., the surface area contacting aerosol), the cooling structure may include a plurality of channels, and the number of the channels is not limited. Hereinafter, a cooling structure including a plurality of channels will be described with reference to FIGS. 32A to 34E.

Figure 32A:
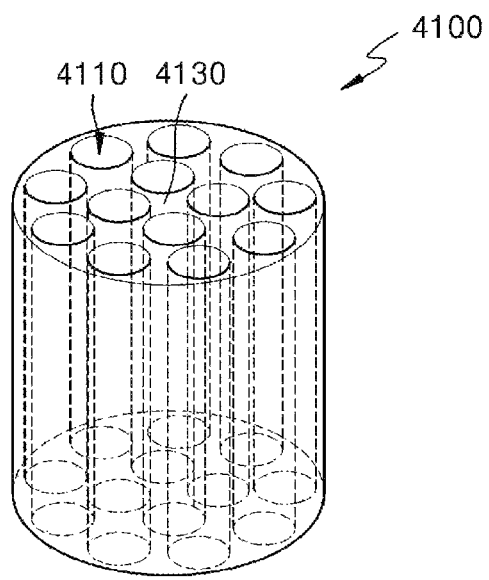
FIGS. 32A and 32B are diagrams for describing an example of a cooling structure including a plurality of channels.
Figure 32B:
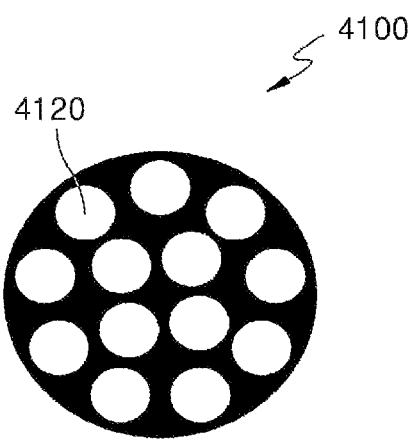

FIGS. 32A and 32B are diagrams for describing an example of a cooling structure including a plurality of channels.

Referring to FIG. 32A, a cooling structure 4100 may have a cylindrical shape and include a plurality of channels 4110. Although FIGS. 32A and 32B show that the cooling structure 4100 includes 13 channels 4110, but the number of channels is not limited thereto. Also, FIG. 32B is a cross-sectional view of the cooling structure 4100 shown in FIG. 32A. In FIG. 32B, a plurality of hollownesses 4120 of the cooling structure 4100 corresponds to channels, respectively.

Figure 26A:
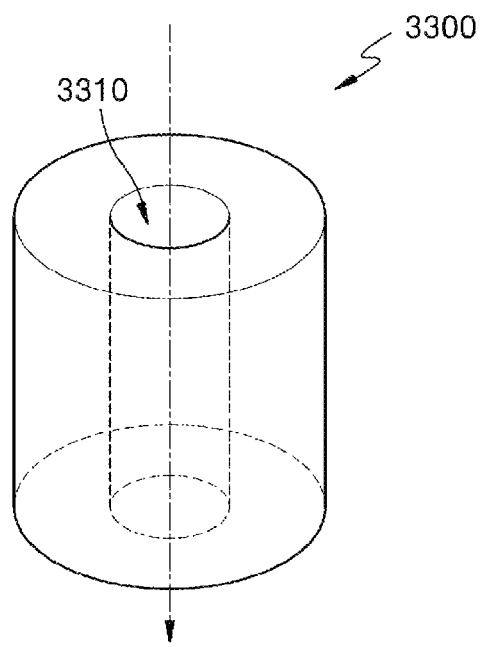
FIGS. 26A and 26B are diagrams for describing an example of a cooling structure including a single vertical channel.
Figure 26B:
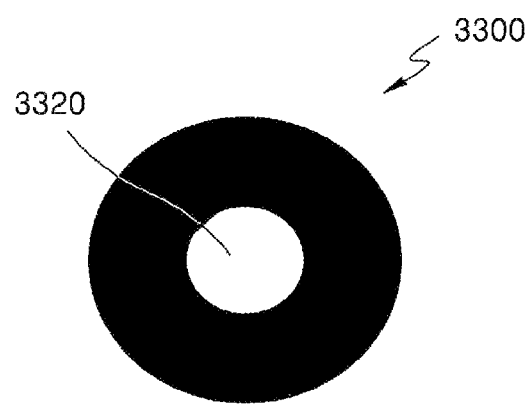

For example, the cooling structure 4100 may be fabricated by grouping a plurality of cooling structures 3300 shown in FIGS. 26A to 26B. In other words, the number of the channels 4110 included in the cooling structure 4100 may be determined according to the number of the cooling structures 3300. However, a method of fabricating the cooling structure 4100 is not limited thereto.

As the cooling structure 4100 is fabricated by grouping the plurality of cooling structures 3300, a space 4130 between the cooling structures 3300 adjacent to each other may also serve as a channel. Therefore, even when any of the plurality of cooling structures 3300 is clogged due to a phase charge, aerosol may easily pass through the cooling structure 4100.

Figure 33:
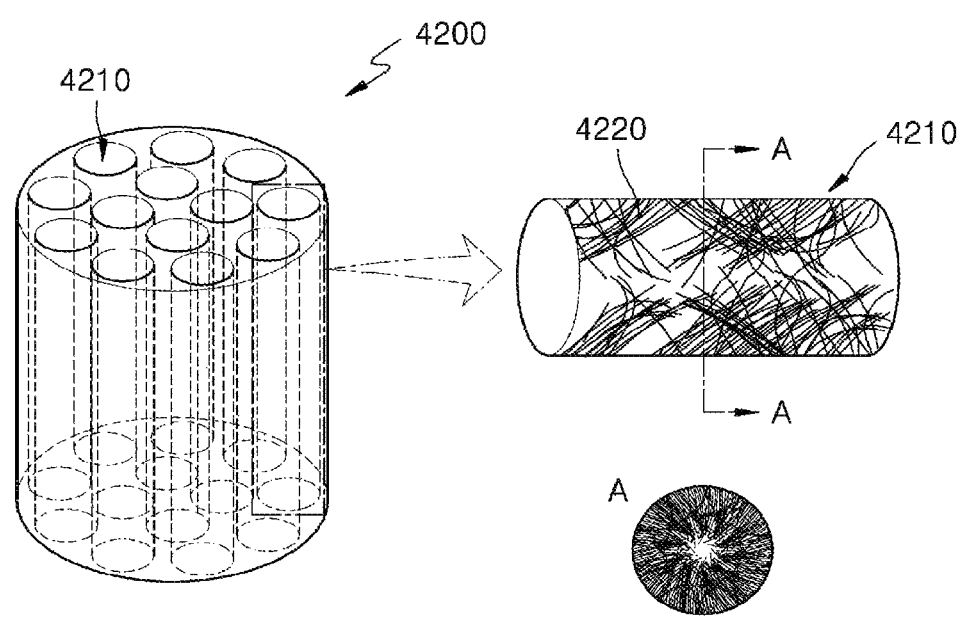
FIG. 33 is a diagram for describing an example in which the Interior of a cooling structure including a plurality of channels is filled.
Figure 34A:
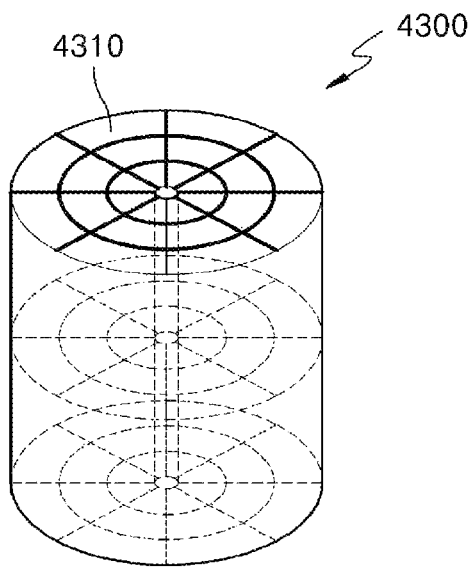
FIGS. 34A to 34E are diagrams for describing another example of a cooling structure including a plurality of channels.
Figure 34B:
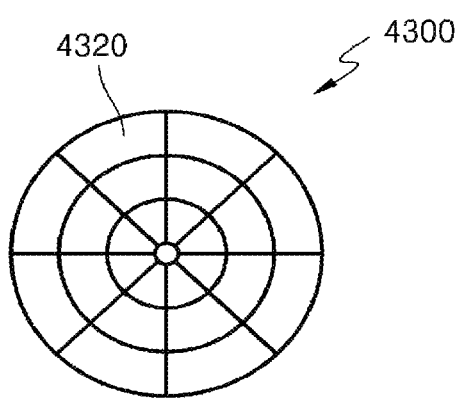
Figure 34C:
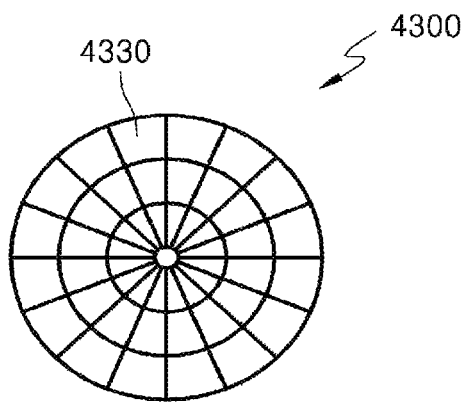
Figure 34D:
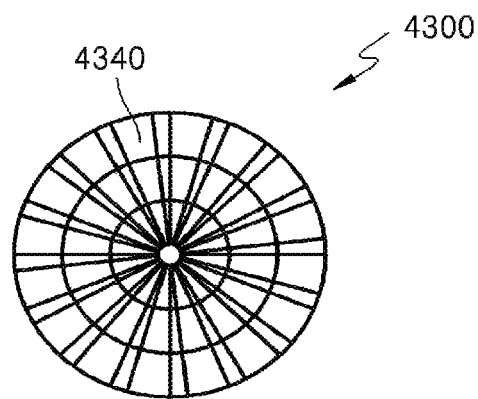
Figure 34E:
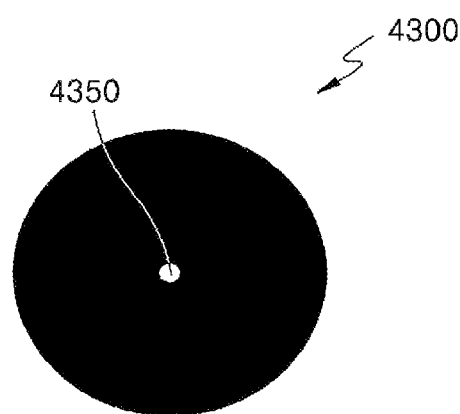
Figure 35:
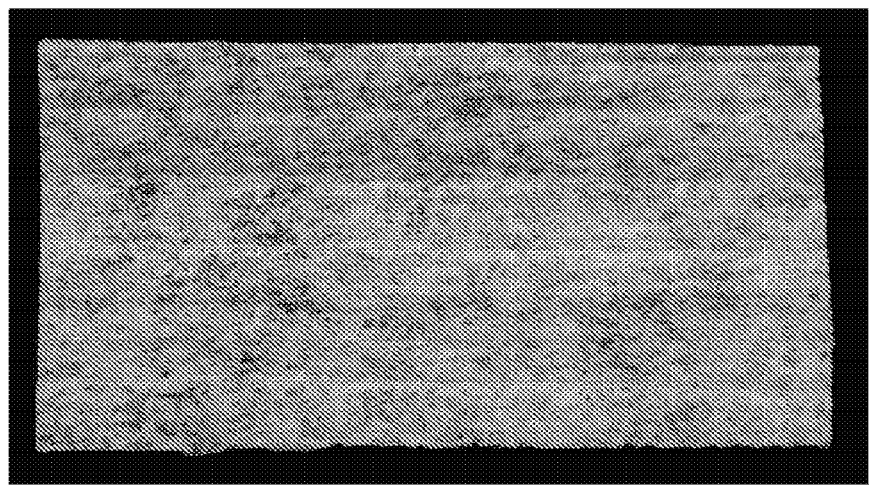
FIG. 35 is a diagram for describing an example of a sheet-type cooling structure.
Figure 36A:
FIGS. 36A and 36B are diagrams for describing another example of a sheet-type cooling structure.
Figure 36B:
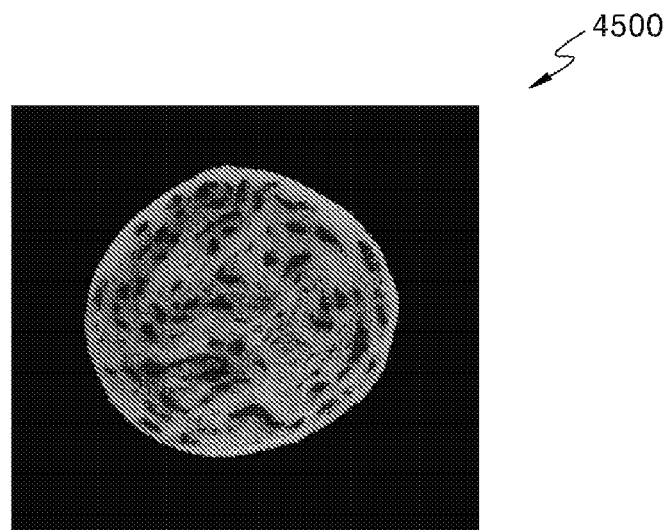
Figure 37:
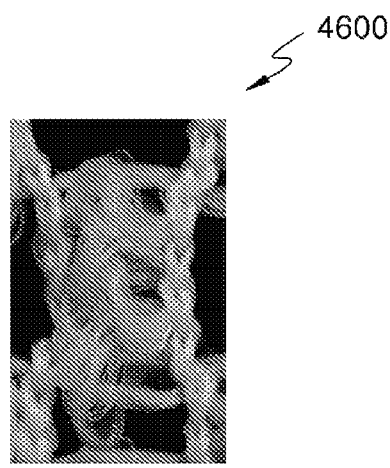
FIG. 37 is a diagram for describing an example of a granular-type cooling structure.
Figure 38A:
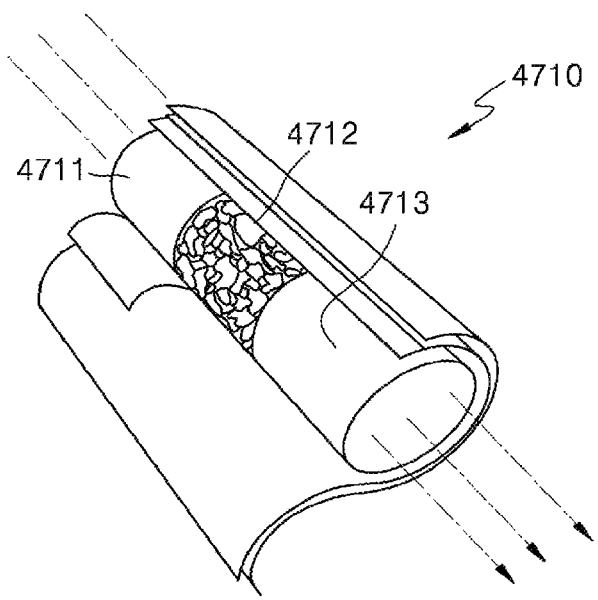
FIGS. 38A to 38C are diagrams for describing an example of a cooling structure fabricated as a prosthetic object.
Figure 38B:
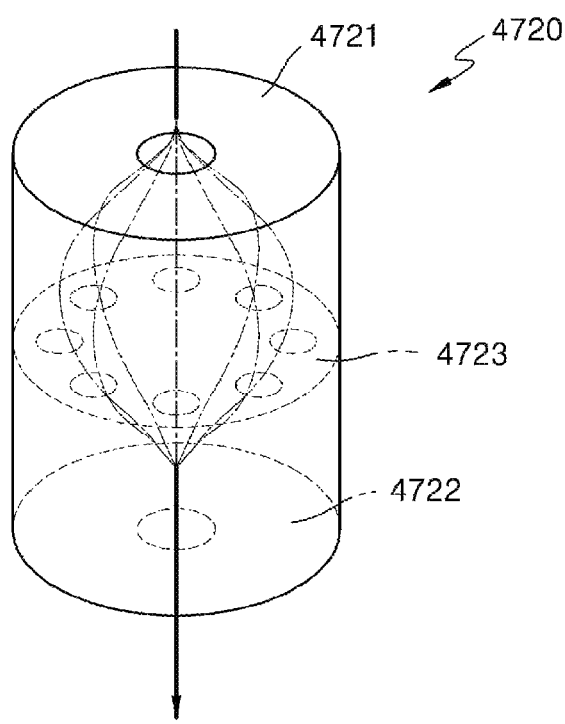
Figure 38C:
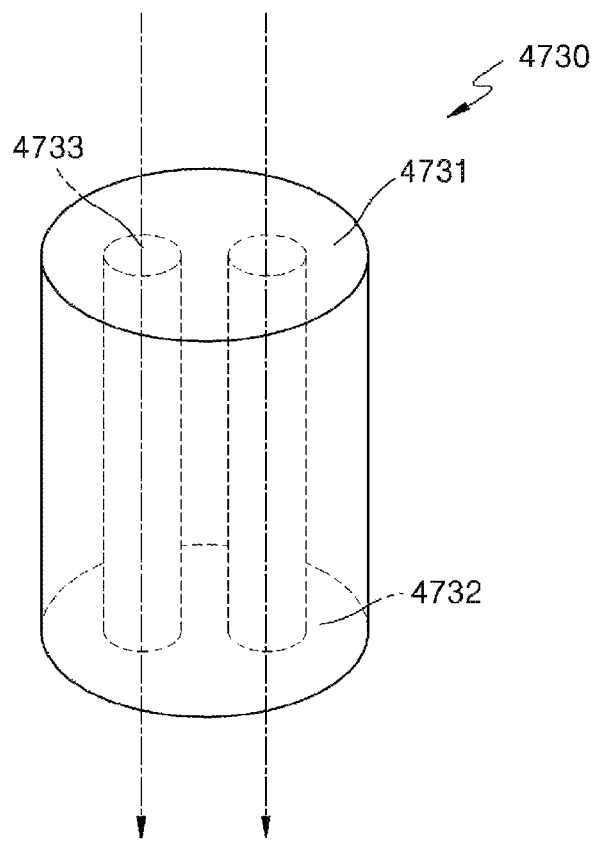

FIG. 33 is a diagram for describing an example in which the interior of a cooling structure including a plurality of channels is filled.

Referring to FIG. 33, a cooling structure 4200 may be formed by grouping a plurality of cooling structures 4210. For example, a cooling structure 4210 may Include one channel and, as the plurality of cooling structures 4210 are grouped, the cooling structure 4200 may include a plurality of channels.

Figure 25:
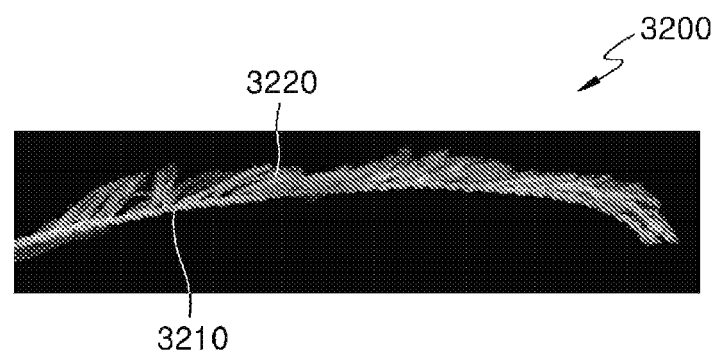
FIG. 25 is a diagram for describing another example of a fiber bundle.

For example, the cooling structure 4120 may be fabricated by using the fiber bundles 3200 shown in FIG. 25. In other words, the cooling structure 4210 is fabricated by weaving the plurality of fiber bundles 3200 and the sub streams 3220 of the fiber bundles 3200 may be located in the channels of the cooling structure 4210. In this case, the cross-sectional area of the cooling structure 4210 contacting aerosol is increased by the sub-streams 3220, and thus the aerosol cooling effect may be further improved.

As described above with reference to FIGS. 32A to 33, a cooling structure may include a plurality of channels having the same shape in the vertical direction.

Meanwhile, a plurality of channels formed in a cooling structure are not limited to those shown in FIGS. 32A to 33. Hereinafter, another example of a cooling structure including a plurality of channels will be described with reference to FIGS. 34A to 34E.

FIGS. 34A to 34E are diagrams for describing another example of a cooling structure including a plurality of channels.

FIGS. 34A to 34E show an example of a cooling structure 4300 including a plurality of channels. In detail, FIGS. 34B to 34E show one cross-section regarding each of various modifications of the cooling structure 4300 shown in FIG. 34A.

Referring to FIG. 34A, each of the cross-sections of the cooling structure 4300 may include a plurality of channels 4310. Also, referring to FIGS. 34B to 34D, the position and/or the size of each of a plurality of channels 4320, 4330, and 4340 may vary depending on the fabrication process of the cooling structure 4300. Also, referring to FIG. 34E, depending on the position of each of a plurality of channels, the entire cooling structure 4300 may be fabricated to include a single continuous airflow path 4350.

As described above with reference to FIGS. 26A to 34E, a cooling structure may be fabricated to Include at least one hollow channel. However, the cooling structure may be fabricated in various shapes other than the shape including a hollowness channel.

For example, the cooling structure may be fabricated in a sheet-like shape. Hereinafter, referring to FIGS. 35 to 36B, an example of a cooling structure fabricated in a sheet-like shape will be described. Alternatively, the cooling structure may be fabricated in a granular shape. Hereinafter, referring to FIG. 37, an example of a cooling structure fabricated in a granular shape will be described. Alternatively, the cooling structure may be fabricated as a prosthetic object formed of polylactic acid (PLA). Hereinafter, referring to FIGS. 38A to 38C, an example of a cooling structure fabricated as a prosthetic object.

Also, through a thermal curing process, cooling structures 322 having various hardness may be produced.

FIG. 35 is a diagram for describing an example of a sheet-type cooling structure.

A cooling structure 4400 may be fabricated in a sheet-type shape (hereinafter referred to as a 'sheet-type cooling structure'). For example, the sheet-type cooling structure 4400 may be fabricated by densely arranging fiber strands without specific directionality and compressing the same, but the present disclosure is not limited thereto.

In addition, a predetermined material (e.g., activated carbon granules) may be inserted into the sheet-type cooling structure 4400. For example, a predetermined material may be applied on a first sheet-type cooling structure, a second sheet-type cooling structure may be placed on a first sheet-type cooling structure, and the first sheet-type cooling structure and the second sheet-type cooling structure may be compressed, and thus the predetermined material may be inserted into the compressed cooling structure 4400. However, the fabrication process of the sheet-type cooling structure 4400 is not limited to the above-described example.

FIGS. 36A and 36B are diagrams for describing another example of a sheet-type cooling structure.

FIGS. 36A and 36B show an example of a cooling structure 4500 of which the interior is filled. In detail, FIG. 36B shows one cross-section of the cooling structure 4500 shown in FIG. 36A. For example, the cooling structure 4500 of FIG. 36A may be fabricated by wrapping the outer surface of a crimped sheet-type cooling structure with another sheet-type cooling structure.

FIG. 37 is a diagram for describing an example of a granular-type cooling structure.

FIG. 37 shows an example of a granular cooling structure 4600 fabricated by using at least one fiber strand or at least one fiber bundle. For example, the cooling structure 4600 may be fabricated by tangling or randomly weaving at least one fiber strand or at least one fiber bundle.

FIGS. 38A to 38C are diagrams for describing an example of a cooling structure fabricated as a prosthetic object.

Referring to FIG. 38A, a cooling structure 4710 may be filled with granules formed of polylactic acid, cut leaves, or charcoal. Also, the granules may be fabricated by using a mixture of polylactic acid, cut leaves, and charcoal. On the other hand, the granules may further Include an element capable of increasing the aerosol cooling effect other than polylactic acid, the cut leaves, and/or charcoal.

Referring to FIG. 38B, a cooling structure 4720 may include a first cross-section 4721 and a second cross-section 4722.

The first cross-section 4721 borders on the first filter segment 321 shown in FIGS. 23A to 23B and may include a gap into which aerosol is introduced. The second cross-section 4722 borders on the second filter segment 323 shown in FIGS. 23A to 23B and may include a gap through which aerosol may be released. For example, each of the first cross-section 4721 and the second cross-section 4722 may include a single gap having the same diameter, but the diameters and the numbers of the gaps included in the first cross-section 4721 and the second cross-section 4722 are not limited thereto.

In addition, the cooling structure 4720 may include a third cross-section 4723 including a plurality of gaps between the first cross-section 4721 and the second cross-section 4722. For example, the diameters of the plurality of gaps included in the third cross-section 4723 may be smaller than the diameters of the gaps included in the first cross-section 4721 and the second cross-section 4722. Also, the number of gaps included in the third cross-section 4723 may be greater than the number of gaps included in the first cross-section 4721 and the second cross-section 4722.

Referring to FIG. 38C, a cooling structure 4730 may include a first cross-section 4731 that borders on the first filter segment 321 and a second cross-section 4732 that borders on the second filter segment 323. Also, the cooling structure 4730 may include one or more channels 4733.

Also, the channel 4733 may be packaged with a microporous packaging material and filled with a filler material (e.g., the granules described above with reference to FIG. 38A) that may increase the aerosol cooling effect.

As described above, the holder 1 may generate aerosol by heating the cigarette 3. Also, aerosol may be generated independently by the holder 1 or even when the holder 1 is inserted into the cradle 2 and is tilted. Particularly, when the holder 1 is tilted, the heater 130 may be heated by power of a battery of the cradle 2.

Hereinafter, an aerosol generating apparatus 10000 according to embodiments shown in FIGS. 39 to 58 is an example of an integral aerosol generating apparatus in which the holder 1 and the cradle 2 in the above-described embodiments are combined. Therefore, the respective embodiments of the holder 1 and the cradle 2 described with reference to FIGS. 1 to 21 may be applied to the aerosol generating apparatus 10000 shown in FIGS. 39 to 58. Also, the cigarette 3 described above with reference to FIGS. 22 to 38C may be inserted into the aerosol generating apparatus 10000 shown in FIGS. 39 to 58, and the aerosol generating apparatus 10000 may heat the cigarette 3 described in FIGS. 22 to 38C and generate aerosol. Also, a heater 10300 of the aerosol generating apparatus 10000 shown in FIGS. 39 to 58 may correspond to the heater 130 shown in FIGS. 1 to 5. In other words, the holder 1 (particularly the heater 130 employed in the holder 1) and the cigarette 3 (particularly the cooling structure 322 employed in the cigarette 3) described in FIGS. 1 to 38C may be applied to the embodiments described in FIGS. 39 to 58.

The reference numerals denoting the components in FIGS. 39 to 58 have been used Independently without being associated with the reference numerals used in FIGS. 1 to 38C. Therefore, it should be understood that the reference numerals denoting the components in FIGS. 1 to 38C and the reference numerals denoting the components in FIGS. 39 to 58 are used to denote different components independent from each other.

Figure 39:
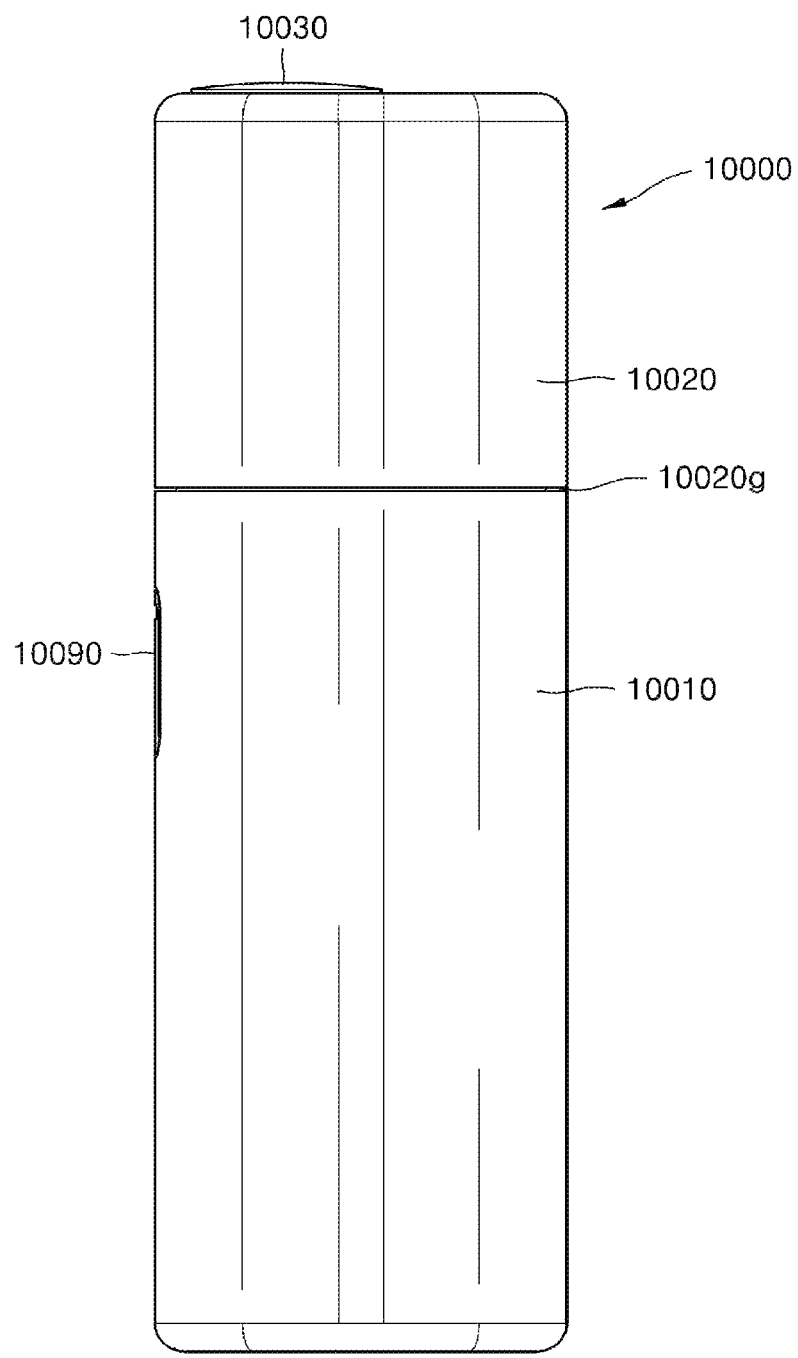
FIG. 39 is a lateral view of an aerosol generating apparatus according to another embodiment.
Figure 40A:
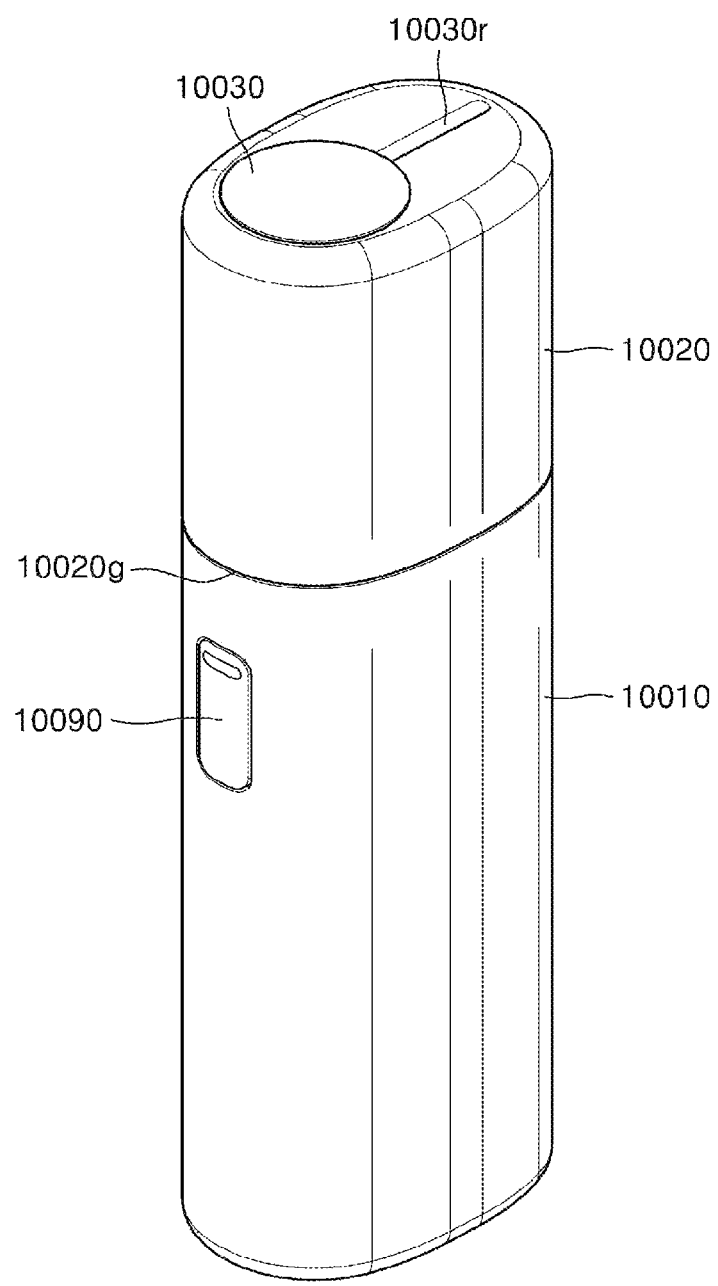
FIG. 40A is a perspective view of the aerosol generating apparatus according to the embodiment shown in FIG. 39.
Figure 40B:
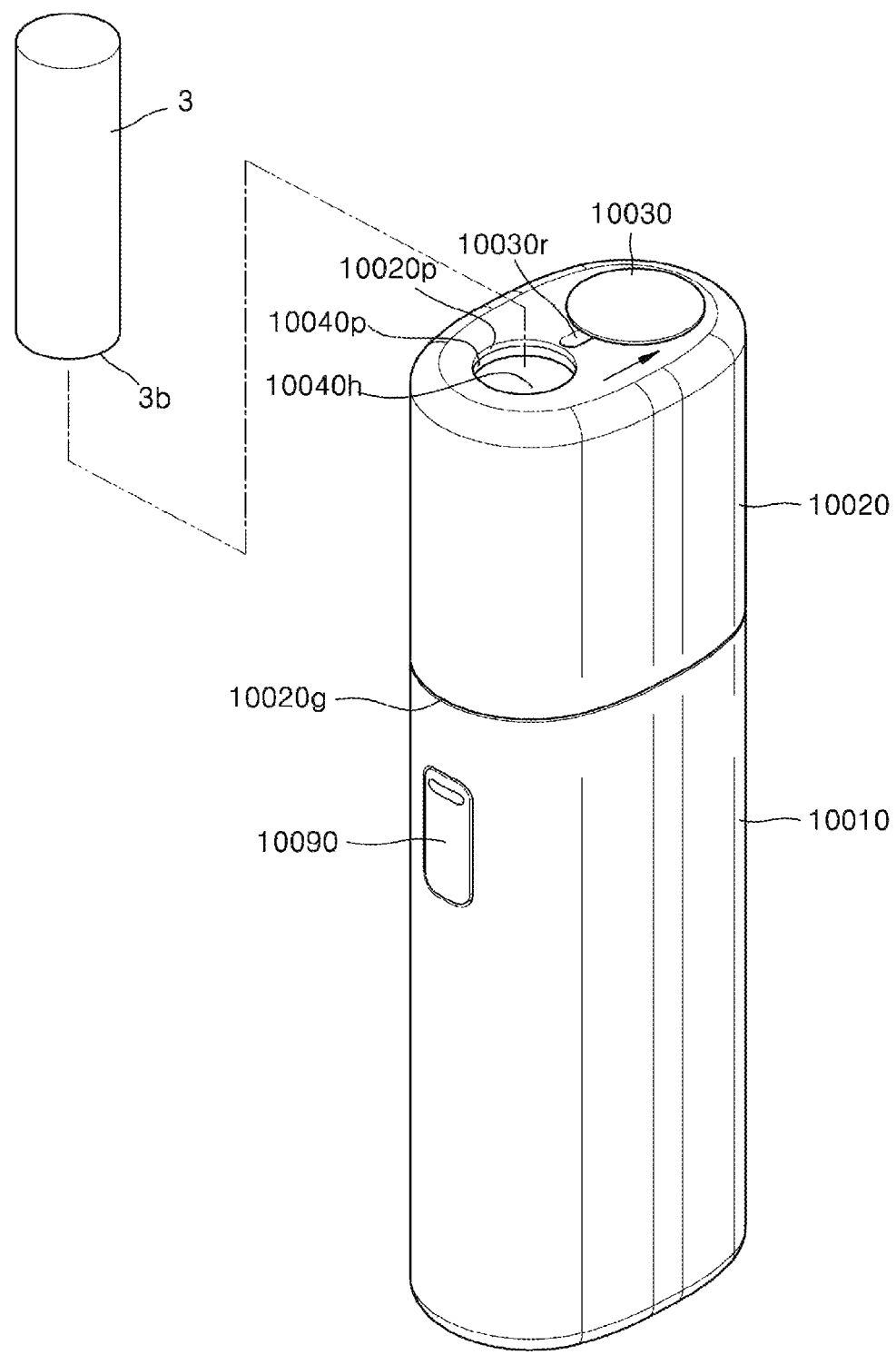
FIG. 40B is a perspective view exemplifying an operating state of the aerosol generating apparatus according to the embodiment shown in FIG. 40A.

FIG. 39 is a lateral view of an aerosol generating apparatus according to another embodiment. FIG. 40A is a perspective view of the aerosol generating apparatus according to the embodiment shown in FIG. 39. FIG. 40B is a perspective view exemplifying an operating state of the aerosol generating apparatus according to the embodiment shown in FIG. 40A.

The aerosol generating apparatus 10000 according to the embodiments shown in FIGS. 39, 40A, and 40B may include a casing 10010 and a cover 10020.

The cover 10020 is coupled with a first end of the casing 10010, and thus the cover 10020 constitutes the outer appearance of the aerosol generating apparatus 10000 together with the casing 10010.

The casing 10010 constitutes the outer appearance of the aerosol generating apparatus 10000 and functions to accommodate and protect various components in a space formed therein.

The cover 10020 and the casing 10010 may include a plastic material with low heat conductivity or a metal coated with a heat barrier material on its surface. The cover 10020 and the casing 10010 may be fabricated through, for example, an injection molding method, a 3D printing method, or a method of assembling small parts fabricated through injection molding.

A locking device may be installed between the cover 10020 and the casing 10010 to maintain the attachment between the cover 10020 and the casing 10010. The locking device may include, for example, a protrusion and a groove.

The attachment between the cover 10020 and the casing 10010 may be maintained by maintaining a state that protrusion is inserted in the groove, and a structure in which the protrusion is moved by a manipulation button that may be pressed by a user and is separated from the groove may also be used.

The locking device may also include, for example, a magnet and a metal member that sticks to the magnet. When a magnet is used for the locking device, a magnet may be installed on either one of the cover 10020 and the casing 10010 and a metal that sticks to the magnet may be attached to the other one. Alternatively, magnets may be installed on both the cover 10020 and the casing 10010.

In the aerosol generating apparatus 10000 according to the embodiment shown in FIGS. 39 and 40A, the cover 10020 is not an essential configuration, and the cover 10020 may not be installed as occasions demand.

An outside hole 10020p through which the cigarette 3 may be inserted is formed on the top surface of the cover 10020 coupled with the casing 10010. Also, a rail 10030r is formed on the top surface of the cover 10020 at a position adjacent to the outside hole 10020p. A door 10030 slidable along the top surface of the cover 10020 is installed on the rail 10030r. The door 10030 may slide in a straight line along the rail 10030r.

As the door 10030 moves along the rail 10030r in the direction indicated by the arrow in FIG. 408, the outside hole 10020p and an insertion hole 10040p that enable the cigarette 3 to be inserted into the casing 10010 through the cover 10020 are exposed to the outside. The outside hole 10020p of the cover 10020 exposes the insertion hole 10040p of an accommodating path 10040h capable of accommodating the cigarette 3 to the outside.

When the outside hole 10020p is exposed to the outside by the door 10030, a user may insert an end portion 3b of the cigarette 3 into the outside hole 10020p and the insertion hole 10040p, thereby placing the cigarette 3 in the accommodating path 10040h formed inside the housing 10020.

In the embodiment, the door 10030 is installed to move in a straight line with respect to the cover 10020. However, the embodiment is not limited by the structure in which the door 10030 is coupled with the cover 10020. For example, the door 10030 may be rotatably mounted on the cover 10020 through a hinge assembly. In case of employing a hinge assembly, the door 10030 may be rotated toward a side surface of the outside hole 10020p in a direction in which the top surface of the cover 10020 extends or the door 10030 may be rotated in a direction away from the top surface of the cover 10020.

The rail 10030r has a concave groove shape, but the embodiment is not limited by the shape of the rail 10030r. For example, the rail 10030r may have a convex shape or may extend in a curved shape instead of a straight shape.

At the casing 10010, a button 10090 is provided. As the button 10090 is manipulated, the operation of the aerosol generating apparatus 10000 may be controlled.

An outside air introduction gap 10020g that allows the air to flow into the interior of the cover 10020 is formed at a portion where the cover 10020 contact the casing 10010 when the cover 10020 is coupled with the casing 10010.

Figure 41A:
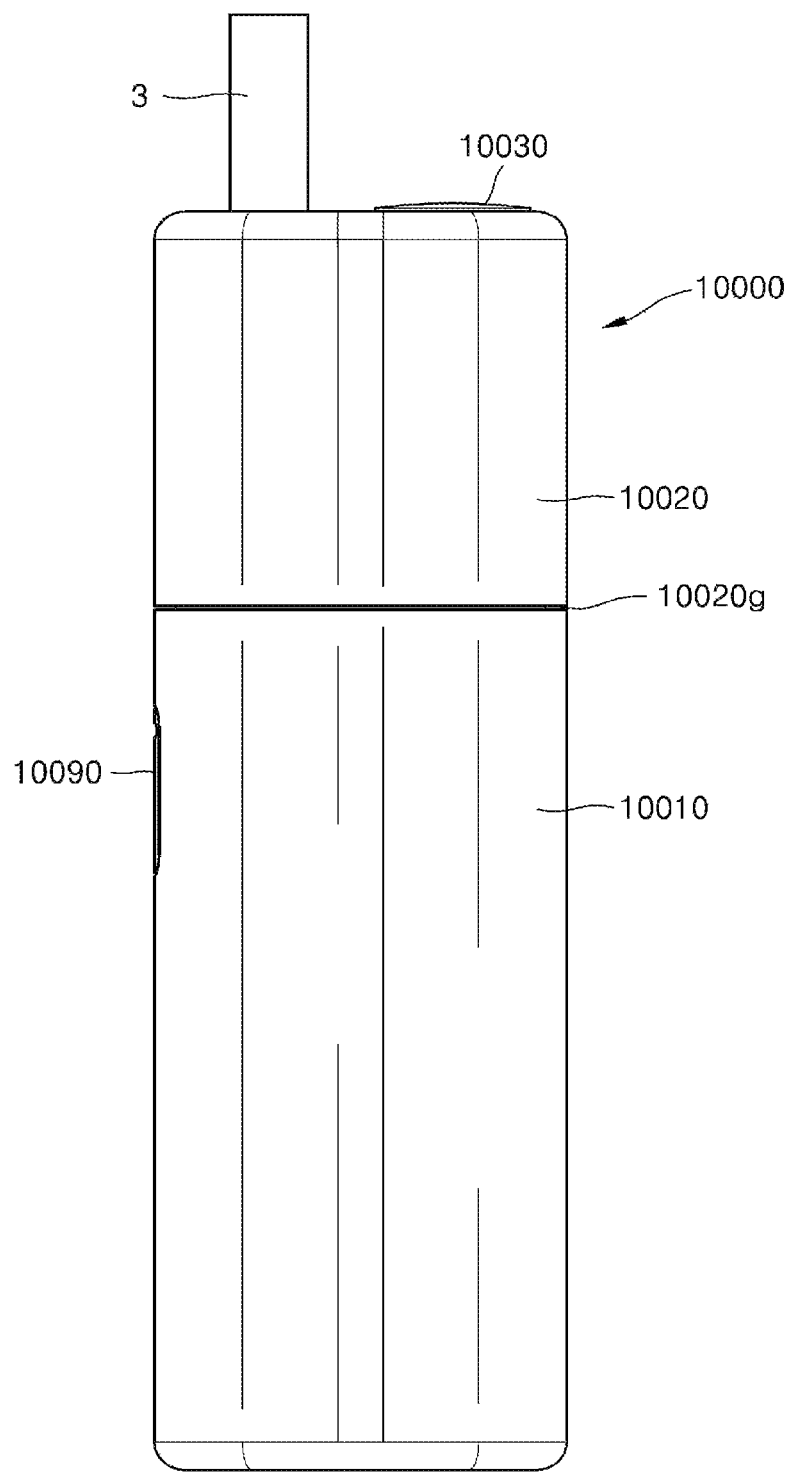
FIG. 41A is a lateral view exemplifying another operating state of the aerosol generating apparatus according to the embodiment shown in FIG. 40A.

FIG. 41A is a lateral view exemplifying another operating state of the aerosol generating apparatus according to the embodiment shown in FIG. 40A.

As shown in FIG. 41A, while the cigarette 3 is being Inserted into the aerosol generating apparatus, a user may inhale aerosol by holding the cigarette 3 between his/her lips.

When separating the cigarette 3 from the aerosol generating apparatus after using the cigarette 3, the user may hold and rotate the cigarette 3 by hand, thereby pulling the cigarette 3 out from a heater inside the aerosol generating apparatus that is inserted into the cigarette 3.

Figure 41B:
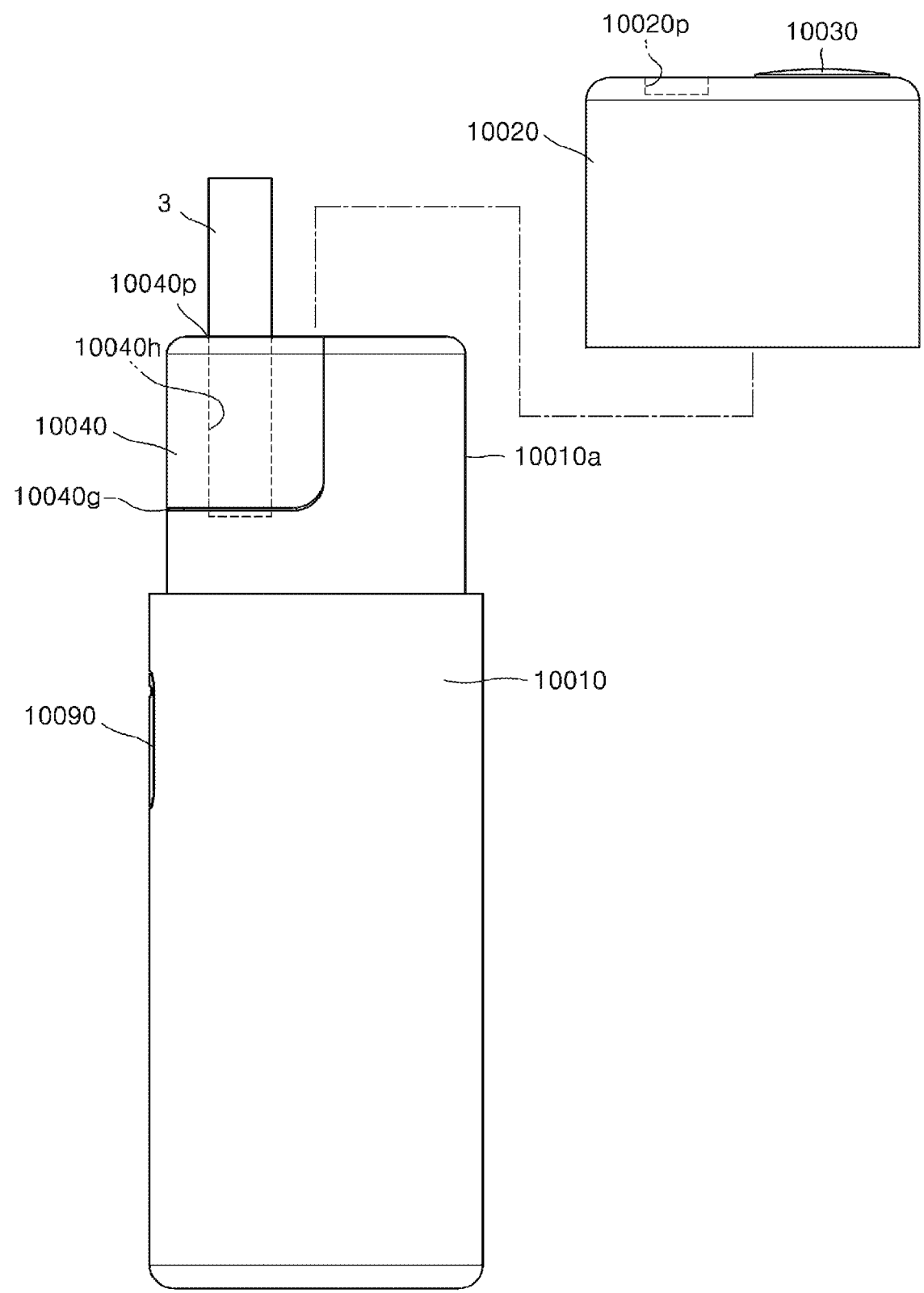
FIG. 41B is a lateral view exemplifying another operating state of the aerosol generating apparatus according to the embodiment shown in FIG. 40A.

FIG. 41B is a lateral view exemplifying another operating state of the aerosol generating apparatus according to the embodiment shown in FIG. 40A.

After the cigarette 3 is separated from the aerosol generating apparatus, the user may carry out a cleaning operation to remove any tobacco material that may be remaining inside the aerosol generating apparatus.

The cleaning operation of the aerosol generating apparatus may be performed by separating the cover 10020 from the casing 10010 of the aerosol generating apparatus 10000, separating the accommodating portion 10040 from the casing 10010 to expose the inner space of the aerosol generating apparatus 10000 and the heater to the outside, and removing a tobacco material therefrom. The cover 10020 may be coupled with a first end portion 10010a of the casing 10010 to cover the accommodating portion 10040 coupled with the first end portion 10010a of the casing 10010 and may be separated from the casing 10010 as occasions demand.

Figure 42:
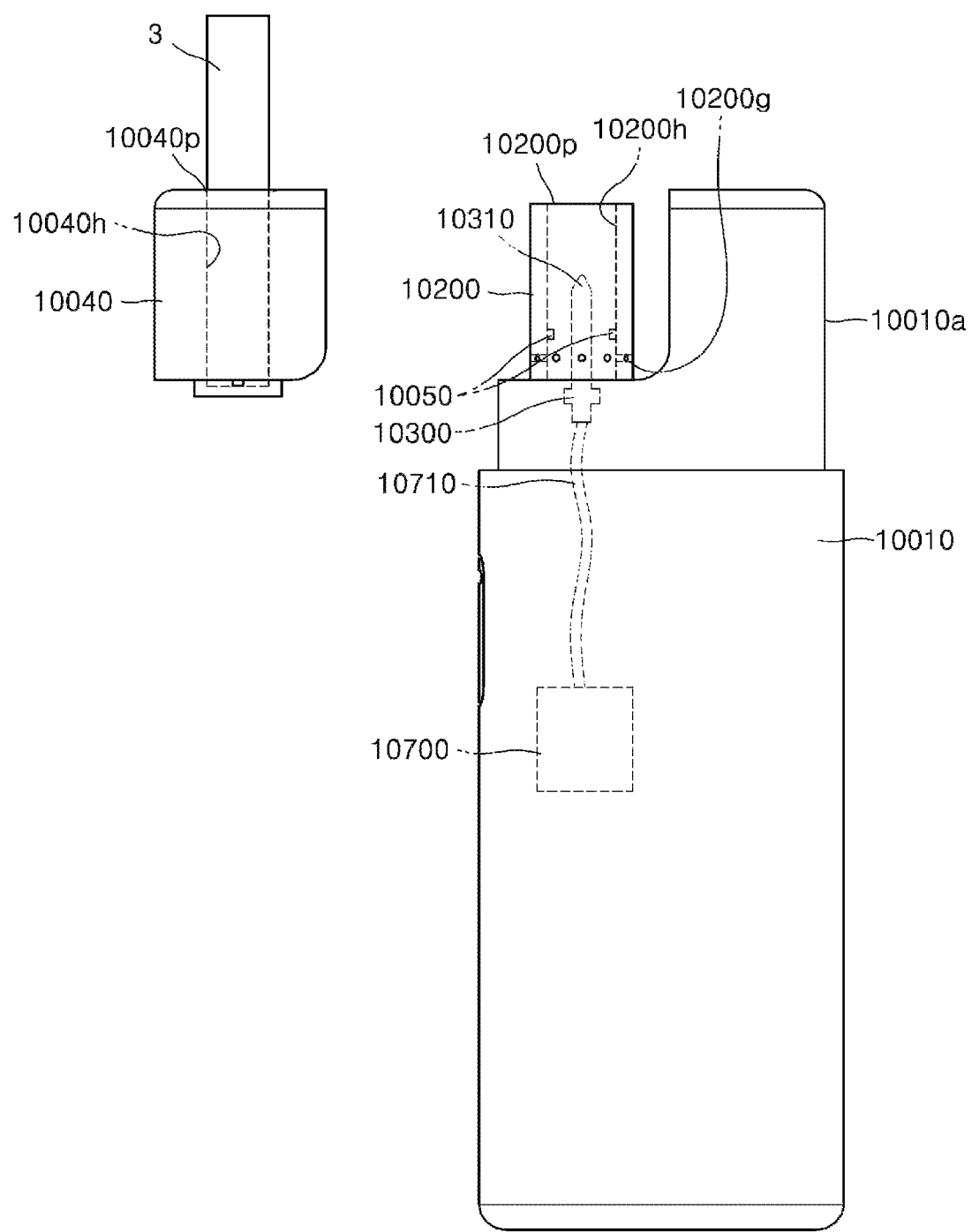
FIG. 42 is a lateral view exemplifying another operating state of the aerosol generating apparatus according to the embodiment shown in FIG. 40A.
Figure 43:
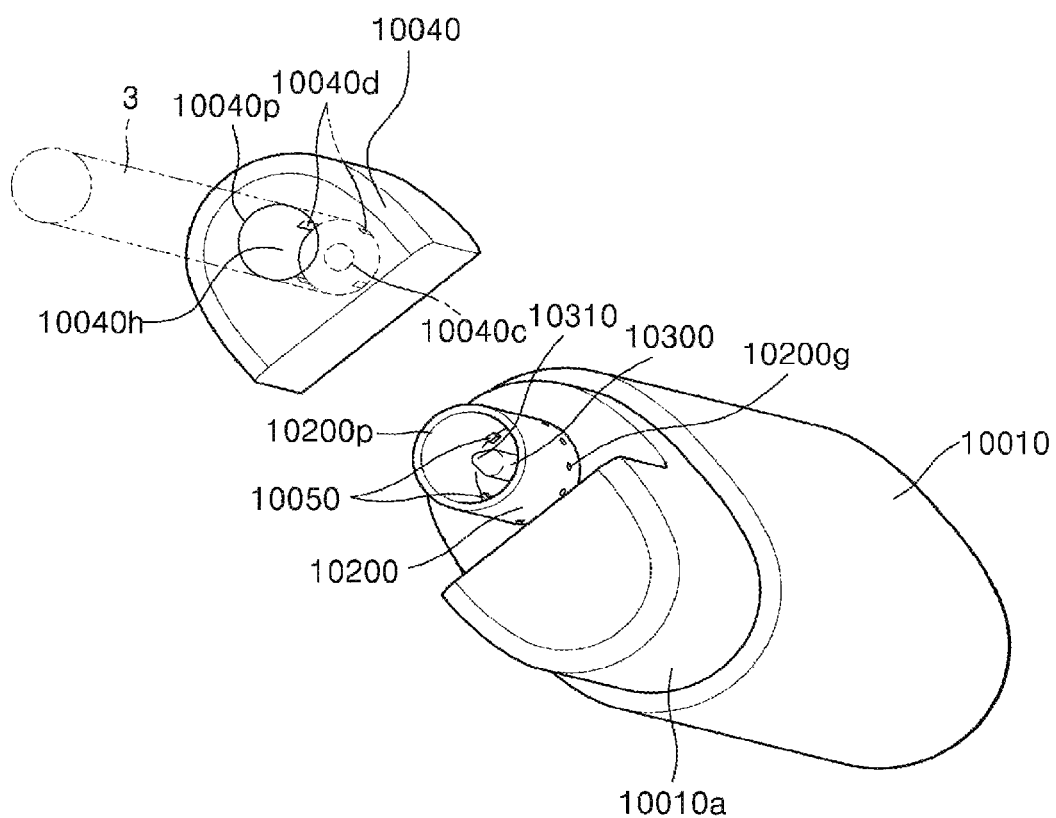
FIG. 43 is a perspective view of the aerosol generating apparatus according to the embodiment shown in FIG. 42 viewed at another angle.
Figure 44:
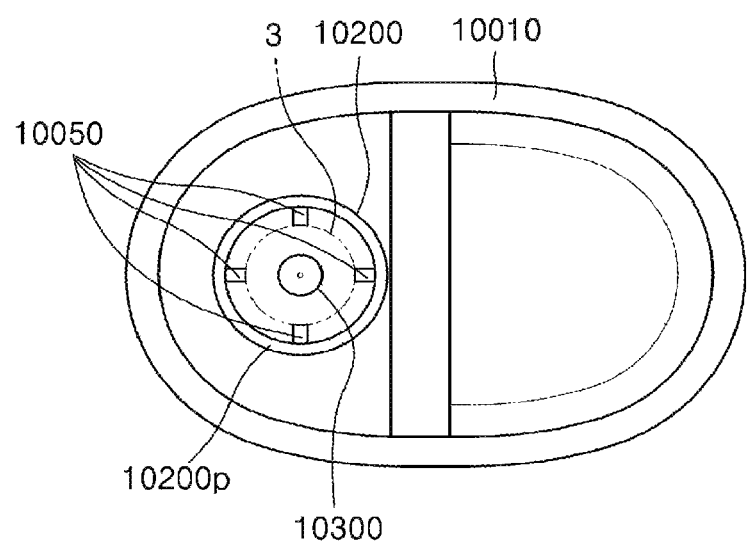
FIG. 44 is a top view of some of components of the aerosol generating apparatus according to the embodiment shown in FIG. 43.
Figure 45:
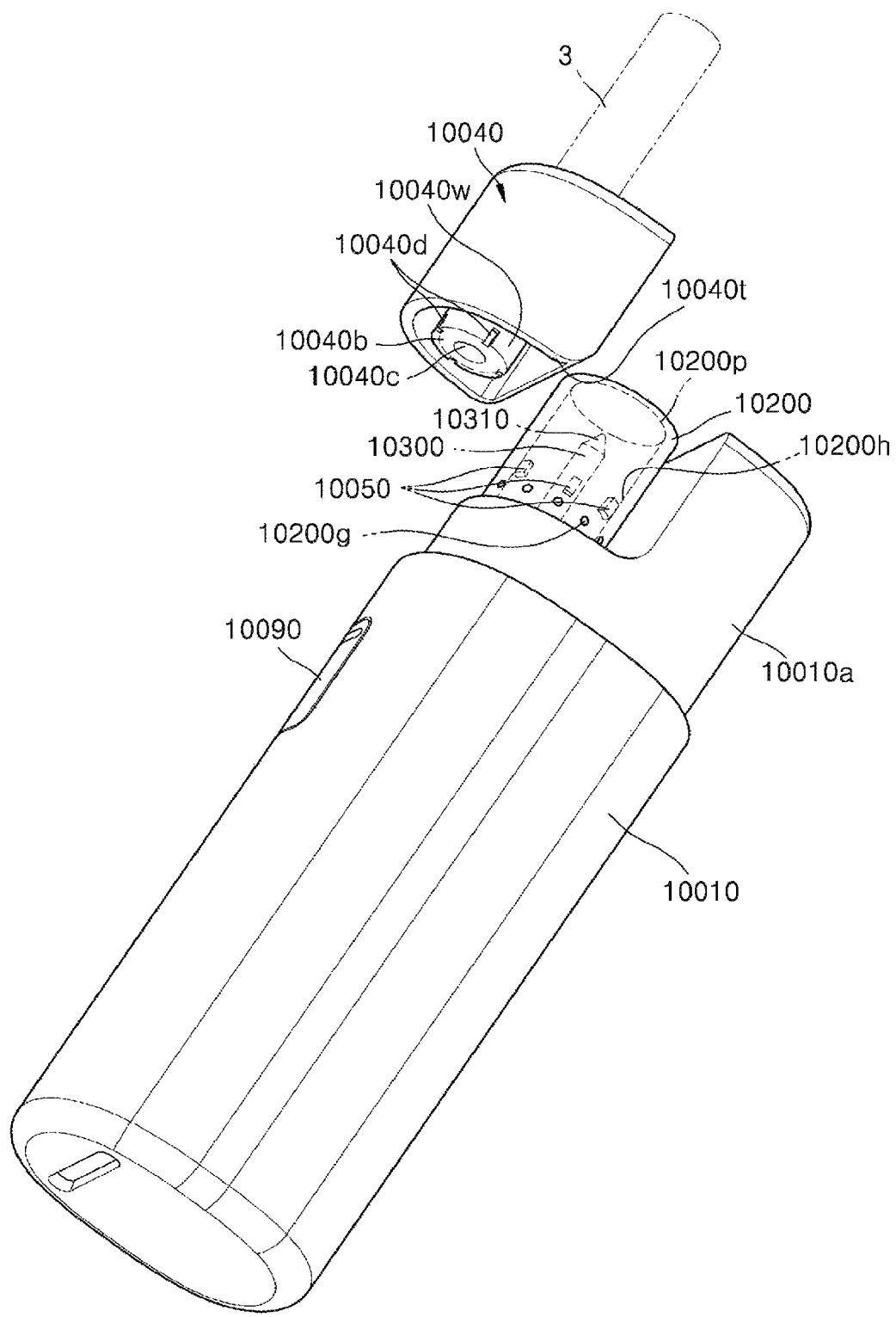
FIG. 45 is a perspective view of the aerosol generating apparatus according to the embodiment shown in FIG. 42 viewed at another angle.

FIG. 42 is a lateral view exemplifying another operating state of the aerosol generating apparatus according to the embodiment shown in FIG. 40A. FIG. 43 is a perspective view of the aerosol generating apparatus according to the embodiment shown in FIG. 42 viewed at another angle. FIG. 44 is a top view of some of components of the aerosol generating apparatus according to the embodiment shown in FIG. 43. FIG. 45 is a perspective view of the aerosol generating apparatus according to the embodiment shown in FIG. 42 viewed at another angle.

Referring to FIGS. 42 to 45, an aerosol generating apparatus includes the casing 10010, a hollow-shaped protruding tube 10200 protruding from the first end portion 10010a of the casing 10010 and having an opening 10200p opened toward the outside, a heater 10300 installed in the casing 10010 to be located inside the protruding tube 10200, the accommodating portion 10040 that may be coupled with the protruding tube 10200 and may be separated from the protruding tube 10200, and a protruding portion 10050 protruding from the inside of the protruding tube 10200 and penetrate through the accommodating portion 10040 to support the cigarette 3 inserted into the accommodating portion 10040.

As shown in FIG. 42, a user may separate the accommodating portion 10040 from the casing 10010 by holding and pulling the accommodating portion 10040 attached to the casing 10010.

The protruding tube 10200 surrounds and protects the heater 10300 and functions to support the accommodating portion 10040 when the accommodating portion 10040 is coupled. Since the protruding tube 10200 has a hollow structure with an empty space therein, the protruding tube 10200 includes a combining path 10200h in which at least a portion of the accommodating portion 10040 may be inserted. The top of the combining path 10200h is connected to an opening 10200p that is opened upward outside of the aerosol generating apparatus.

The casing 10010 is provided with the heater 10300 for heating the cigarette 3. The heater 10300 is Installed in the casing 10010 such that an end portion 10310 is located inside the protruding tube 10200. When the cigarette 3 is accommodated in the accommodating portion 10040 while the accommodating portion 10040 is being coupled with the protruding tube 10200, the end portion 10310 of the heater 10300 is inserted into the bottom surface of an end portion of the cigarette 3.

An electricity supply device 10700 disposed inside the casing 10010 is electrically connected to the bottom end portion of the heater 10300 through an electric wire 10710. When electricity of the electricity supply device 10700 is supplied to the heater 10300 while the cigarette 3 is being inserted into the end portion 10310 of the heater 10300, the heater 10300 is heated, and thus the cigarette 3 is heated.

Referring to FIGS. 43 and 45, the accommodating portion 10040 may be inserted into the combining path 10200h inside the protruding tube 10200 through the opening 10200p of the protruding tube 10200 and Includes a sidewall 10040w forming the accommodating path 10040h for accommodating the cigarette 3, an Insertion hole 10040p opened outward from one end of the accommodating path 10040h to enable insertion of the cigarette 3, a bottom wall 10040b closing the other end of the heater 10300h and having a heater hole 10040c through which the end portion 10310 of the heater 10300 passes.

The size of the heater hole 10040c formed in the bottom wall 10040b of the accommodating portion 10040 may correspond to the thickness of the end portion 10310 of the heater 10300. For example, when the end portion 10310 of the heater 10300 has a circular cross-section, the heater hole 10040c also has a circular cross-sectional shape, wherein the heater hole 10040c is formed to have an inner diameter corresponding to the outer diameter of the end portion 10310 of the heater 10300.

The embodiment is not limited by the inner diameter of the heater hole 10040c. For example, the inner diameter of the heater hole 10040c may be larger than the outer diameter of the end portion 10310 of the heater 10300, and thus the inner surface of the heater hole 10040c may be apart from the outer surface of the end portion 10310 of the heater 10300.

The accommodating portion 10040 includes an outer wall 10040t surrounding the sidewall 10040w and apart outwardly in the radius-wise direction of the sidewall 10040w. When the accommodating portion 10040 is coupled with the protruding tube 10200, the protruding tube 10200 is inserted between the outer wall 10040t and the sidewall 10040w, and thus the coupled state of the accommodating portion 10040 and the protruding tube 10200 may be stably maintained.

The sidewall 10040w of the accommodating portion 10040 is inserted into the combining path 10200h of the protruding tube 10200 when the accommodating portion 10040 is coupled with the protruding tube 10200. The end portion 10310 of the heater 10300 located inside the protruding tube 10200 passes through the heater hole 10040c of the accommodating portion 10040 while the sidewall 10040w of the accommodating portion 10040 is moving downward along the combining path 10200h of the protruding tube 10200.

The end portion 10310 of the heater 10300 passes through the heater hole 10040c of the accommodating portion 10040 and is located inside the accommodating path 10040h of the accommodating portion 10040 while the accommodating portion 10040 is being coupled with the protruding tube 10200. The end portion 10310 of the heater 10300 is inserted into the cigarette 3 when the cigarette 3 is accommodated in the accommodating path 10040h of the accommodating portion 10040 while the accommodating portion 10040 is being coupled with the protruding tube 10200.

When a user of the aerosol generating apparatus inserts the cigarette 3 into the accommodating path 10040h, the cigarette 3 moves along the accommodating path 10040*h* and, when an end portion of the cigarette 3 reaches the bottom wall 10040*b* of the accommodating portion 10040, an impression that the end portion of the cigarette 3 contacts the bottom wall 10040*b* is transmitted to a hand of the user holding the cigarette 3. Therefore, the user may easily mount the cigarette 3 to the aerosol generating apparatus through a simple action of holding the cigarette 3 in his/her hand and pushing the cigarette 3 into the insertion hole 10040*p* of the accommodating path 10040*h*.

When the user separates the cigarette 3 from the accommodating portion 10040, the user may pull the cigarette 3 out of the accommodating portion 10040 by holding and turning the cigarette 3 by hand. The cigarette 3 and the heater 10300 adhered to each other via a tobacco material may be completely separated while the user is holding and turning the cigarette 3 by hand.

After the cigarette 3 is separated from the accommodating portion 10040, the user may perform a cleaning operation of the interior of the accommodating portion 10040. When the user removes the accommodating portion 10040 from the casing 20010 to perform the cleaning operation, the user may pull the accommodating portion 10040 out of the casing 20010 by holding the accommodating portion 10040 by hand.

A plurality of protruding portions 10050 for supporting the cigarette 3 are arranged to protrude from the inner wall of the combining path 10200*h* of the protruding tube 10200. The protruding portion 10050 contacts the outer surface of the cigarette 3 inserted into the accommodating portion 10040 by penetrating the sidewall 10040*w* of the accommodating portion 10040 coupled with the protruding tube 10200.

The protruding tube 10200 may also function to directly supply the outside air to an end portion of the cigarette 3. To this end, the protruding tube 10200 includes an air hole 10200*g* for communication between the inside and the outside of the protruding tube 10200. The air hole 10200*g* may be apart in the circumferential direction from the center of the protruding tube 10200 in the lengthwise direction, and a plurality of air holes 10200*g* may be provided. The air hole 10200*g* forms a flow path for the air, such that the outside air is introduced into the protruding tube 10200.

Figure 46:
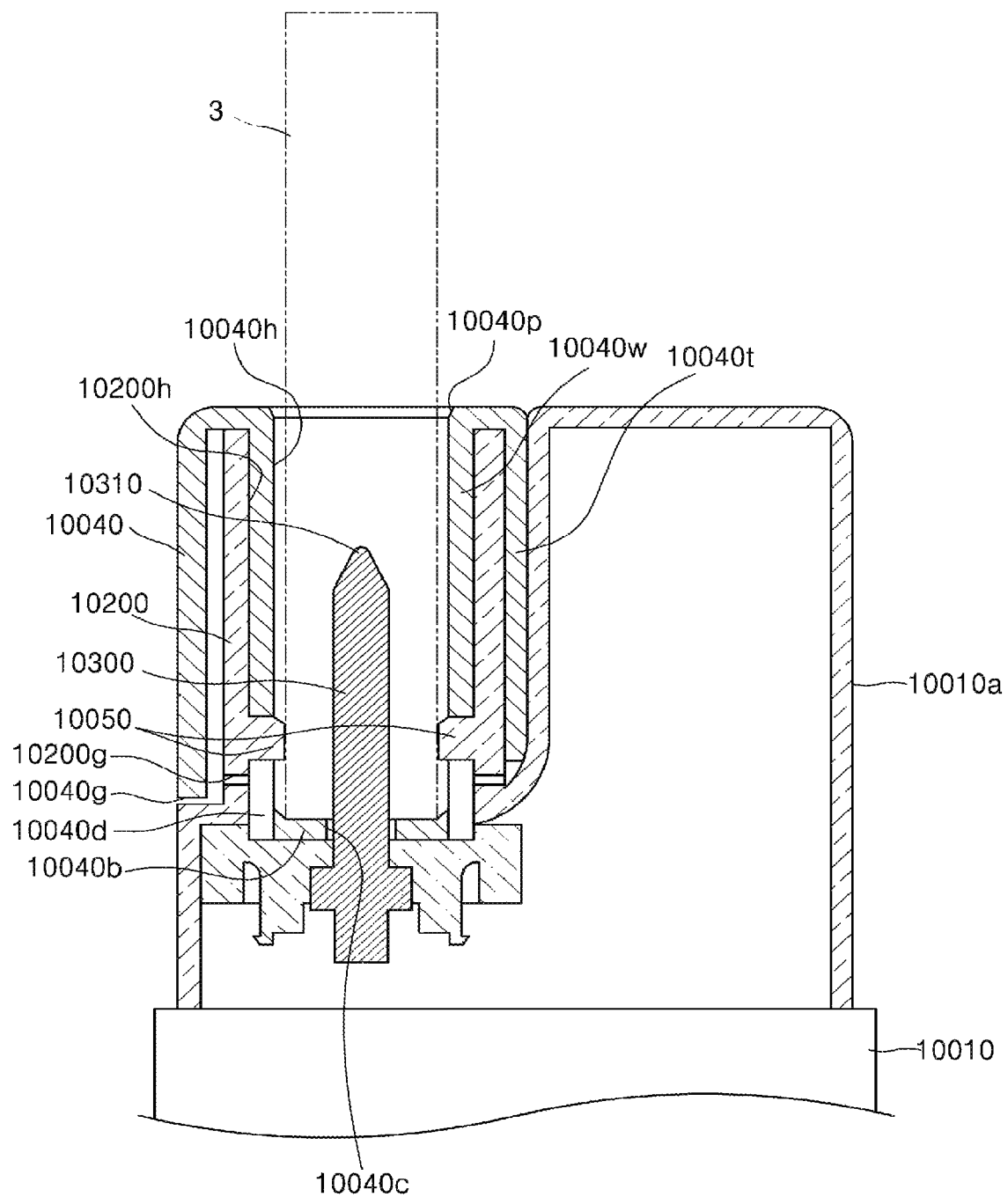
FIG. 46 is a lateral sectional view of portions of some of components of the aerosol generating apparatus according to the embodiment shown in FIG. 41.
Figure 47:
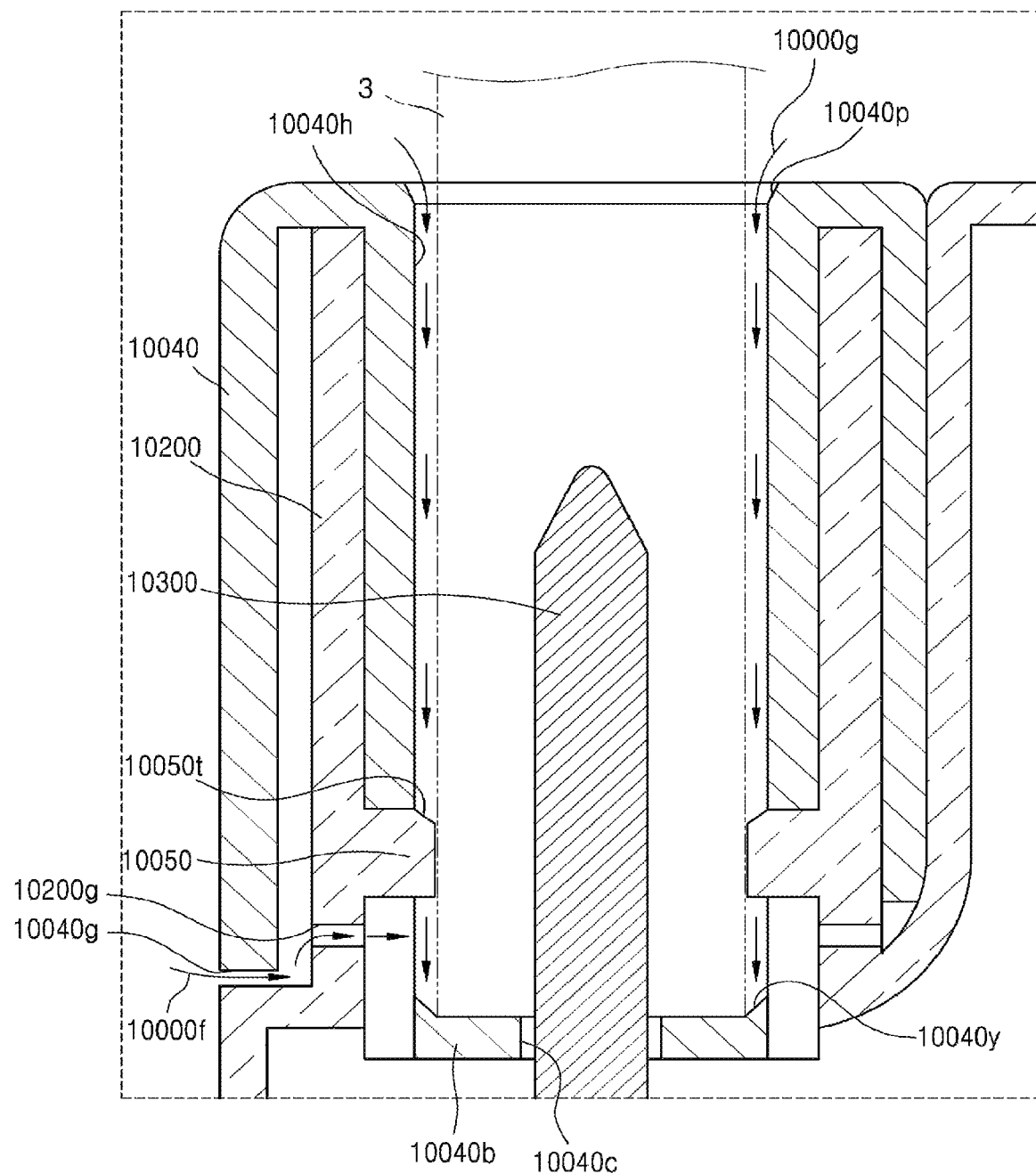
FIG. 47 is an enlarged view diagram showing an air flow by enlarging a portion of the aerosol generating apparatus according to the embodiment shown in FIG. 46.
Figure 48:
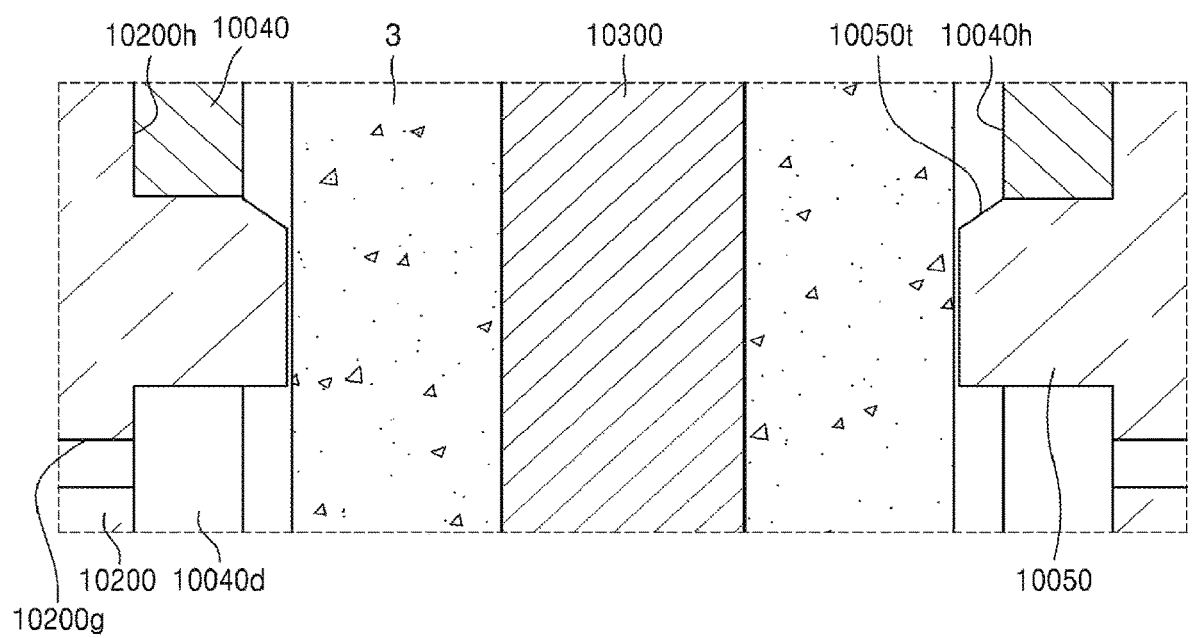
FIG. 48 is an enlarged view of a portion of the aerosol generating apparatus according to the embodiment shown in FIG. 47.

FIG. 46 is a lateral sectional view of portions of some of components of the aerosol generating apparatus according to the embodiment shown in FIG. 41. FIG. 47 is an enlarged view diagram showing an air flow by enlarging a portion of the aerosol generating apparatus according to the embodiment shown in FIG. 46. FIG. 48 is an enlarged view of a portion of the aerosol generating apparatus according to the embodiment shown in FIG. 47.

While the accommodating portion 10040 is being coupled with the protruding tube 10200, an air introduction gap 10040*g* for allowing the air outside the accommodating portion 10040 to flow into the accommodating portion 10040 is formed at a contacting portion between the accommodating portion 10040 and the protruding tube 10200, that is, between the outer wall 10040*t* of the accommodating portion 10040 and the protruding tube 10200. Therefore, as shown in FIGS. 39, 40A, and 40B, while the cover 10020 is being coupled with the casing 10010, the air outside the cover 10020 is introduced into the cover 10020 through an outside air introduction gap 10040*g* between the cover 10020 and the casing 10010 and is then introduced into the accommodating portion 10040 through the air Introduction gap 10040*g*.

Referring to FIG. 47, a first airflow 10000*f* sequentially passed through the outside air introduction gap 10020*g* and the air Introduction gap 10040*g* passes through the air hole 10200*g* of the protruding tube 10200 and reaches the outer surface of an end portion of the cigarette 3 accommodated in the accommodating portion 10040.

The cigarette 3 has a cylindrical shape and the accommodating path 10040*h* of the accommodating portion 10040 also has a cylindrical shape in correspondence to the shape of the cigarette 3. The diameter of the accommodating path 10040*h* of the accommodating portion 10040 is larger than the diameter of the cigarette 3. Therefore, when the cigarette 3 is accommodated in the accommodating portion 10040, the outer surface of the cigarette 3 and the accommodating path 10040*h* of the accommodating portion 10040 are apart from each other. In other words, in FIG. 47, the outside air is introduced into the space formed between the outer surface of the cigarette 3 and the accommodating path 10040*h* of the accommodating portion 10040 through the Insertion hole 10040*p* and forms a second airflow 10000*g*.

The accommodating portion 10040 also includes a through hole 10040*d* formed through the sidewall 10040*w*, such that the protruding portion 10050 passes therethrough. The protruding portion 10050 is formed to protrude from the surface of the accommodating path 10040*h* toward the cigarette 3 to contact the outer surface of the cigarette 3.

The protruding portions 10050 are arranged apart from one another on the outer surface of the cigarette 3 in the circumferential direction with respect to the center of the cigarette 3, such that a flow path through which the second airflow 10000*g* passes is formed between the protruding portions 10050. A plurality of through holes 10040*d* are formed in correspondence to the number of the protruding portions 10050. Although the protruding portions 10050 support the outer surface of the cigarette 3, the air may freely flow inside the accommodating path 10040*h* of the accommodating portion 10040, because the protruding portions 10050 adjacent to each other are apart from each other.

Although FIG. 47 shows that the number of the protruding portions 10050 is four and the number of the through holes 10040*d* is four, the embodiment is not limited by the number of the protruding portions 10050 and the number of the through holes 10040*d*. The number of protruding portions 10050 and the number of through holes 10040*d* may vary.

Also, positions and shapes of the protruding portion 10050 and the through hole 10040*d* may vary. For example, the protruding portion 10050 may extend around the center of the cigarette 3, that is, in the circumferential direction, to contact a portion of the outer surface of the cigarette 3 around the the cigarette 3, that is, in the circumferential direction, toward the center of the cigarette 3. Even when the protruding portions 10050 extends in the circumferential direction, the protruding portions 10050 adjacent to each other may be separated from each other to form a flow path through which the air passes in the accommodating path 10040*h*.

The end portion of the protruding portion 10050 contacting the outer surface of the cigarette 3 may be formed as a concave curved cylindrical surface in correspondence to the shape of the outer surface of the cigarette 3.

Referring to FIGS. 46 and 47, when the accommodating portion 10040 is coupled with the protruding tube 10200, the protruding portion 10050 is located above the bottom wall 10040*b* of the accommodating portion 10040 at a predetermined height to be apart from the bottom wall 10040*b* of the accommodating portion 10040. Therefore, the through hole 10040*d* of the accommodating portion 10040 may extend in the lengthwise direction of the accommodating path 10040h in correspondence to the position of the protruding portion 10050 to accommodate the protruding portion 10060 while the accommodating portion 10040 is being coupled with the protruding tube 10200.

An aligning inclined surface 10040y that aligns the position of the cigarette 3 accommodated in the accommodating portion 10040 to the center of the accommodating portion 10040 by guiding edges of the end portion of the cigarette 3 is installed on edges of the top surface of the accommodating portion 10040 facing toward the bottom wall 10040b of the accommodating path 10040h.

Referring to FIGS. 47 and 48, the protruding portion 10050 includes an inclined surface 10050d that is inclined with respect to the lengthwise direction of the accommodating path 10040h to guide movement of the cigarette 3 when the cigarette 3 is inserted into the accommodating path 10040h.

When the cigarette 3 is inserted into the accommodating path 10040h, moves along the accommodating path 10040h, and the end portion of the cigarette 3 reaches the position of the protruding portion 10050 protruding from the accommodating path 10040h, the inclined surface 10050d of the protruding portion 10050 guides movement of the cigarette 3, such that the end portion of the cigarette 3 may be inserted into the protruding portion 10050.

While the accommodating portion 10040 is being coupled with the protruding tube 10200 and the cigarette 3 is being inserted into the accommodating path 10040h of the accommodating portion 10040, the accommodating path 10040h is connected to the outside via the insertion hole 10040p, and thus an external second airflow 10000g flows into the accommodating path 10040h of the accommodating portion 10040 through the insertion hole 10040p. Also, a first airflow 10000f passed through the air introduction gap 10040g passes through the air hole 10200g of the protruding tube 10200 and reaches the outer surface of the end portion of the cigarette 3 accommodated in the accommodating portion 10040.

The cigarette 3 is supported by the protruding portions 10050 and the outer surface of the end portion of the cigarette (3) is not in contact with any component, the outer surface of the end portion of the cigarette 3 is surrounded by the air. When aerosol particles are generated from the cigarette 3 as the heater 10300 heats the cigarette 3 and a user inhales the air through his/her mouth by holding the cigarette 3 between his/her lips, the air around the outer surface of the end portion of the cigarette 3 pass through cigarette 3, and thus an air flow including the aerosol particles may be delivered to the user.

In the aerosol generating apparatus according to the embodiment shown in FIGS. 39 to 48, a user may easily mount the cigarette 3 in the aerosol generating apparatus through simple actions including opening an outside hole 10020p of the cover 10020, inserting the cigarette 3 into the insertion hole 10040p of the accommodating portion 10040, and pushing the cigarette 3 along the accommodating path 10040h.

Also, after using the cigarette 3, the user may pull the cigarette 3 out of the casing 10010 by holding and turning the cigarette 3 by hand.

Also, the user may separate the cover 10020 from the casing 10010 and separate the accommodating portion 10040 from the casing 10010 for a cleaning operation.

Since the protruding tube 10200 and the heater 10300 are exposed to the outside after the accommodating portion 10040 is completely separated from the casing 10010, the user may directly check states of the protruding tube 10200 and the heater 10300 and easily perform a cleaning operation.

Also, the protruding portions 10050 protruding inside of the accommodating path 10040h contact the outer surface of the cigarette 3 while the cigarette 3 is being inserted into the accommodating path 10040h of the accommodating portion 10040 attached to the casing 10010 of the aerosol generating apparatus, and thus the protruding portions 10050 stably support the cigarette 3. Therefore, while the aerosol generating apparatus is being used, the cigarette 3 is not separated from the aerosol generating apparatus and the state in which the cigarette 3 is accommodated in the accommodating path 10040h of the aerosol generating apparatus is stably maintained, and thus a user may enjoy the aerosol generating apparatus.

Also, as the protruding portions 10050 of the accommodating path 10040h of the accommodating portion 10040 contact portions of the outer surface of the cigarette 3, an air flow path in which the air may pass is formed between the accommodating path 10040h and the cigarette 3, and thus the outside air for assisting generation of aerosol may be supplied smoothly and sufficiently into the interior of the aerosol generating apparatus.

Figure 49:
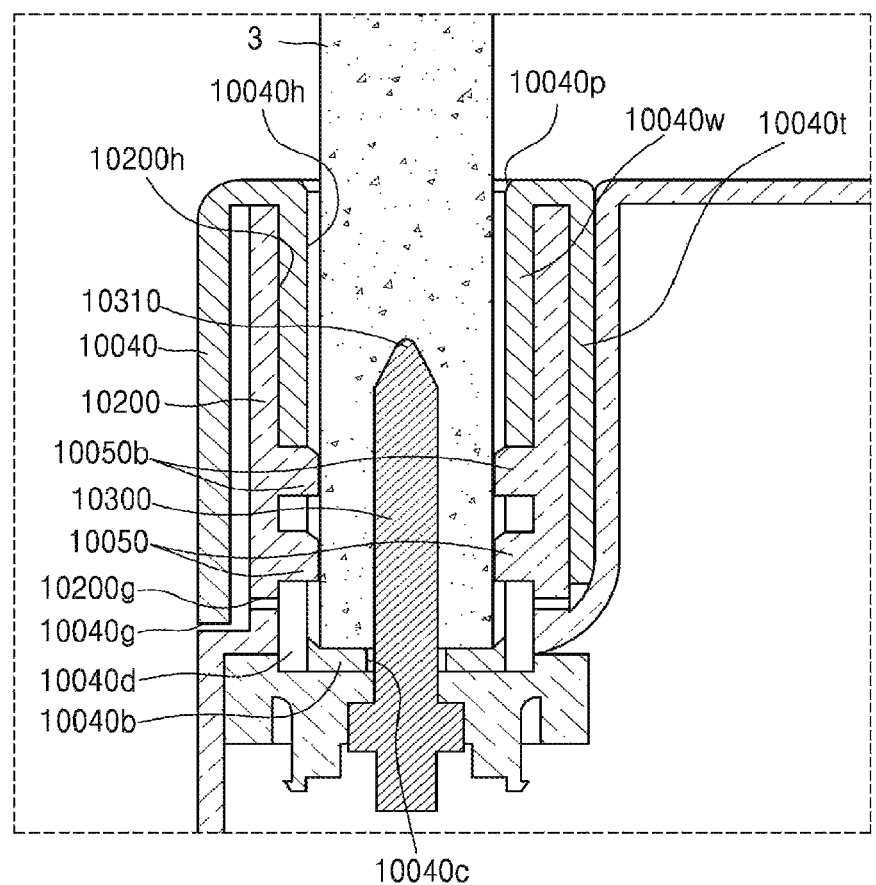
FIG. 49 is an enlarged lateral sectional view of a portion of an aerosol generating apparatus according to another embodiment.

FIG. 49 is an enlarged lateral sectional view of a portion of an aerosol generating apparatus according to another embodiment.

In the aerosol generating apparatus according to the embodiment shown in FIG. 49, a plurality of protruding portions 10050 and 10050b are arranged on the outer surface of the cigarette 3 to be apart from each other in the lengthwise direction of the cigarette 3.

In FIG. 49, the lower portion of the cigarette 3 in the lengthwise direction is supported by a lower protruding portion 10050. Also, the upper portion of the cigarette 3 in the lengthwise direction is supported by an upper protruding portion 10050b.

A plurality of lower protruding portions 10050 are arranged and are apart from one another on the outer surface of the cigarette 3 in the circumferential direction with respect to the center of the cigarette 3.

A plurality of upper protruding portions 10050b are also arranged and are apart from one another on the outer surface of the cigarette 3 in the circumferential direction with respect to the center of the cigarette 3.

The through hole 10040d formed in the sidewall 10040w of the accommodating portion 10040 is formed to extend in the lengthwise direction of the accommodating path 10040h to accommodate both the upper protruding portions 10050b and the lower protruding portions 10050.

The plurality of protruding portions 10050 and 10050b are apart from each other on the outer surface of the cigarette 3 in the circumferential direction with respect to the center of the cigarette 3 and are apart from each other on the outer surface of the cigarette 3 in the lengthwise direction of the cigarette 3, a flow path through which the air flows is formed between the protruding portions 10050 and 10050b adjacent to each other.

Figure 50:
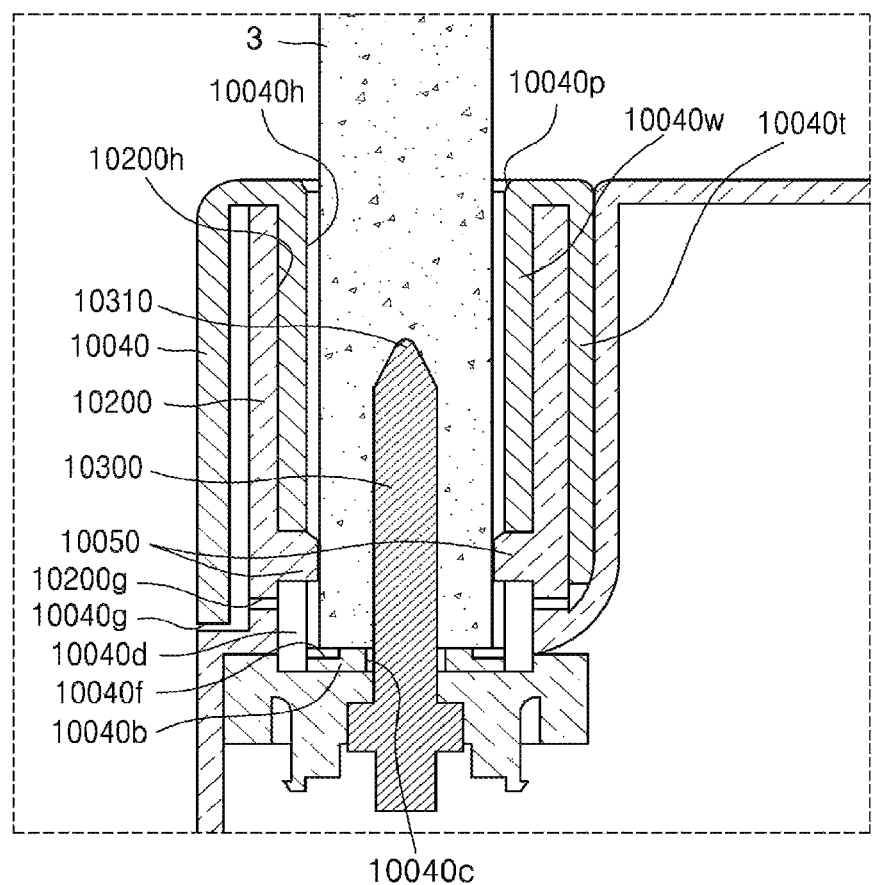
FIG. 50 is an enlarged lateral sectional view of a portion of an aerosol generating apparatus according to another embodiment.

FIG. 50 is an enlarged lateral sectional view of a portion of an aerosol generating apparatus according to another embodiment.

In the aerosol generating apparatus according to the embodiment shown in FIG. 50, a concave shaped connection passage 10040f is formed at outer edges of the top surface of the bottom wall 10040b of the accommodating portion 1004 contacting the end portion of the cigarette 3 when the cigarette 3 is inserted into accommodating portion 1004, the top surface facing the accommodating path 10040*h* of the accommodating portion 10040. As the connection passage 10040*f* is connected to the space between the outer surface of the cigarette 3 and the accommodating path 10040*h*, the air of the accommodating path 10040*h* is supplied to the bottom surface of the end portion of the cigarette 3 through the connection passage 10040*f* of the bottom wall 10040*b*, and thus the sufficient air for assisting generation of aerosol may be smoothly supplied to the cigarette 3.

Figure 51:
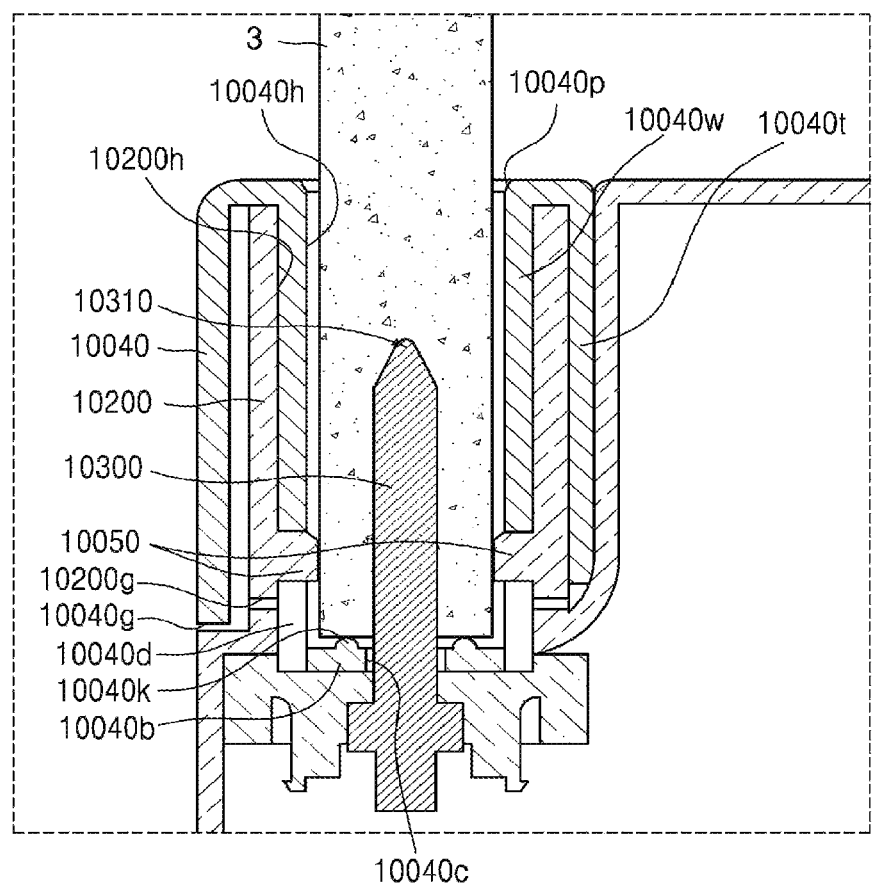
FIG. 51 is an enlarged lateral sectional view of a portion of an aerosol generating apparatus according to another embodiment.

FIG. 51 is an enlarged lateral sectional view of a portion of an aerosol generating apparatus according to another embodiment.

In the aerosol generating apparatus according to the embodiment shown in FIG. 51, a bottom protrusion 10040*k* protruding from the top surface of the bottom wall 10040*b* of the accommodating portion 1004 contacting the end portion of the cigarette 3 when the cigarette 3 is inserted into accommodating portion 1004, the top surface facing the accommodating path 10040*h* of the accommodating portion 10040. The bottom protrusion 10040*k* protrudes toward the inner space of the accommodating path 10040*h* at the bottom wall 10040*b* to support the bottom surface of the end portion of the cigarette 3. The bottom protrusion 10040*k* has an approximately hemispherical shape.

A plurality of bottom protrusions 10040*k* are arranged on the bottom wall 10040*b* to be apart from one other in the circumferential direction with respect to the center of a heater hole 10040*c* formed in the bottom wall 10040*b*. Therefore, since the air may pass through the space between the bottom protrusions 10040*k* adjacent to each other, the air Introduced from the outside into the accommodating path 10040*h* through the insertion hole 10040*p* of the accommodating path 10040*h* is supplied to the bottom surface of the end portion of the cigarette 3 through the space between the bottom protrusions 10040*k*.

In the aerosol generating apparatus according to the embodiment shown in FIG. 51, since the protruding portions 10050 protruding from the accommodating path 10040*h* of the accommodating portion 10040 also contact portions of the outer surface of the cigarette 3, a flow path through which the air may flow is formed between the accommodating path 10040*h* and the cigarette 3, and the air in the flow path is supplied to the bottom surface of the end portion of the cigarette 3, and thus the sufficient air for assisting generation of aerosol may be supplied smoothly to the cigarette 3.

Figure 52:
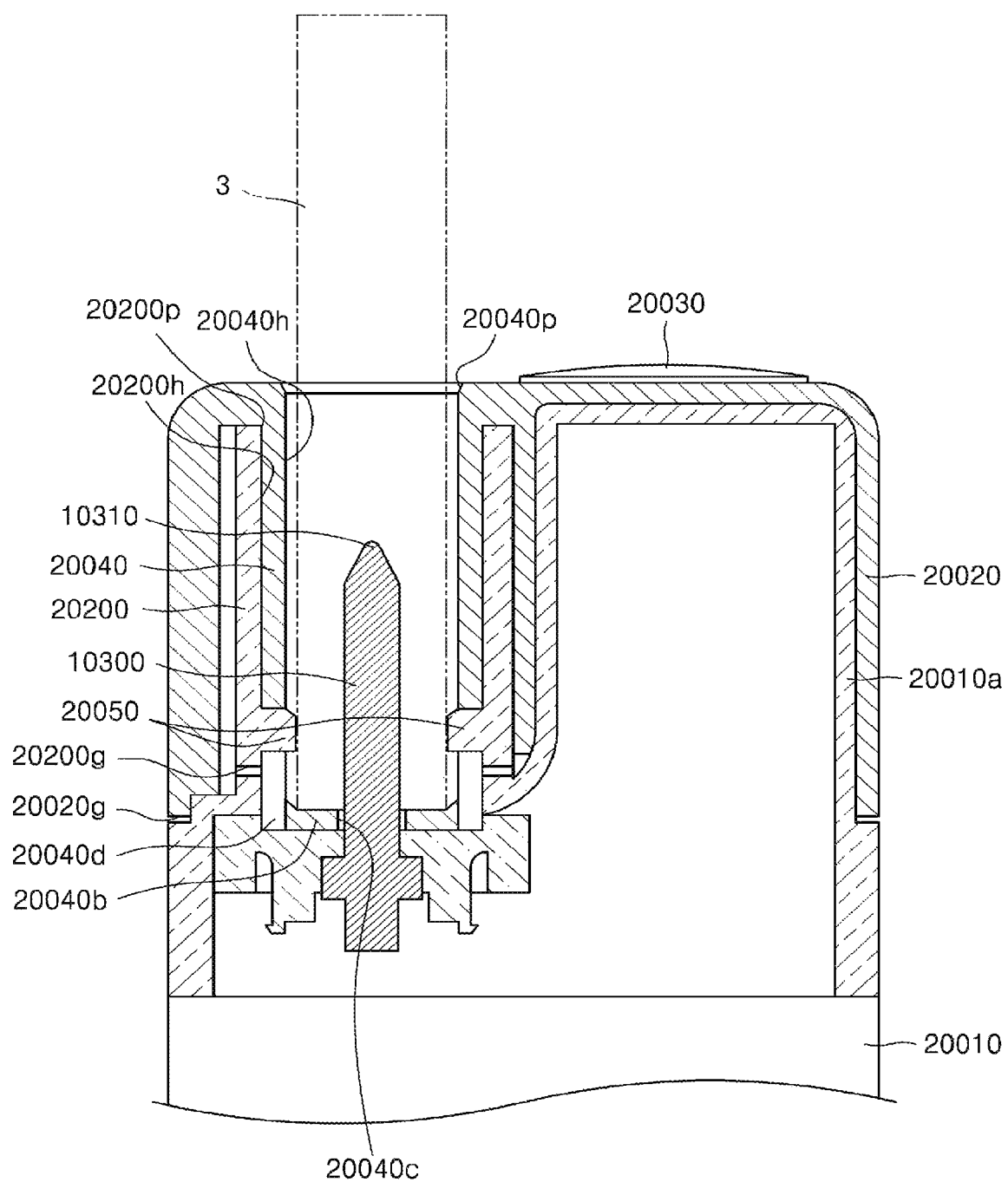
FIG. 52 is an enlarged lateral sectional view of a portion of an aerosol generating apparatus according to another embodiment.

FIG. 52 is an enlarged lateral sectional view of a portion of an aerosol generating apparatus according to another embodiment.

Referring to FIGS. 42 to 45, an aerosol generating apparatus includes the casing 20010, a hollow-shaped protruding tube 20200 protruding from a first end portion 20010*a* of the casing 20010 and having an opening 20200*p* opened toward the outside, the heater 10300 installed in the casing 20010 such that the end portion 10310 is to be located inside the protruding tube 20200, an accommodating portion 20040 that may be coupled with the protruding tube 20200 and may be separated from the protruding tube 20200, a protruding portion 20050 protruding from the inside of the protruding tube 20200 and penetrate through the accommodating portion 20040 to support the cigarette 3 inserted into the accommodating portion 20040, and a cover 20020 including a door 20030 that is integrally connected to the accommodating portion 20040 to expose an insertion hole 20040*p* to the outside.

On the top surface of the cover 20020, a door 20030 that may be moved to expose the insertion hole 20040*p* of the accommodating portion 20040 to the outside is installed. The door 20030 may be slidably coupled with the cover 20020 by using a rail assembly or may be rotatably coupled with the cover 20020 by using a hinge assembly.

When the insertion hole 20040*p* is exposed to the outside by the door 20030, a user may insert the end portion of the cigarette 3 into the insertion hole 10040*p* and mount the cigarette 3 in the accommodating path 20040*h* of the accommodating portion 20040.

An outside air introduction gap 20020*g* that allows the air to flow into the interior of the cover 20020 is formed at a portion where the cover 20020 contact the casing 20010 when the cover 20020 is coupled with the casing 20010.

After the cigarette 3 is removed from the aerosol generating apparatus after smoking and a cleaning operation is to be performed, the cover 20020 and the accommodating portion 20040 may be separated from the casing 20010 together. In other words, when a user holds the cover 20020 by hand and separates the cover 20020 and the accommodating portion 20040 from the casing 20010, the cover 20020 and the accommodating portion 20040 are separated from the casing 20010 together.

The protruding tube 20200 surrounds and protects the heater 10300 and functions to support the accommodating portion 20040 and the cover 20020 when the accommodating portion 20040 is coupled with the protruding tube 20200. Since the protruding tube 20200 has a hollow structure with an empty space therein, the protruding tube 20200 includes a combining path 20200*h* in which at least a portion of the accommodating portion 20040 may be inserted. The top of the combining path 20200*h* is connected to an opening 20200*p* that is opened upward outside of the aerosol generating apparatus.

The protruding tube 20200 may also function to directly supply the outside air to an end portion of the cigarette 3. To this end, the protruding tube 20200 includes an air hole 20200*g* for communication between the inside and the outside of the protruding tube 20200. The air hole 20200*g* may be apart in the circumferential direction from the center of the protruding tube 20200 in the lengthwise direction, and a plurality of air holes 10200*g* may be provided. The air hole 20200*g* forms a flow path for the air, such that the outside air is introduced into the protruding tube 20200.

The accommodating portion 20040 may be inserted into a combining path 20200*h* of the protruding tube 20200 through the opening 20200*p* of the protruding tube 20200 and includes the accommodating path 20040*h* capable of accommodating the cigarette 3, an insertion hole 20040*p* which is opened outward from one end of the accommodating path 20040*h* for Insertion of the cigarette 3 thereinto, and a bottom wall 20040*b* which closes the other end of the accommodating path 20040*h* and includes a heater hole 20040*c* through which the end portion 10310 of the hater 10300 passes.

The accommodating portion 20040 is formed integrally with the cover 20020. For example, the cover 20020 and the accommodating portion 20040 may be integrally formed through injection molding or a 3-dimensional printing method by using a material like plastic. Alternatively, the cover 20020 and the accommodating portion 20040 may be separately fabricated and attached to each other via screws or fixed to each other via a coupling members like bolts or an adhesive.

The end portion 20310 of the heater 20300 passes through the heater hole 20040*c* of the accommodating portion 20040 and is located inside the accommodating path 20040*h* of the accommodating portion 20040 while the accommodating portion 20040 is being coupled with the protruding tube 20200. The end portion 20310 of the heater 20300 is inserted into the cigarette 3 when the cigarette 3 is accommodated in the accommodating path 20040*h* of the accommodating portion 20040 while the accommodating portion 20040 is being coupled with the protruding tube 20200.

A plurality of protruding portions 20050 for supporting the cigarette 3 are arranged to protrude from the inner wall of the combining path 20200*h* of the protruding tube 20200. The protruding portion 20050 contacts the outer surface of the cigarette 3 inserted into the accommodating portion 20040 by penetrating the accommodating portion 20040 coupled with the protruding tube 20200.

The air outside the cover 20020 passes through the outside air introduction gap 20020*g* between the cover 20020 and the casing 20010 and is introduced into the cover 20020 while the cover 20020 is being coupled with the casing 20010. A first airflow generated through the outside air introduction gap 20020*g* passes through the air hole 20200*g* of the protruding tube 20200 and reaches the outer surface of the end portion of the cigarette 3 accommodated in the accommodating portion 20040.

Also, while the accommodating portion 20040 is being coupled with the protruding tube 20200 and the cigarette 3 is being inserted into the accommodating path 20040*h* of the accommodating portion 20040, the accommodating path 20040*h* is connected to the outside via the insertion hole 20040*p*, and thus the outside air is introduced into the accommodating path 20040*h* of the accommodating portion 20040 through the insertion hole 20040*p* and forms a second airflow.

In the aerosol generating apparatus according to the embodiment shown in FIG. 52, a user may easily mount the cigarette 3 in the aerosol generating apparatus with simple actions of opening the cover 20020, inserting the cigarette 3 into the insertion hole 20040*p* of the accommodating portion 20040, and pushing the cigarette 3 along the accommodating path 20040*h*.

Also, when the user removes the cigarette 3 from the casing 20010 after finishing the use of the cigarette 3, the user may separate the cigarette 3 from the aerosol generating apparatus with simple actions of holding and turning the upper end portion of the cigarette 3 by hand and pulling the cigarette 3 outwardly from the accommodating path 20040*h*.

Also, when performing a cleaning operation, the user may separate the accommodating portion 20040 and the cover 20020 from the casing 20010 by separating the cover 20020 and the accommodating portion 20040 from the casing 20010 together.

Figure 53:
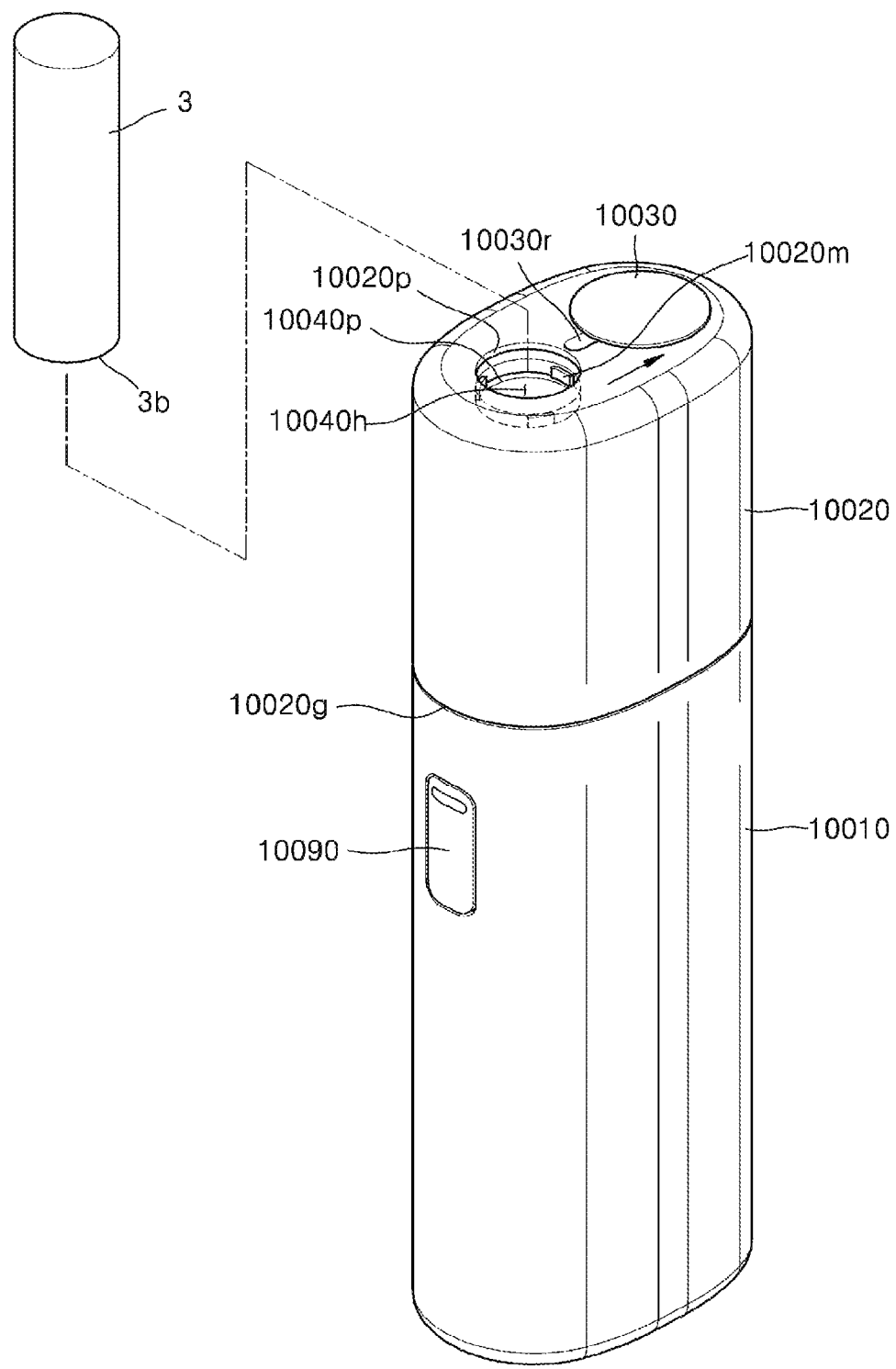
FIG. 53 is a perspective view exemplifying an operating state of an aerosol generating apparatus according to another embodiment.
Figure 54:
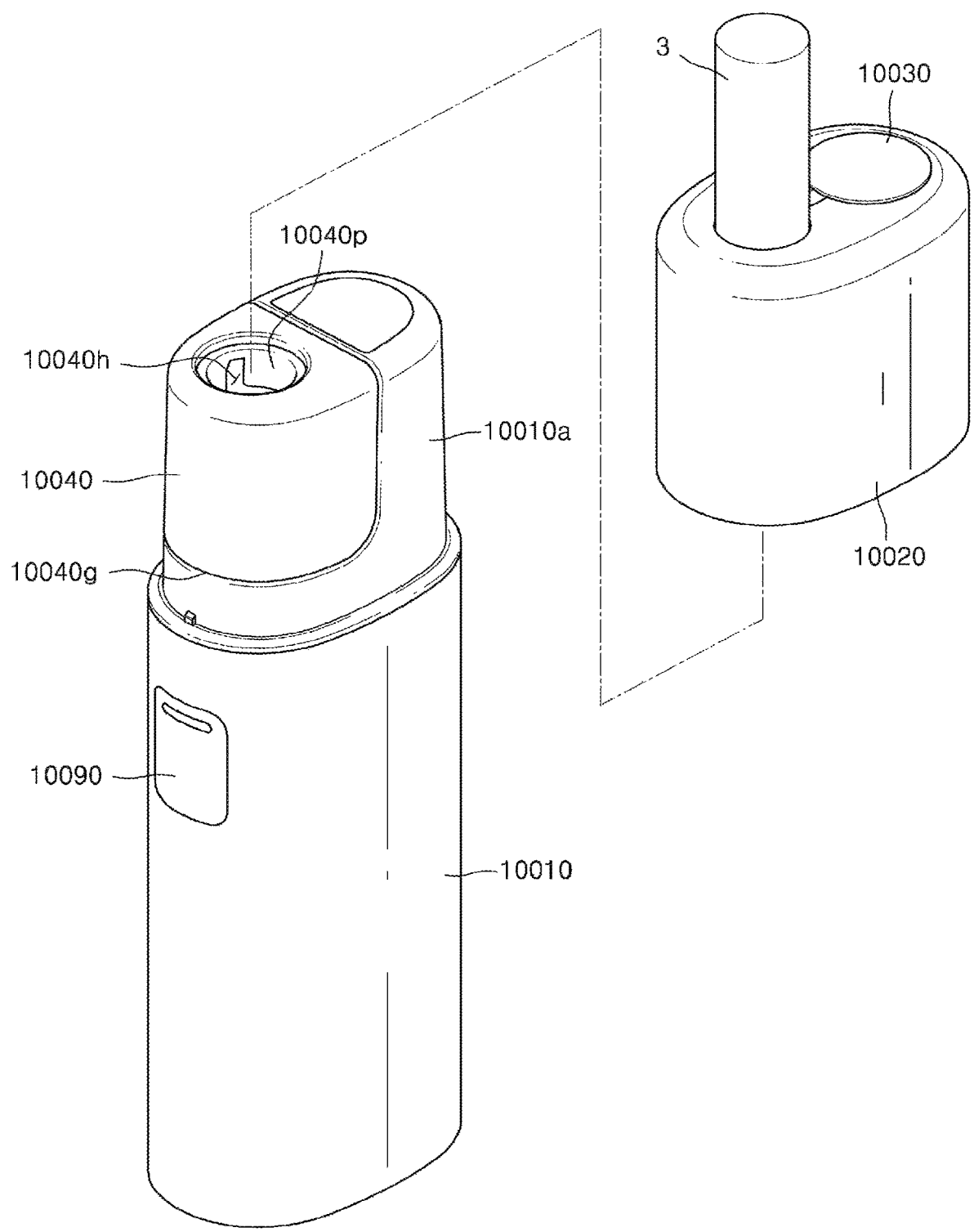
FIG. 54 is a perspective view diagram showing an operating state of the aerosol generating apparatus according to the embodiment shown in FIG. 53, from which some of components are removed.

FIG. 53 is a perspective view exemplifying an operating state of an aerosol generating apparatus according to another embodiment. FIG. 54 is a perspective view diagram showing an operating state of the aerosol generating apparatus according to the embodiment shown in FIG. 53, from which some of components are removed.

The aerosol generating apparatus according to the embodiment shown in FIGS. 53 and 54 includes the casing 10010 and the cover 10020.

The cover 10020 coupled with a first end of the casing 10010 constitutes the outer appearance of the aerosol generating apparatus 10000 together with the casing 10010. The casing 10010 constitutes the outer appearance of the aerosol generating apparatus 10000 and accommodates various components in a space formed therein.

A locking device may be installed between the cover 10020 and the casing 10010 to maintain the attachment between the cover 10020 and the casing 10010. The locking device may include, for example, a magnet and a metal member that sticks to the magnet. When a magnet is used for the locking device, a magnet may be installed on either one of the cover 10020 and the casing 10010 and a metal that sticks to the magnet may be attached to the other one. Alternatively, magnets may be installed on both the cover 10020 and the casing 10010.

An outside hole 10020*p* through which the cigarette 3 may be Inserted is formed on the top surface of the cover 10020. When the door 10030 slides in a straight line along the rail 10030*r* on the top surface of the cover 10020, the outside hole 10020*p* and the insertion hole 10040*p* through which the cigarette 3 may be inserted are exposed to the outside. The outside hole 10020*p* of the cover 10020 exposes the Insertion hole 10040*p* of an accommodating path 10040*h* capable of accommodating the cigarette 3 to the outside.

When the outside hole 10020*p* is exposed to the outside by the door 10030, a user may insert an end portion 3*b* of the cigarette 3 into the outside hole 10020*p* and the insertion hole 10040*p*, thereby placing the cigarette 3 in the accommodating path 10040*h* formed inside the housing 10020.

A plurality of cigarette supporting protrusions 10020*m*, which are arranged apart from one another in the circumferential direction on the inner surface of the outside hole 10020*p* and protrude toward the center of the outside hole 10020*p*, are arranged in the outside hole 10020*p* of the cover 10020. The cigarette support protrusions 10020*m* pass through the outside hole 10020*p* and contact the outer surface of the cigarette 3 inserted in the Insertion hole 10040*p* and the accommodating path 10040*h* to support the cigarette 3.

At the casing 10010, a button 10090 is provided. As the button 10090 is manipulated, the operation of the aerosol generating apparatus 10000 may be controlled.

An outside air Introduction gap 10020*g* that allows the air to flow into the interior of the cover 10020 is formed at a portion where the cover 10020 contact the casing 10010 when the cover 10020 is coupled with the casing 10010.

When the user removes the cigarette 3 from the aerosol generating apparatus after using the cigarette 3, the user may hold and turn the cigarette 3 by hand and pull the cigarette 3 out of the casing 10010. Alternatively, when the user turns the cigarette 3 and then pulls the cover 10020, the cover 10020 may be separated from the casing 10010 together with the cigarette 3. As the cigarette 3 is separated from the casing 10010 by turning the cigarette 3, the attachment between the cigarette 3 and a heater is released and a tobacco material attached to the cigarette 3 may be discharged out of the casing 10010 together with the cigarette 3.

When the cover 1002 is pulled without turning the cigarette 3, the cigarette 3 is separated from the casing 10010, but a tobacco portion of the cigarette 3 (i.e., the first portion 310 of FIGS. 23A and 23B) may remain at the heater without being discharged from the casing 10010. In this case, the user may remove the cover 1002 from the casing 1001, and then remove the accommodating portion 1004 from the casing 1001. At this time, the tobacco portion remaining at the heater is separated from the casing 1001 together with the accommodating portion 1004. Thereafter, the user may remove a tobacco portion remaining within the separate accommodating portion 1004.

Figure 55:
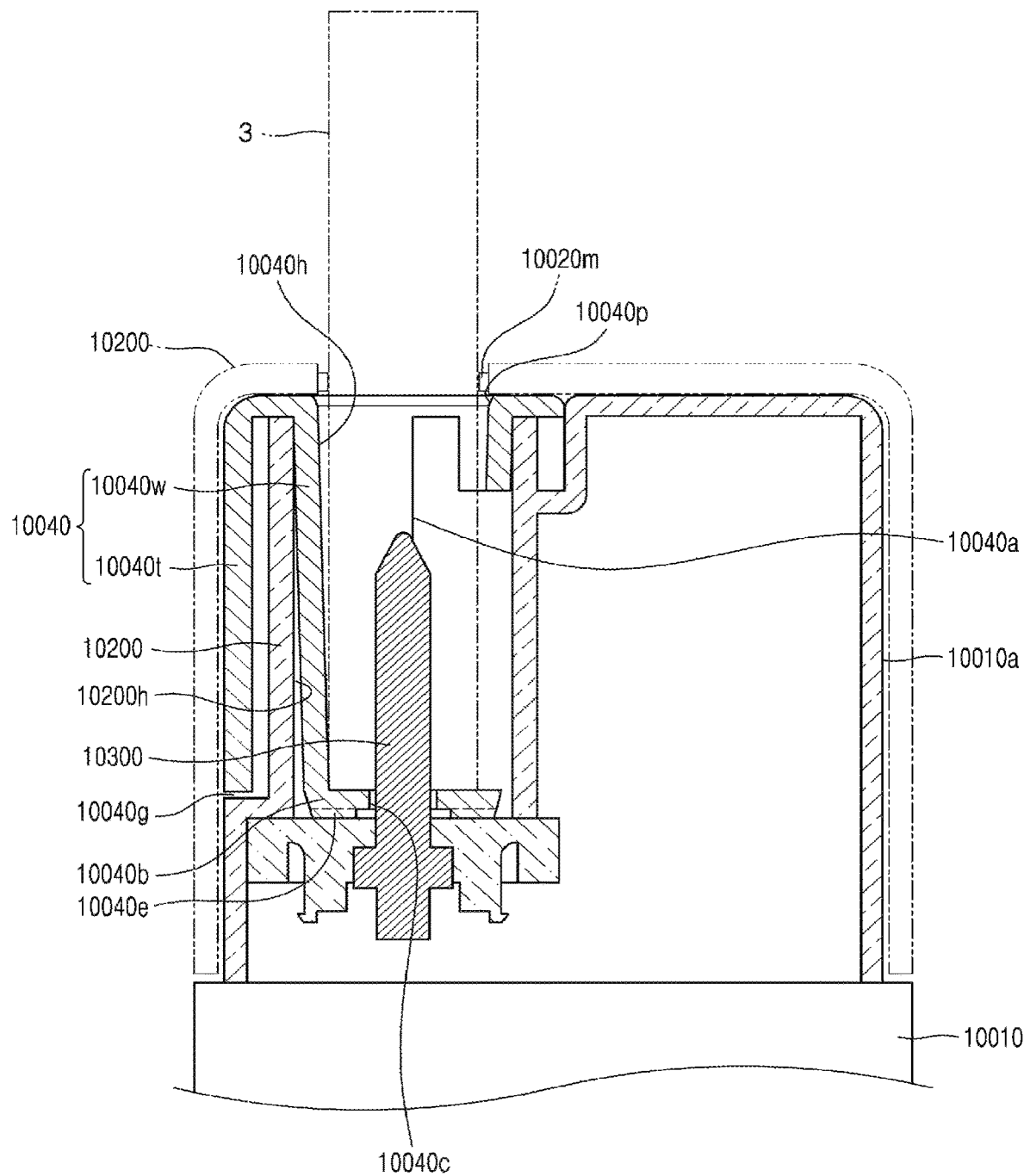
FIG. 55 is a lateral sectional view of some of components in the aerosol generating apparatus shown in FIG. 54.

FIG. 55 is a lateral sectional view of some of components in the aerosol generating apparatus shown in FIG. 54.

The aerosol generating apparatus includes the casing 10010, the hollow-shaped protruding tube 10200 protruding from the first end 10010*a* of the casing 10010 and having an opening opened to the outside, the heater 10300 installed to the casing 10010 to be located inside the protruding tube 10200, and the accommodating portion 10040 that may be coupled with the protruding tube 10200 and may be separated from the protruding tube 10200.

Figure 56:
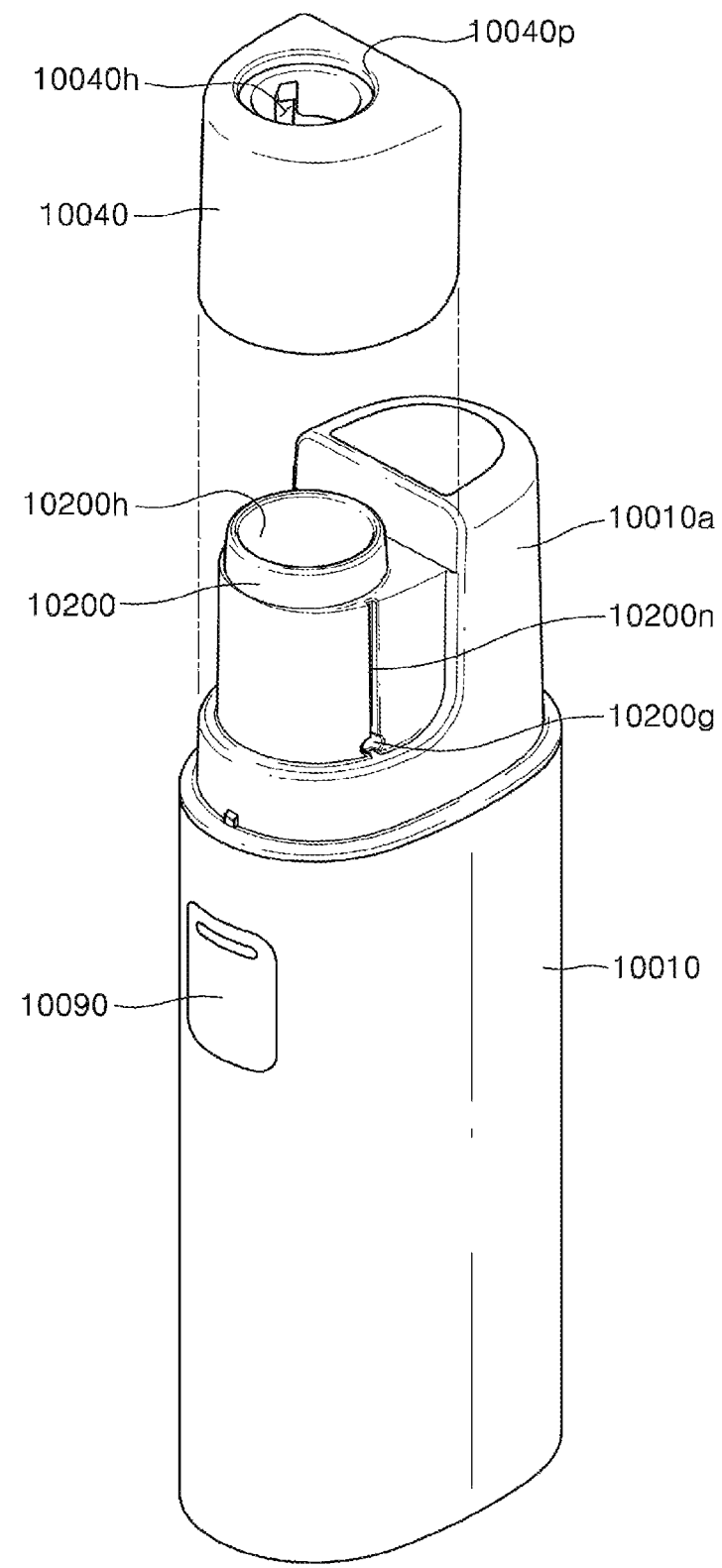
FIG. 56 is a perspective view diagram showing an operating state of the aerosol generating apparatus according to the embodiment shown in FIG. 53, from which some of the components are detached.

FIG. 56 is a perspective view diagram showing an operating state of the aerosol generating apparatus according to the embodiment shown in FIG. 53, from which some of the components are detached.

After the cigarette 3 is separated from the aerosol generating apparatus, the user may carry out a cleaning operation to remove any tobacco material that may be remaining inside the aerosol generating apparatus. As shown in FIG. 56, the cleaning operation of the aerosol generating apparatus may be performed by separating the accommodating portion 10040 from the casing 10010 after the user removes the cover 10020 from the casing 10010 of the aerosol generating apparatus 10000 to expose the inner space and a heater of the aerosol generating apparatus to the outside and remove a tobacco material therefrom.

The protruding tube 10200 surrounds and protects the heater 10300 and functions to support the accommodating portion 10040 when the accommodating portion 10040 is coupled. Since the protruding tube 10200 has a hollow structure with an empty space therein, the protruding tube 10200 includes a combining path 10200h in which at least a portion of the accommodating portion 10040 may be inserted. The top of the combining path 10200h forms an opening that is opened upward outside of the aerosol generating apparatus.

The protruding tube 10200 includes a guiding groove 10020n extending in a straight line in the lengthwise direction of the protruding tube 10200 to be coupled with the accommodating portion 10040.

The protruding tube 10200 may also function to directly supply the outside air to an end portion of the cigarette 3. To this end, the protruding tube 10200 includes an air hole 10200g for communication between the inside and the outside of the protruding tube 10200. The air hole 10200g is arranged to be connected to an end portion of the guiding groove 10020n. The air hole 10200g may be apart in the circumferential direction from the center of the protruding tube 10200 in the lengthwise direction, and a plurality of air holes 10200g may be provided. The air hole 10200g forms a flow path for the air, such that the outside air is introduced into the protruding tube 10200.

The casing 10010 is provided with the heater 10300 for heating the cigarette 3. The heater 10300 is installed in the casing 10010 such that an end portion is located inside the protruding tube 10200. When the cigarette 3 is accommodated in the accommodating portion 10040 while the accommodating portion 10040 is being coupled with the protruding tube 10200, the end portion of the heater 10300 is inserted into the bottom surface of an end portion of the cigarette 3.

Figure 57:
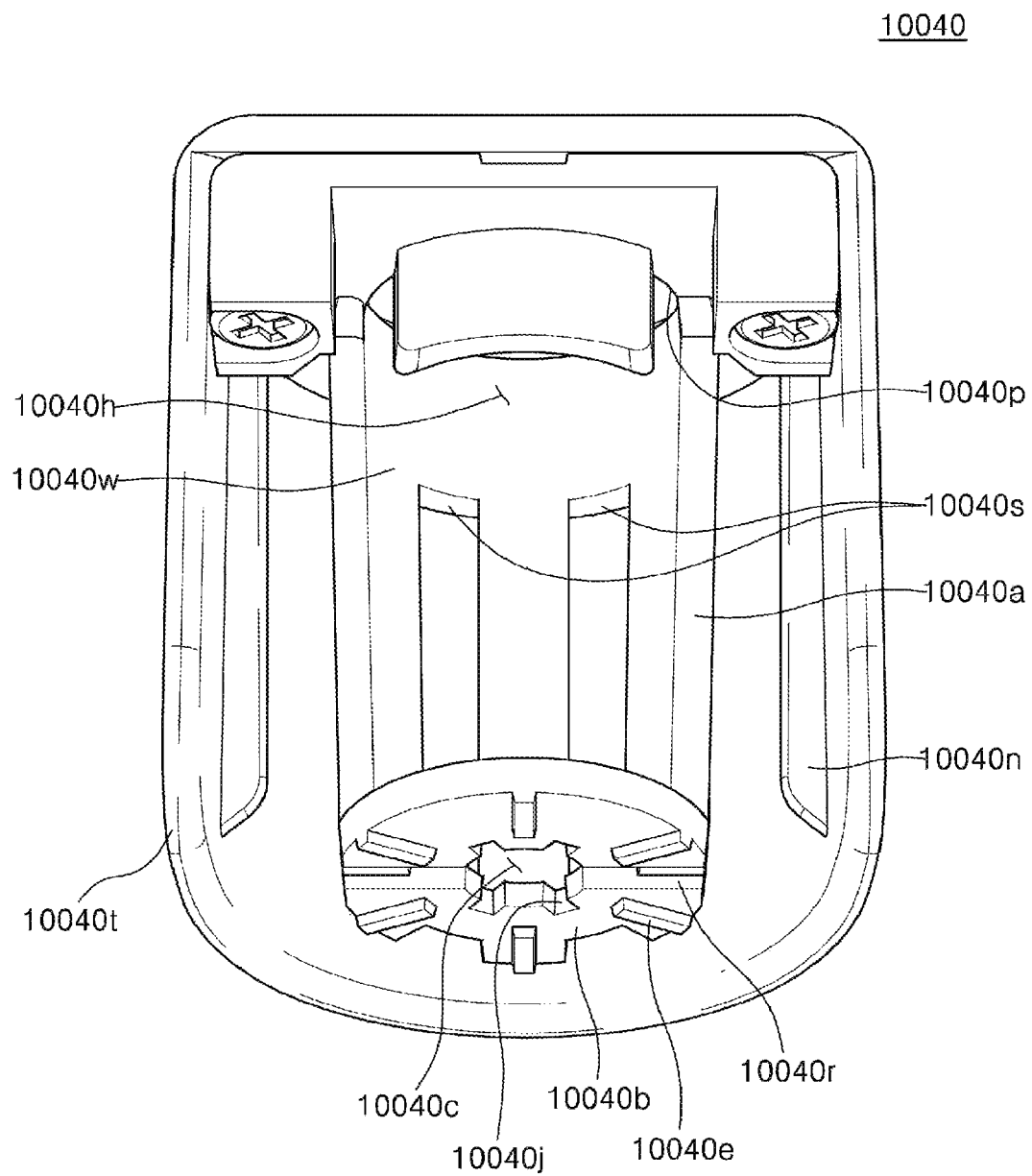
FIG. 57 is a bottom perspective view of some of components of the aerosol generating apparatus according to the embodiment shown in FIG. 54.
Figure 58:
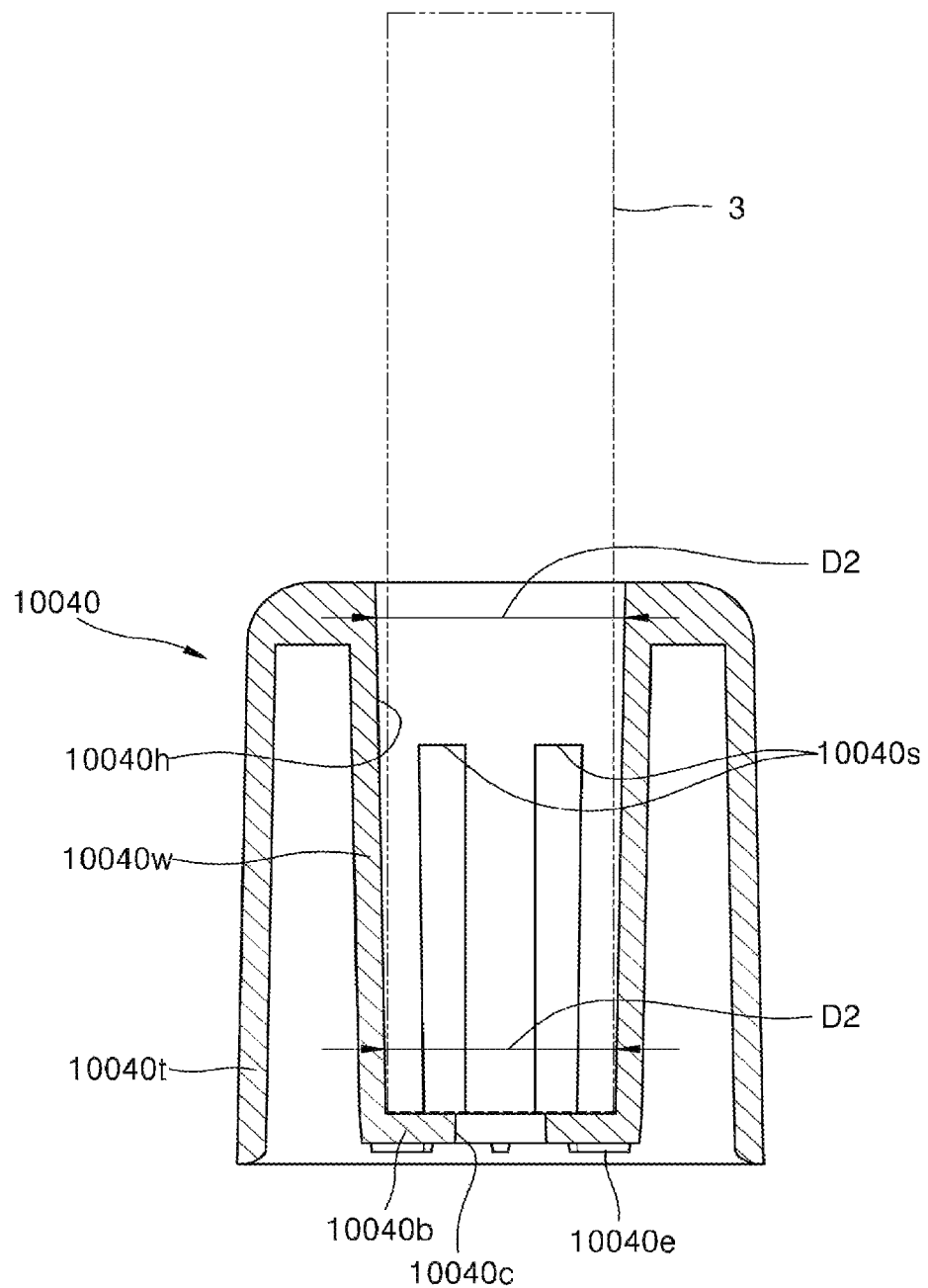
FIG. 58 is a diagram exemplifying an operating state when some of the components shown in FIG. 57 are used.

FIG. 57 is a bottom perspective view of some of components of the aerosol generating apparatus according to the embodiment shown in FIG. 54. FIG. 58 is a diagram exemplifying an operating state when some of the components shown in FIG. 57 are used.

Referring to FIGS. 57 and 58, the accommodating portion 10040 may be inserted into the combining path 10200h inside the protruding tube 10200 and includes the sidewall 10040w that forms the accommodating path 10040h capable of accommodating the cigarette 3, the insertion hole 10040p opened outward from one end of the accommodating path 10040h for insertion of the cigarette 3 thereinto, and the bottom wall 10040b that closes the other end of the accommodating path 10040h and includes the heater hole 10040c through which the end portion of the heater 10300 passes.

The heater hole 10040c formed in the bottom wall 10040b of the accommodating portion 10040 includes an outer hole 10040j recessed from the heater 10300 in the outward direction. Since a plurality of outer holes 10040j are apart from one another in the circumferential direction around the heater hole 10040c, the heater hole 10040c has a star-like shape. The outer hole 10040j functions as an air flow path that allows the air present around the heater 10300 outside the accommodating portion 10040 to be concentrated toward the cigarette 3 through the heater hole 10040c to facilitate introduction of the air into the accommodating portion 10040.

The accommodating portion 10040 includes an outer wall 10040t surrounding the sidewall 10040w and apart outwardly in the radius-wise direction of the sidewall 10040w. When the accommodating portion 10040 is coupled with the protruding tube 10200, the protruding tube 10200 is inserted between the outer wall 10040t and the sidewall 10040w, and thus the coupled state of the accommodating portion 10040 and the protruding tube 10200 may be stably maintained.

A guiding rib 10040n inserted into the guiding groove 10020n of the protruding tube 10200 when the accommodating portion 10040 is inserted into the protruding tube 10200 is installed in an outer wall 10040t.

The end portion of the heater 10300 passes through the heater hole 10040c of the accommodating portion 10040 and is located inside the accommodating path 10040h of the accommodating portion 10040 while the accommodating portion 10040 is being coupled with the protruding tube 10200. The heater 10300 is inserted into the cigarette 3 when the cigarette 3 is accommodated in the accommodating path 10040h of the accommodating portion 10040 while the accommodating portion 10040 is being coupled with the protruding tube 10200.

A plurality of bottom surface protrusions 10040e protruding from the bottom wall 10040b and apart from one another in the circumferential direction outside the heater hole 10040c are installed on the bottom surface of the bottom wall 10040b of the accommodating portion 10040. The bottom surface protrusions 10040e serve to secure an air flow path by maintaining a gap between the bottom wall 10040b and the aerosol generating apparatus when the accommodating portion 10040 is installed in the aerosol generating apparatus.

The bottom surface protrusions 10040e extend in the radial direction from the outer surface of the bottom wall 10040b toward the heater hole 10040c, and thus the air outside the bottom wall 10040b flows smoothly toward the outer hole 100401 of the heater hole 10040c through the space between the bottom surface protrusions 10040e adjacent to each other.

Due to the bottom surface protrusions 10040e, the air outside the bottom wall 10040b is uniformly supplied to the heater hole 10040c, and a uniform and constant amount of air is supplied to the cigarette 3. Therefore, aerosol having optimum flavor and aroma may be provided to a user.

An air induction groove 10040r extending from the outer end portion of the bottom wall 10040b to the heater hole 10040c is formed on the bottom surface of the bottom wall 10040b of the accommodating portion 10040. The air induction grooves 10040r provide a passageway for the mainstream of the air supplied to the cigarette 3 accommodated in the accommodating portion 10040.

An end portion of the air Induction groove 10040r located at the outer end portion of the bottom wall 10040b is disposed at a position corresponding to the air hole 10200g shown in FIG. 31. According to the arrangement structure, the air outside the protruding tube 10200 flows into the protruding tube 10200 through the air hole 10200g and is directly introduced into the heater hole 10040c along the air induction groove 10040r, the air sufficient for generating aerosol may be supplied directly to the cigarette 3.

A plurality of air induction grooves 10040r may be installed in correspondence to the number of the air holes 10200g formed in the protruding tube 10200.

The accommodating portion 10040 includes a discharging hole 10040a formed by cutting a portion of the sidewall 10040w to expose the accommodating path 10040h out of the sidewall 10040w. As the discharging hole 10040a is formed in the sidewall 10040w, the sidewall 10040w has an approximately semi-cylindrical shape. In other words, when the sidewall 10040w is cut in the direction crossing the lengthwise direction of the sidewall 10040w, the cross-sectional shape of the sidewall 10040w may be approximately semicircle.

In the embodiment shown in FIG. 57, the size of the discharging hole 10040a is approximately 180° in the circumferential direction with respect to the center axis of the sidewall 10040w in the lengthwise direction, the embodiment is not limited by the size of the discharging hole 10040a. In other words, the size of the discharging hole 10040a may be 180° or greater and less than 180° in the circumferential direction with respect to the central axis of the sidewall 10040w in the lengthwise direction.

A cleaning operation may be performed more easily by forming the discharging hole 10040a for exposing the accommodating path 10040h in the sidewall 10040w of the accommodating portion 10040.

A plurality of slits 10040s formed through the sidewall 10040w to connect the accommodating path 10040h to the outside of the accommodating portion 10040 are formed in the sidewall 10040w of the accommodating portion 10040. The slits 10040 bring the air that stays in the empty space formed between the outer wall 10040t and the sidewall 10040w into contact with portions of the outer surface of the cigarette 3 accommodated in the accommodating portion 10040.

The air staying in the empty space formed between the outer wall 10040t and the sidewall 10040w is heated by the cigarette 3 that is heated by the heater 10300 and may flow back into the accommodating path 10040h through the heater hole 10040c or may be introduced toward the cigarette 3 through the slits 10040s for assisting generation of aerosol.

Also, the air staying in the empty space formed between the outer wall 10040t and the sidewall 10040w may perform heat insulation function for preventing the heat of the cigarette 3 from being directly transmitted to the user via the accommodating portion 10040 by absorbing some of the heat of the cigarette 3.

Referring to FIG. 58, the sidewall 10040w forming the accommodating path 10040h of the accommodating portion 10040 accommodating the cigarette 3 may form a slope in the lengthwise direction of the cigarette 3. The sidewall 10040w may form a slope inclining away from the cigarette 3 in a direction from the lower end portion of the cigarette 3 accommodated in the accommodating path 10040h toward the upper end portion of the cigarette 3.

As the sidewall 10040w forms the slope as described above, the size of the accommodating path 10040h of the accommodating portion 10040 may vary in the lengthwise direction of the cigarette 3. A diameter D1 of the accommodating path 10040h in which a middle portion of the cigarette 3 is accommodated is greater than a diameter D2 of the accommodating path 10040h in which the lower end portion of the cigarette 3 is accommodated. The diameter-variable structure of the accommodating path 10040h allows the center of the cigarette 3 to be precisely aligned with the center of the heater 10300 during an operation in which the cigarette 3 is accommodated in the accommodating portion 10040. In addition, when the cigarette 3 is completely Inserted into the accommodating path 10040h, the lower end portion of the cigarette 3 is strongly pressed by the sidewall 10040w, and thus the state in which the cigarette 3 is inserted into the accommodating path 10040h may be stably maintained.

A user may directly remove the cigarette from the accommodating portion 10040 after the user smoked by using the cigarette 3 accommodated in the accommodating portion 10040. In other words, the cigarette 3 may be pulled out of the accommodating portion 10040 by holding and turning the cigarette accommodated in the accommodating portion 10040 by hand.

After the cigarette 3 is separated from the accommodating portion 10040, the user may remove the accommodating portion 10040 from the aerosol generating apparatus for a cleaning operation.

When the accommodating portion 10040 is separated from the aerosol generating apparatus, the accommodating path 10040h is exposed through the discharging hole 10040a as shown in FIG. 53, and thus a tobacco material may be discharged through the discharging hole 10040a out of the accommodating portion 10040. Also, the user may conveniently clean various portions of accommodating path 10040h and the sidewall 10040w while visually checking them.

The embodiments of the present disclosure may be written as computer programs and can be implemented in general-use digital computers that execute the programs using a computer readable recording medium. In addition, the structure of the data used in the above-described method may be recorded on a computer-readable recording medium through various means. Examples of the computer readable recording medium include magnetic storage media (e.g., ROM, RAM, USB drives, floppy disks, hard disks, etc.), optical recording media (e.g., CD-ROMs, or DVDs), etc.

It will be understood by one of ordinary skill in the art that various changes in form and details may be made therein without departing from the spirit and scope of the invention as defined by the appended claims. Therefore, the disclosed methods should be considered from an illustrative point of view, not from a restrictive point of view. The scope of the present disclosure is defined by the appended claims rather than by the foregoing description, and all differences within the scope of equivalents thereof should be construed as being included in the present disclosure.

The invention claimed is:

1. An aerosol generating apparatus that is configured to generate an aerosol by accommodating and heating a cigarette, the aerosol generating apparatus comprising
    a heater that heats the cigarette;
    a main body in which the heater is installed;
    a hollow protruding tube protruding from the main body, surrounding the heater, and including an opening opened to the outside;

an accommodating portion that includes an accommodating path capable of accommodating a cigarette, and is insertable into the protruding tube or separable from the protruding tube; and a cover that is connected to an upper end of the accommodating path of the accommodating portion, includes an outside hole into which the cigarette is inserted and exposable to the outside, and is integrally coupled with the accommodating portion such that the cover is attached to and separated from the main body together with the accommodating portion, wherein the accommodating portion, the cover, and the cigarette are capable of being separated together from the main body in a state in which the outside hole of the cover is opened to the outside and the cigarette is accommodated in the accommodating portion, and one end portion of the heater is located inside the protruding tube, and the other end portion of the heater is connected to the main body.

2. The aerosol generating apparatus of claim 1, wherein the accommodating portion is capable of being inserted into the protruding tube through the opening of the protruding tube, and includes a side wall forming an accommodating path for accommodating a cigarette, an insertion hole opened to the outside at one end of the accommodating path for insertion of the cigarette thereinto, and a bottom wall configured to close the other end of the accommodating path and including a heater hole through which the end portion of the heater passes.

3. The aerosol generating apparatus of claim 2, wherein an outside air introduction gap that allows the air outside the cover to flow into the cover is formed at a portion where the cover and the main body are attached to each other, the accommodating portion further includes an outer wall surrounding the side wall and apart from the side wall outwardly in a radial direction of the side wall, the accommodating portion and the protruding tube are coupled with each other by inserting the protruding tube between the outer wall and the side wall, an air introducing gap is formed in a portion at which the outer wall of the accommodating portion and the protruding tube are attached to each other to allow the air outside the accommodating portion to flow into the accommodating portion, and the protruding tube further includes an air hole through which the air passes toward an end portion of the cigarette accommodated in the accommodating portion.

4. The aerosol generating apparatus of claim 1, wherein the cover further includes a door capable of exposing the upper end of the accommodating portion.

5. The aerosol generating apparatus of claim 4, wherein an outside air introduction gap that allows the air outside the cover to flow into the cover is formed at a portion where the cover and the main body are attached to each other, and the protruding tube further includes an air hole through which the air passes toward an end portion of the cigarette accommodated in the accommodating portion.

6. The aerosol generating apparatus of claim 2 further comprising at least one protruding portion protruding from the protruding tube and penetrating through the side wall of the accommodating portion to support the cigarette inserted into the accommodating portion.

7. The aerosol generating apparatus of claim 6, wherein a diameter of the accommodating path of the accommodating portion is larger than a diameter of the cigarette accommodated in the accommodating path, at least one through hole is formed through the side wall such that the at least one protruding portion passes therethrough, and the at least one protruding portion protrudes from a surface of the accommodating path toward the cigarette to contact an outer surface of the cigarette.

8. The aerosol generating apparatus of claim 7, wherein the at least one protruding portion includes protruding portions spaced apart from each other on the outer surface of the cigarette in a circumferential direction with respect to a center of the cigarette such that a flow path through which air flows is formed between adjacent protruding portions, and the at least one through hole includes through holes corresponding to the protruding portions.

9. The aerosol generating apparatus of claim 7, wherein the at least one protruding portion includes protruding portions spaced apart from each other on the outer surface of the cigarette in a lengthwise direction, and the at least one through hole includes a through hole extending in a lengthwise direction of the accommodating path such that the protruding portions pass through the through hole.

10. The aerosol generating apparatus of claim 7, wherein the at least one protruding portion extends in a circumferential direction with respect to a center of the cigarette such that the at least one protruding portion contacts a portion of the outer surface in a circumferential direction with respect to a center of the cigarette and a flow path through which air flows is formed.

11. The aerosol generating apparatus of claim 7, wherein the at least one protruding portion includes an inclined surface that is inclined with respect to a lengthwise direction of the accommodating path to guide movement of the cigarette when the cigarette is inserted into the accommodating path.

12. The aerosol generating apparatus of claim 2, wherein the bottom wall further includes a bottom protrusion protruding to support the bottom surface of an end portion of the cigarette.

13. The aerosol generating apparatus of claim 2, wherein the bottom wall further includes a connection passage connected to a space between an outer surface of the cigarette and the accommodating path.

* * * * *